US012087406B2

(12) United States Patent  
Curtis et al.

(10) Patent No.: US 12,087,406 B2  
(45) Date of Patent: Sep. 10, 2024

(54) METHODS USING CHROMATIN-RELATED NUCLEIC ACID SIGNALS FOR PERFORMING CLINICAL ACTIONS

(71) Applicant: The Board of Trustees of the Leland Stanford Junior University, Stanford, CA (US)

(72) Inventors: Christina Curtis, Stanford, CA (US); Anshul Bharat Kundaje, Stanford, CA (US); Chris Probert, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1217 days.

(21) Appl. No.: 16/355,590

(22) Filed: Mar. 15, 2019

(65) Prior Publication Data

US 2019/0287654 A1   Sep. 19, 2019

Related U.S. Application Data

(60) Provisional application No. 62/666,464, filed on May 3, 2018, provisional application No. 62/643,550, filed on Mar. 15, 2018.

(51) Int. Cl.
*G16B 40/20*   (2019.01)
*C12Q 1/6886*   (2018.01)

(52) U.S. Cl.
CPC .......... *G16B 40/20* (2019.02); *C12Q 1/6886* (2013.01)

(58) Field of Classification Search
None
See application file for complete search history.

(56) References Cited

U.S. PATENT DOCUMENTS

| 9,752,150 B2 | 9/2017 | Clarke et al. |
| 2010/0081129 A1 | 4/2010 | Belouchi et al. |
| 2018/0002749 A1 | 1/2018 | Larson et al. |

FOREIGN PATENT DOCUMENTS

| EP | 3765017 A1 | 1/2021 |
| HK | 40045556 A | 10/2021 |
| WO | 2015134523 A1 | 9/2015 |
| WO | 2018009723 A1 | 1/2018 |
| WO | 2019178563 A1 | 9/2019 |

OTHER PUBLICATIONS

Ernst, Jason, and Manolis Kellis. "Discovery and characterization of chromatin states for systematic annotation of the human genome." Nature biotechnology 28.8 (2010): 817-825.*
Extended European Search Report for European Application No. 19766942.7, Search completed Oct. 20, 2021, Mailed Oct. 28, 2021, 9 Pgs.
International Preliminary Report on Patentability for International Application PCT/US2019/022615, Report issued Sep. 15, 2020, Mailed Sep. 24, 2020, 11 Pgs.
Anshul et al., "Deep Learning Frameworks for Regulatory Genomics and Epigenomics", Regulatory Genomics and Epigenomics, Mar. 8, 2016, XP055852658, 44 pgs.
International Search Report and Written Opinion for International Application No. PCT/US2019/022615, Search completed May 8, 2019, Mailed Jun. 14, 2019, 16 Pgs.
Allyse et al., "Non-invasive prenatal testing: a review of international implementation and challenges", International Journal of Women's Health, vol. 7, Jan. 16, 2015, pp. 113-126.
Dunham et al., "An integrated encyclopedia of DNA elements in the human genome", Nature, vol. 489, Sep. 6, 2012, pp. 57-74.
Ernst et al., "Discovery and characterization of chromatin states for systematic annotation of the human genome", Nature Biotechnology, vol. 28, No. 8, Jul. 25, 2010, 11 pgs.
Gerstein et al., "Architecture of the human regulatory network derived from ENCODE data", Nature, vol. 489, No. 7414, Sep. 6, 2012, pp. 91-100.
He et al., "Nucleosome dynamics define transcriptional enhancers", Nature Genetics, vol. 42, No. 4, Apr. 2010, Electronic Publication: Mar. 7, 2010, 6 pgs.
Heitzer et al., "Circulating Tumor DNA as a Liquid Biopsy for Cancer", Clinical Chemistry, vol. 61, No. 1, Jan. 2015, pp. 112-123.
Heitzer et al., "Current and future perspectives of liquid biopsies in genomics-driven oncology", Nature Reviews Genetics, vol. 20, No. 2, Nov. 8, 2018, pp. 71-88.
Henikoff et al., "Epigenome characterization at single base-pair resolution", Proceedings of the National Academy of Sciences, vol. 108, No. 45, Nov. 8, 2011, p. 18318-18323.
Henikoff et al., "Simultaneous Discovery of Cell-Free DNA and the Nucleosome Ladder", Genetics, vol. 209, No. 1, May 1, 2018, pp. 27-29.
Hoffman et al., "Integrative annotation of chromatin elements from ENCODE data", Nucleic Acids Research, vol. 41, No. 2, Jan. 2013, pp. 827-841.
Jaiswal et al., "Age-Related Clonal Hematopoiesis Associated with Adverse Outcomes", The New England Journal of Medicine, vol. 371, No. 26, Dec. 25, 2014, pp. 2488-2498.
Jensen et al., "Whole genome bisulfite sequencing of cell-free DNA and its cellular contributors uncovers placenta hypomethylated domains", Genome Biology, vol. 16, No. 78, Apr. 15, 2015, 11 pgs.
Jiang et al., "The Long and Short of Circulating Cell-Free DNA and the Ins and Outs of Molecular Diagnostics", Trends in Genetics, vol. 32, No. 6, Jun. 1, 2016, Electronic Publication: Apr. 26, 2016, pp. 360-371.

(Continued)

*Primary Examiner* — G. Steven Vanni
(74) *Attorney, Agent, or Firm* — KPPB LLP

(57) ABSTRACT

Processes to reveal biological attributes from nucleic acids are provided. In some instances, nucleic acids are used to develop frequency sequence signal maps, construct V-plots, and/or to train computational models. In some instances, trained computational models are used to predict features that reveal biological attributes.

30 Claims, 57 Drawing Sheets

(56) References Cited

OTHER PUBLICATIONS

Kang et al., "CancerLocator: non-invasive cancer diagnosis and tissue-of-origin prediction using methylation profiles of cell-free DNA", Genome Biology, vol. 18, No. 53, Mar. 24, 2017, 12 pgs.
Marquard et al., "TumorTracer: a method to identify the tissue of origin from the somatic mutations of a tumor specimen", BMC Medical Genomics, vol. 8, No. 58, Oct. 1, 2015, 13 pgs.
Mouliere et al., "Enhanced detection of circulating tumor DNA by fragment size analysis", Science Translational Medicine, vol. 10, No. 466, Nov. 7, 2018, 13 pgs.
Quang et al., "YAMDA: thousandfold speedup of EM-based motif discovery using deep learning libraries and GPU", Bioinformatics, vol. 34, No. 20, Oct. 15, 2018, First Published: May 22, 2018, pp. 3578-3580, https://doi.org/10.1093/bioinformatics/bty396.
Ritchie et al., "limma powers differential expression analyses for RNA-sequencing and microarray studies", Nucleic Acids Research, vol. 43, No. 7, Article e47, Apr. 20, 2015, First Published: Jan. 20, 2015, 13 pgs., https://doi.org/10.1093/nar/gkv007.
Roadmap Epigenomics Consortium, "Integrative analysis of 111 reference human epigenomes", Nature, vol. 518, No. 7539, Feb. 19, 2015, 32 pgs.
Ryder et al., "Endocrine-related adverse events following ipilimumab in patients with advanced melanoma: a comprehensive retrospective review from a single institution", Endocrine-Related Cancer, vol. 21, No. 2, Apr. 2014, pp. 371-381.
Schep et al., "Structured nucleosome fingerprints enable high-resolution mapping of chromatin architecture within regulatory regions", Genome Research, vol. 25, No. 11, Aug. 27, 2015, pp. 1757-1770.
Schones et al., "Dynamic Regulation of Nucleosome Positioning in the Human Genome", Cell, vol. 132, No. 5, Mar. 7, 2008, pp. 887-898.
Segal et al., "A genomic code for nucleosome positioning", Nature, vol. 442, Aug. 17, 2006, pp. 772-778.
Shen et al., "Sensitive tumour detection and classification using plasma cell-free DNA methylomes", Nature, vol. 563, No. 7732, Nov. 14, 2018, 21 pgs.
Snyder et al., "Cell-free DNA Comprises an In Vivo Nucleosome Footprint that Informs Its Tissues-Of-Origin", Cell, vol. 164, No. 1-2, Jan. 14, 2016, pp. 57-68, https://doi.org/10.1016/j.cell.2015.11.050.
Sparks et al., "Noninvasive prenatal detection and selective analysis of cell-free DNA obtained from maternal blood: evaluation for trisomy 21 and trisomy 18", American Journal of Obstetrics and Gynecology, vol. 206, No. 4, Apr. 2012, pp. 319.e1-319.e9.
Ulz et al., "Inferring expressed genes by whole-genome sequencing of plasma DNA", Nature Genetics, vol. 48, No. 10, Oct. 2016, Electronic Publication: Aug. 29, 2016, pp. 1273-1280.
Wan et al., "Liquid biopsies come of age: towards implementation of circulating tumour DNA", Nature Reviews Cancer, vol. 17, No. 4, Apr. 2017, Electronic Publication: Feb. 24, 2017, pp. 223-238.
Williamson, "Properties of rapidly labelled deoxyribonucleic acid fragments isolated from the cytoplasm of primary cultures of embryonic mouse liver cells", Journal of Molecular Biology, vol. 51, No. 1, Jul. 14, 1970, pp. 157-168.

\* cited by examiner

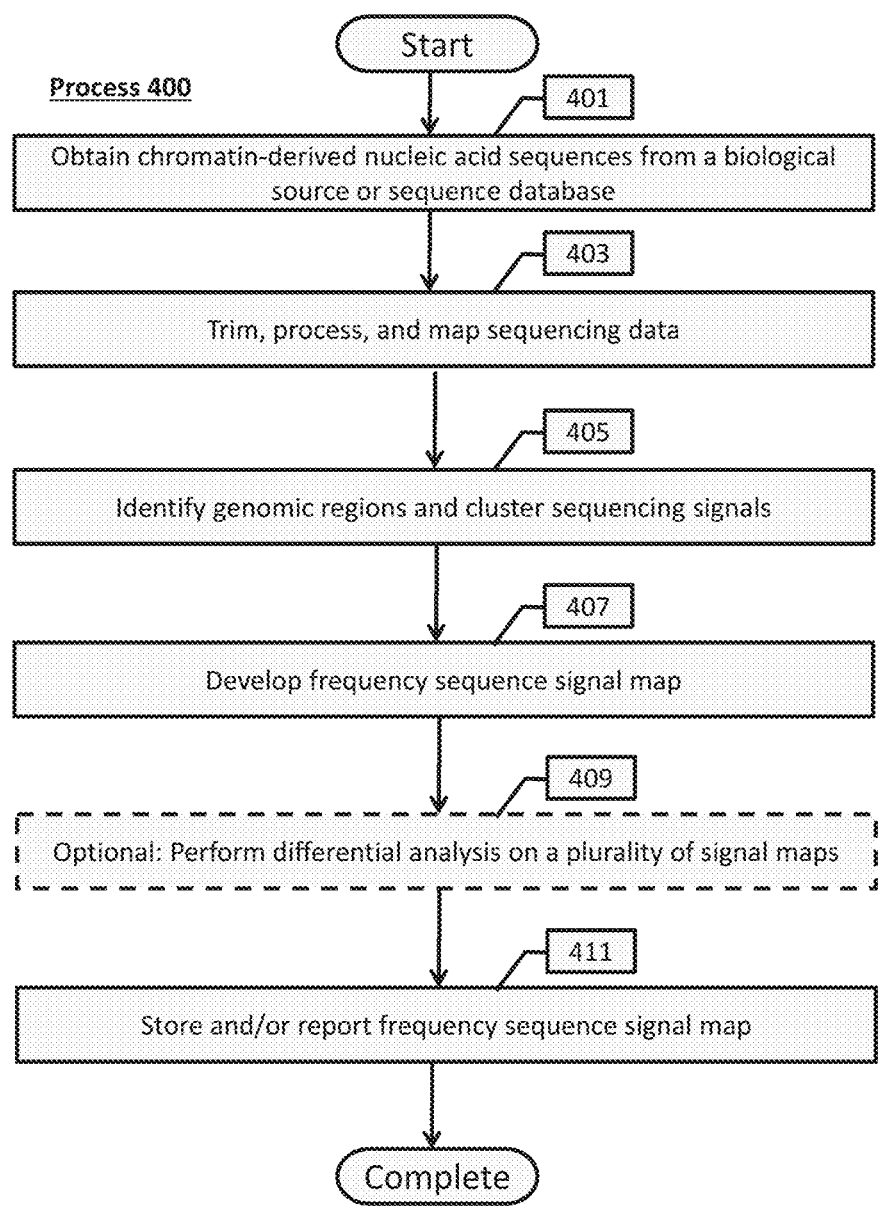

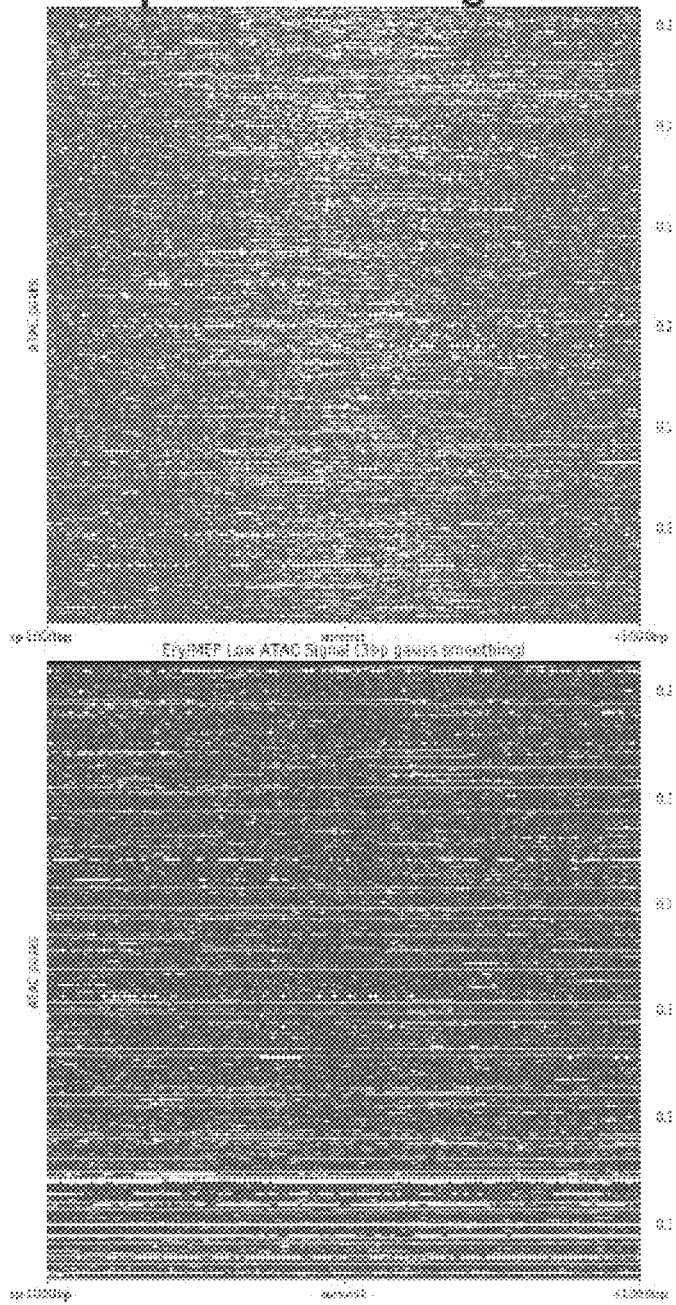

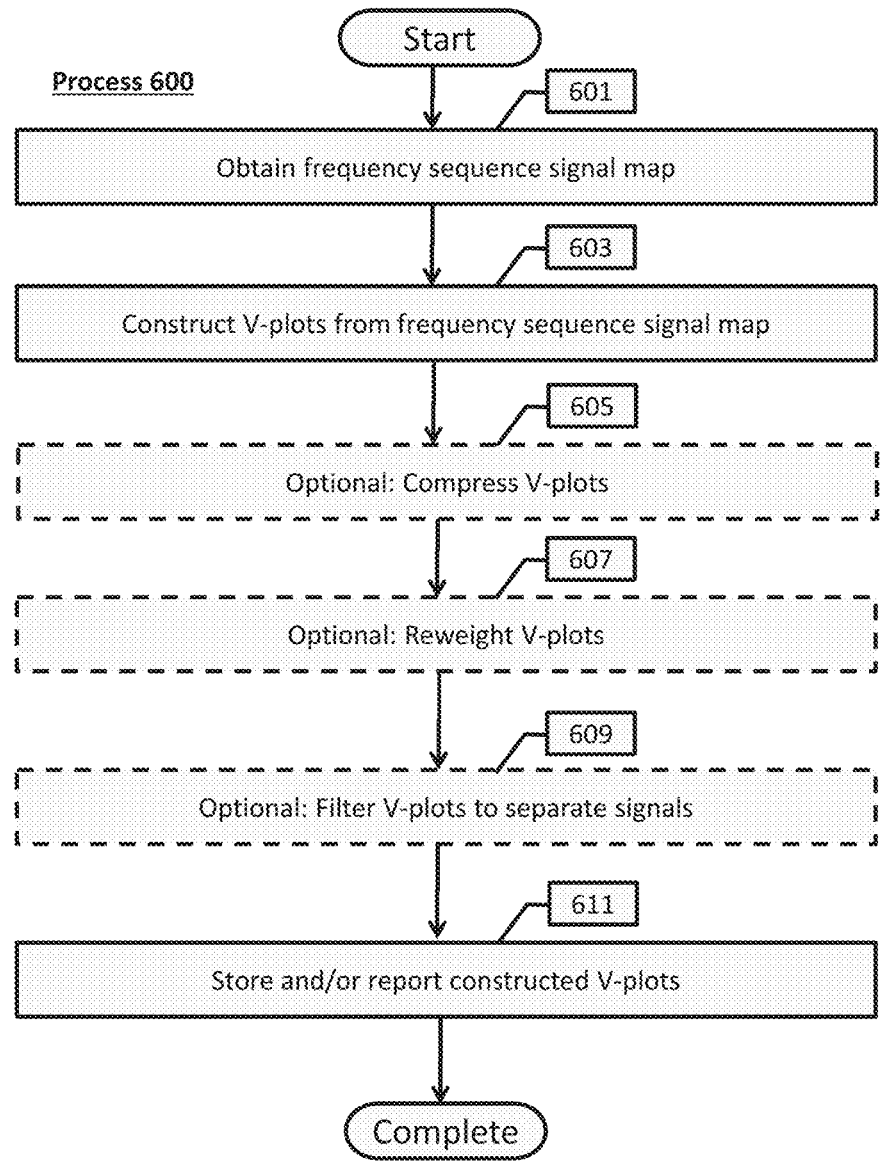

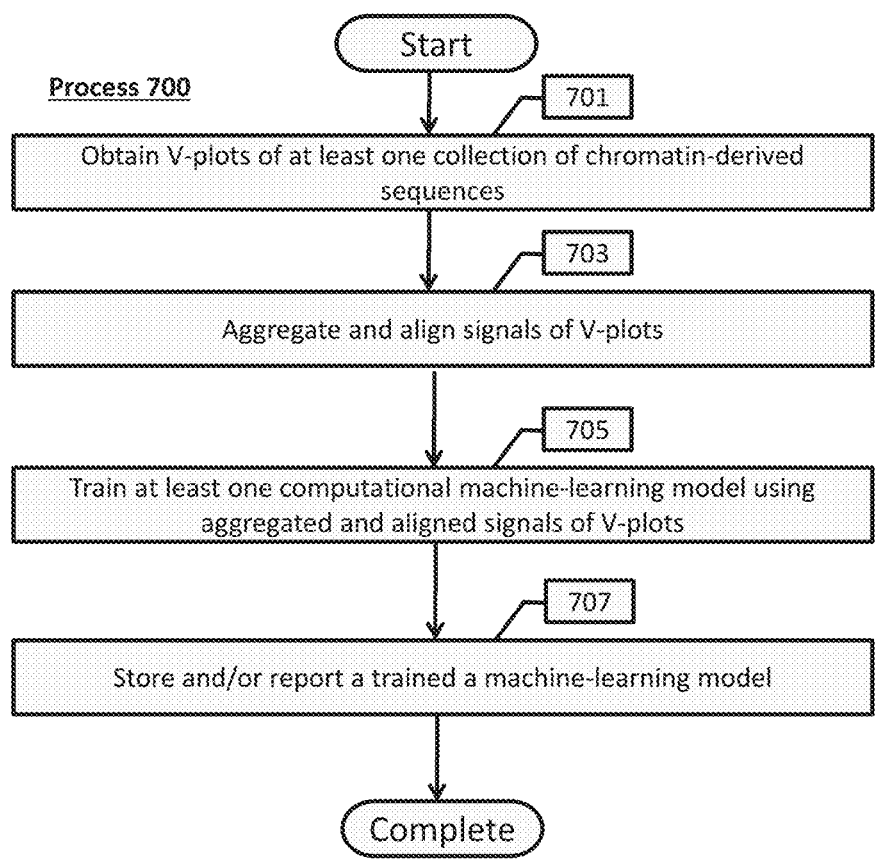

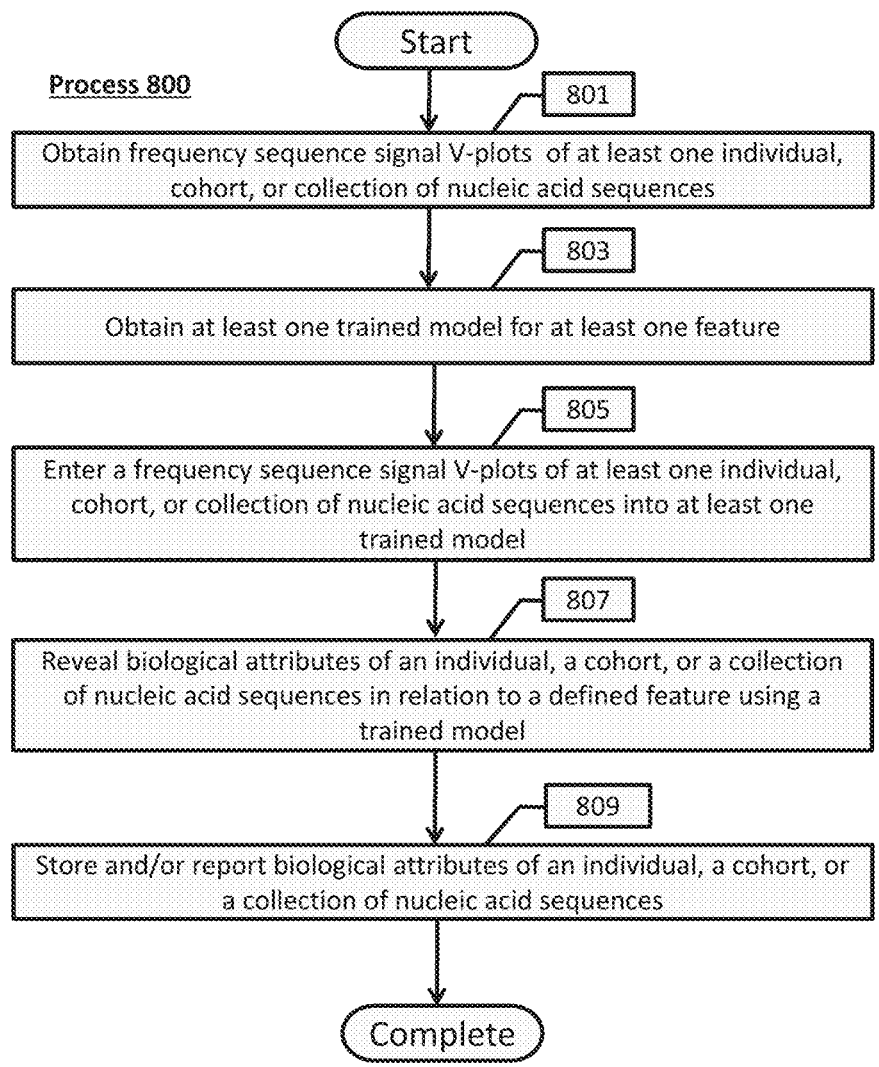

cfDNA traces at tissue-specific enhancers in the krukenberg tumor sample (pt 5)

cfDNA traces at tissue-specific enhancers in the Cutts et al melanoma sample

Fig. 24
cfDNA traces at tissue-specific enhancers in the pooled low tumor burden sample
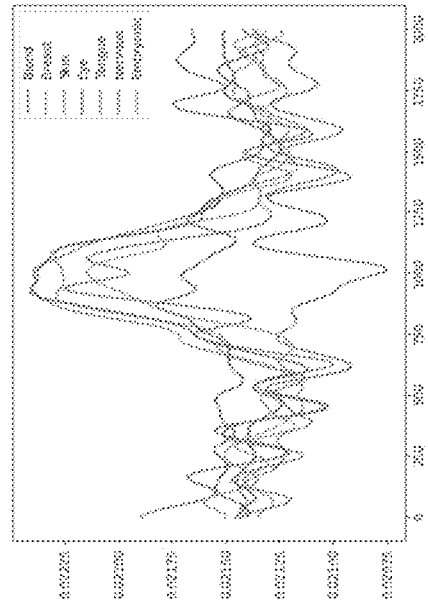
Top 1000 tissue-specific peaks
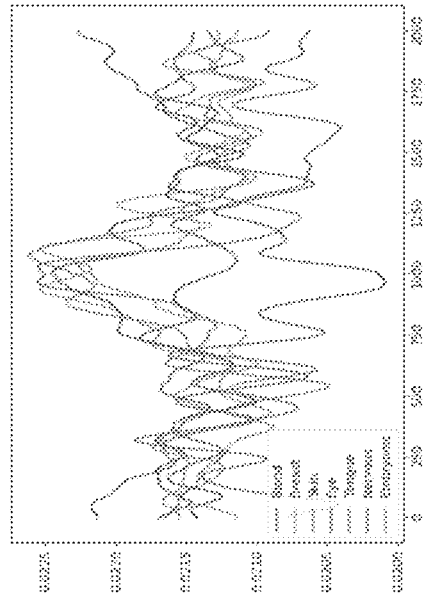
Top 5000 tissue-specific peaks

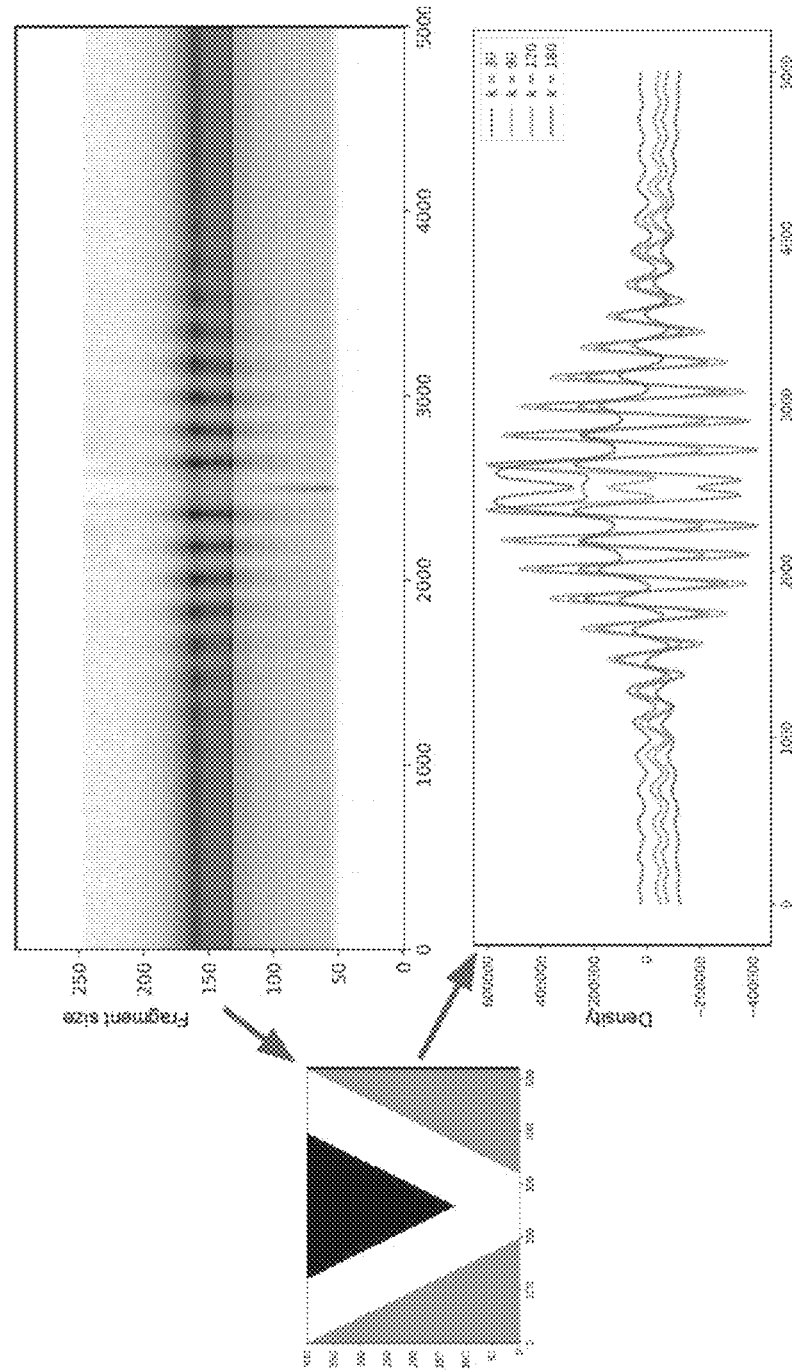

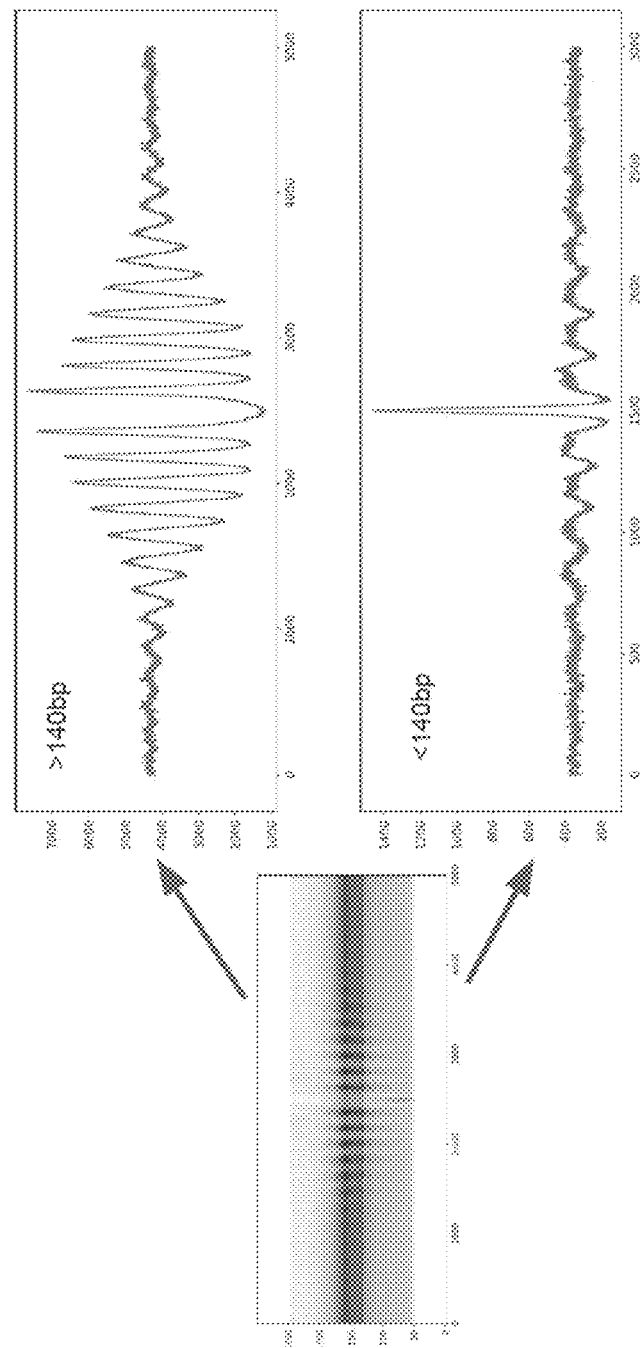

METHODS USING CHROMATIN-RELATED NUCLEIC ACID SIGNALS FOR PERFORMING CLINICAL ACTIONS

CROSS REFERENCE TO RELATED APPLICATIONS

The current application claims the benefit of and priority under 35 U.S.C. § 119(e) to U.S. Provisional Patent Application No. 62/666,464 entitled "Methods Using Nucleic Acid Signals For Revealing Inherent Qualities" to Curtis et al., filed May 3, 2018 and U.S. Provisional Patent Application No. 62/643,550 entitled "Methods using cell-free DNA sequencing of human blood plasma for noninvasive diagnostics" to Curtis et al., filed Mar. 15, 2018, the disclosures of which are incorporated herein by reference in their entireties.

FIELD OF THE INVENTION

The invention is generally directed to methods of utilizing nucleic acid sequence signals for revealing biological attributes of individuals and cohorts including deriving signals from cell-free nucleic acids.

BACKGROUND

Canonical nucleic acid polymers include DNA and RNA that formulate a sequence of nucleotides. Each nucleotide is composed of a nitrogenous base, a 5-carbon sugar (e.g., ribose), and at least one phosphate group. The four canonical bases of DNA and RNA are adenine (A), cytosine (C), guanine (G), and thymine (T) or uracil (U); however, several other noncanonical bases are often incorporated into the polymer, such as, for example, inosine (I) or methyl-7-guanosine (m7G).

Within a genome or transcriptome of an organism exist a plurality of regulatory regions, which are segments of nucleic acid molecules with a particular sequence that can influence the expression level of specific genes. Accordingly, regulation of DNA transcription or RNA translation often involve regulatory regions that cooperate with various chromatin-related factors (e.g., protein transcription factors, histones, chromatin markers, small RNAs) capable of recognizing and binding the regulatory region. Regulatory regions include promoters, enhancers, activators, repressors, silencers, insulators, untranslated regions (UTRs) of RNA, and riboswitches. Often, regulatory regions are marked by chromatin modifiers, such as detailed in the histone code (e.g., H3 methylation and acetylation).

SUMMARY OF THE INVENTION

Many embodiments are directed to methods of using chromatin derived nucleic acid sequencing data for developing a sequence signature map, constructing sequence signature V-plots, training machine-learning models to predict a feature, and revealing biological attributes of an individual or cohort.

In an embodiment, chromatin-related nucleic acid signals of an individual is determined. The chromatin-related nucleic acid signals are derived from nucleic acids extracted from the individual. The chromatin-derived nucleic acid signals are a frequency of chromatin-derived sequences at a particular genomic locus that are aligned in a pattern indicating association with a chromatin-related factor. Whether a biological attribute is associated with the individual's chromatin-related nucleic acid signals is determined using a computational model trained with chromatin-related nucleic acid signals associated with the biological attribute. The biological attribute is one of: a phenotype, a disorder, tissue origin, a cell type, chromatin status, or an activation of a transduction pathway. An association of the biological attribute with the individual's chromatin-related nucleic acid signals indicates at least one clinical status selected from: pathological status of a disorder, activation of the immune system, neoplasia, inflammation, placental disorder, tissue damage, and neurodegeneration. Based on the indication of the at least one clinical status, a clinical action is performed. The clinical is action is one of: administering a diagnostic test on the individual or administering a treatment to the individual.

In another embodiment, the extracted nucleic acids are extracellular nucleic acids.

In yet another embodiment, the extracted nucleic acids are one of: cell-free DNA or cell-free RNA.

In a further embodiment, the extracted nucleic acids are RNA. The RNA is used to derive the chromatin-related nucleic acid signals.

In still yet another embodiment, the extracted nucleic acids are extracted from at least one of: blood, plasma, serum, lymphatic fluid, cerebral spinal fluid, urine, feces tissue biopsy, or isolated single cells.

In yet a further embodiment, the at least one chromatin-related factor includes at least one of: a chromatin marker, a histone, a histone variant protein, a DNA-methyl-binding protein, a transcription factor, an enhancer, and a repressor.

In an even further embodiment, the chromatin-related nucleic acid signals are assigned a genomic position based on a reference sequence.

In yet an even further embodiment, the chromatin-related nucleic acid signals are clustered based on their genomic position to yield a frequency sequence signal map.

In still yet an even further embodiment, determination of whether a biological attribute is associated with the individual's chromatin-related nucleic acid signals further includes constructing V-plots for the chromatin-related nucleic acid signals of the individual. The V-plots are each a 2-D pattern of a number sequence read fragments. The he fragment length is plotted against fragment position in genome. The determination of whether a biological attribute is associated with the individual's chromatin-related nucleic acid signals further includes associating the V-plots with the biological attribute. The determination of whether a biological attribute is associated with the individual's chromatin-related nucleic acid signals further includes aggregating and aligning V-plots based on genomic position. The determination of whether a biological attribute is associated with the individual's chromatin-related nucleic acid signals further includes entering the V-plots into the trained computational model to determine whether the biological attribute is associated with the individual's chromatin-related nucleic acid signals.

In still yet an even further embodiment, he determination of whether a biological attribute is associated with the individual's chromatin-related nucleic acid signals further includes compressing the V-plots by binning or pooling sequence read fragments. The determination of whether a biological attribute is associated with the individual's chromatin-related nucleic acid signals further includes reweighing the V-plots based on the sequence composition or sequence frequency. The determination of whether a biological attribute is associated with the individual's chromatin-related nucleic acid signals further includes filtering the V-plots to further differentiate the corresponding signals of each V-plot.

In still yet an even further embodiment, the trained computational model is one of: a generative adversarial network, a convolutional neural network, a random forest, a support vector machine, or a boosted decision trees.

In still yet an even further embodiment, the trained computational model has been trained utilizing at least two biological attributes to yield one of: a multi-feature model or a multilayer hierarchical model.

In still yet an even further embodiment, the association of the biological attribute with the individual's chromatin-related nucleic acid signals indicates a neoplasia. The neoplasia is one of: acute lymphoblastic leukemia (ALL), acute myeloid leukemia (AML), anal cancer, astrocytomas, basal cell carcinoma, bile duct cancer, bladder cancer, breast cancer, cervical cancer, chronic lymphocytic leukemia (CLL) chronic myelogenous leukemia (CML), chronic myeloproliferative neoplasms, colorectal cancer, endometrial cancer, ependymoma, esophageal cancer, esthesioneuroblastoma, Ewing sarcoma, fallopian tube cancer, gallbladder cancer, gastric cancer, gastrointestinal carcinoid tumor, hairy cell leukemia, hepatocellular cancer, Hodgkin lymphoma, hypopharyngeal cancer, Kaposi sarcoma, Kidney cancer, Langerhans cell histiocytosis, laryngeal cancer, leukemia, liver cancer, lung cancer, lymphoma, melanoma, Merkel cell cancer, mesothelioma, mouth cancer, neuroblastoma, non-Hodgkin lymphoma, non-small cell lung cancer, osteosarcoma, ovarian cancer, pancreatic cancer, pancreatic neuroendocrine tumors, pharyngeal cancer, pituitary tumor, prostate cancer, rectal cancer, renal cell cancer, retinoblastoma, skin cancer, small cell lung cancer, small intestine cancer, squamous neck cancer, T-cell lymphoma, testicular cancer, thymoma, thyroid cancer, uterine cancer, vaginal cancer, or vascular tumors.

In still yet an even further embodiment, a diagnostic test is administered. The diagnostic test is one of: a physical exam, medical imaging, a mammography, endoscopy, stool sampling, a pap test, an alpha-fetoprotein blood test, a CA-125 test, a prostate-specific antigen (PSA) test, a biopsy extraction, a bone marrow aspiration, and a tumor marker detection test.

In still yet an even further embodiment, a treatment is administered. The treatment is one of: surgery, chemotherapy, radiation therapy, immunotherapy, targeted therapy, hormone therapy, stem cell transplant, or blood transfusion.

In still yet an even further embodiment, the indication of neoplasia provides early cancer detection.

In still yet an even further embodiment, the indication of neoplasia is determined during a course of a treatment regime such that the effects of the treatment regime on neoplastic growth is monitored.

In still yet an even further embodiment, the indication of neoplasia is determined after a course of a treatment regime such that residual neoplastic growth or recurrence of neoplastic growth is monitored.

In still yet an even further embodiment, the association of the biological attribute with the individual's chromatin-related nucleic acid signals indicates tissue inflammation or tissue damage. The tissue inflammation or tissue damage is one of: appendicitis, colitis, Crohn's disease, cystitis, endocarditis, gastritis, hepatitis including cirrhosis, inflammatory bowel disease, myocarditis, neuritis, pancreatitis, pericarditis, or pneumonitis.

In still yet an even further embodiment, a diagnostic test is administered. The diagnostic test is one of: a physical exam, medical imaging, a biopsy extraction, endoscopy, an echocardiogram, an electrocardiogram, a pulmonary function test, or a blood test.

In still yet an even further embodiment, a treatment is administered. The treatment is one of: surgery, administration of an anti-inflammatory, administration of an antibiotic, administration of an antiviral, intravenous fluids, and administration of a pain reliever.

In still yet an even further embodiment, the indication of tissue inflammation or tissue damage is determined after a course of a treatment regime such that residual tissue inflammation or tissue damage or recurrence of tissue inflammation or tissue damage is monitored.

In still yet an even further embodiment, the association of the biological attribute with the individual's chromatin-related nucleic acid signals indicates neurodegeneration. The neurodegeneration is one of: Alzheimer's disease, amyotrophic lateral sclerosis (ALS), dementia, Huntington's disease, or Parkinson's disease.

In still yet an even further embodiment, a diagnostic test is administered. The diagnostic test is one of: a physical exam, medical imaging, a biopsy extraction, a neurological test, an electrodiagnostic test, a memory test, a genetic test, and a blood test.

In still yet an even further embodiment, a treatment is administered. The treatment is one of: surgery, an anti-inflammatory, an antibiotic, an antiviral, intravenous fluids, and a pain reliever.

In still yet an even further embodiment, the indication of neurodegeneration is determined during a course of a treatment regime such that the neurodegeneration process is monitored.

In still yet an even further embodiment, the association of the biological attribute with the individual's chromatin-related nucleic acid signals indicates a placental disorder. The placental disorder is one of: placental abruption, placenta accrete, placenta increta, placenta percreta, chorioamnionitis, intervillositis, TORCH infections, cytomegalovirus infection, chronic deciduitis, circumvallate placenta, placenta previa, vasa previa, chorangioma, placental infarction, choriocarcinoma, or hydatidiform mole.

In still yet an even further embodiment, a diagnostic test is administered. The diagnostic test is one of: physical exam, medical imaging, and blood tests.

In still yet an even further embodiment, a treatment is administered. The treatment is one of: surgery, Cesarean section, anti-inflammatories, antibiotics, antivirals, intravenous fluids, and pain reliever.

In still yet an even further embodiment, the indication of the placental disorder is determined during a course of a pregnancy such that the pathology of the placental disorder is monitored.

In an embodiment, biological attributes from nucleic acids are revealed using a computing system. A reference frequency signal map having a plurality of signals is obtained using a computing system. Each signal corresponds to the frequency of sequence read fragments of a reference sequence at a particular genomic region. A referential V-plot for each signal of the referential frequency signal map is constructed using the computing system. Each referential V-plot is a measure of the frequency of sequence read fragments of the reference sequence. The plurality of referential V-plots are aggregated into a plurality of aggregated referential V-plots using the computing system. Each aggregated referential V-plot corresponds to a feature. A model with the plurality of compressed referential V-plots such the model is trained to predict each feature associated with each compressed referential V-plot. Biological attributes of a chromatin-derived nucleic acid sample are revealed using the computing system. The biological attributes are revealed by entering constructed sample V-plots derived from the chromatin-derived nucleic acid sample in the trained model to predict sample features. The biological attributes are the predicted sample features In another embodiment, the reference frequency signal map is developed by the following. A plurality of chromatin-derived referential nucleic acid sequence read fragments are obtained using the computing system. The plurality of chromatin-derived referential nucleic acid sequence read fragments is the reference sequence. The chromatin-derived referential nucleic acid sequence read fragments are mapped to an assembled genome to reveal their genomic region using the computing system. The chromatin-derived referential nucleic acid sequence read fragments within the same genomic regions are clustered to reveal the plurality of signals of the reference frequency signal map using the computing system.

In yet another embodiment, differential analysis is performed using the computing system by comparing the reference frequency signal map with a second frequency signal map.

In a further embodiment, each referential V-plot is reweighted based on its observed-to-expected GC content ratio.

In still yet another embodiment, each referential V-plot is reweighted based on a copy number aberration.

In yet a further embodiment, each referential V-plot is filtered using a design or learned filter.

In an even further embodiment, the model is selected from the group consisting of: generative adversarial networks (GANs), convolutional neural networks (CNNs), random forests, support vector machines (SVMs), and boosted decision trees.

In yet an even further embodiment, the chromatin-derived nucleic acid sample is derived from a cohort of individuals.

In still yet an even further embodiment, the chromatin-derived nucleic acid sample is derived from an individual.

In still yet an even further embodiment, a biological sample from the individual having nucleic acids is extracted. A sample sequence library from the sample-derived nucleic acids is constructed. The sample sequence library to yield a plurality of sample nucleic acid sequence read fragments is sequenced. The plurality of sample nucleic acid sequence read fragments is a sample sequence. The sample nucleic acid sequence read fragments to the assembled genome to reveal their genomic region is mapped using the computing system. The sample nucleic acid sequence read fragments within the same genomic regions is clustered to reveal the plurality of signals of the reference frequency signal map using the computer system. A sample V-plot for each signal of the sample frequency signal map is constructed. Each sample V-plot is a measure of the frequency of sequence read fragments of the sample sequence In still yet an even further embodiment, the nucleic acids are cell-free nucleic acids

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

FIG. 4 provides a flow diagram of a process to develop a frequency signal map in accordance with an embodiment of the invention.

FIG. 6 provides a flow diagram of a process to construct V-plots in accordance with an embodiment of the invention.

FIG. 7 provides a flow diagram of a process to train a computational model in accordance with an embodiment of the invention.

FIG. 8 provides a flow diagram of a process to reveal an individual's biological attributes in accordance with an embodiment of the invention.

FIGS. 18-24 provide exemplary filtered and compressed V-plots of cell-free DNA samples derived from individuals having a neoplasm, generated in accordance with various embodiments of the invention.

FIG. 25B provides a parameterized filter wherein k is the width of the filter to extract various signals at various widths in accordance with various embodiments of the invention.

FIG. 26 provides V-plot signals separated by fragment length, generated in accordance with various embodiments of the invention.

DETAILED DESCRIPTION

Figure 1:
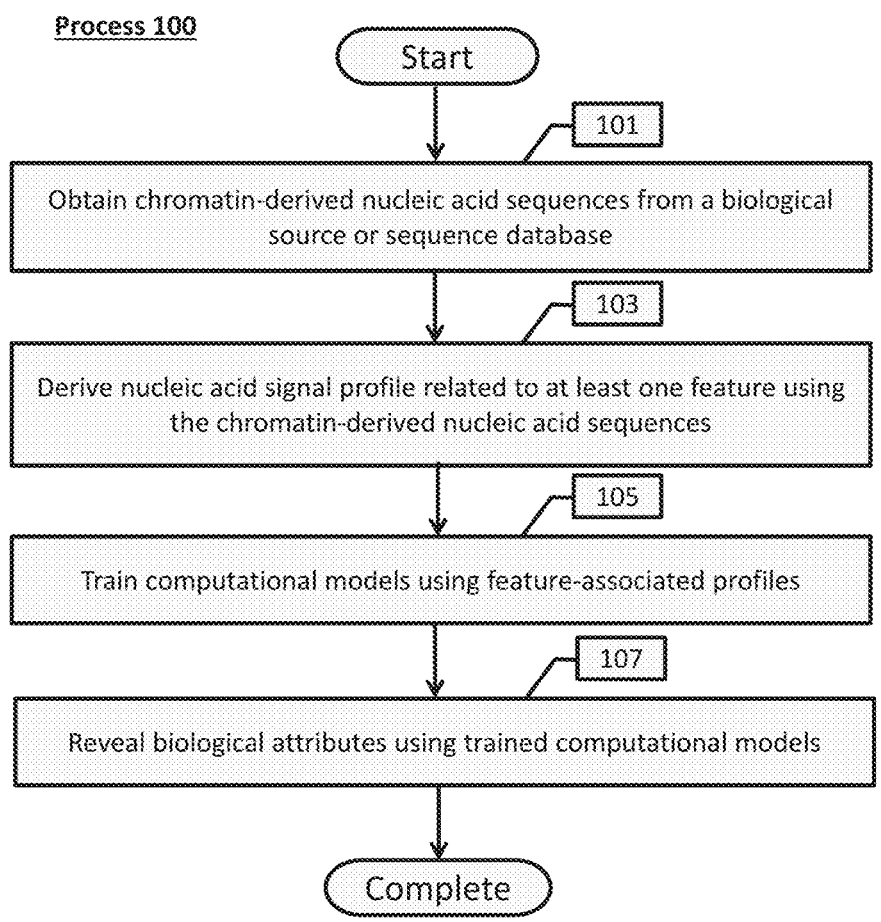
FIG. 1 provides a flow diagram of an overview process to reveal biological attributes of an individual or cohort in accordance with an embodiment of the invention.

Turning now to the drawings and data, processes to utilize chromatin-derived DNA to yield signals signifying a biological attributes are provided. In several embodiments, various methods develop frequency signal maps, construct V-plots, train computational models to predict features, and reveal biological attributes of an individual or cohort are provided. In several embodiments, revelation of biological attributes is used in a downstream application, including (but not limited) developing diagnostic tests, performing diagnoses, monitoring health status, and treating individuals.

In several embodiments, nucleic acid sequence data is obtained from DNA or RNA and utilized to infer chromatin signatures of the biological source from which the nucleic acid sequence data was derived. In many embodiments, chromatin signatures are based on frequency of a chromatin-derived sequence (i.e., a DNA sequence that associates with a chromatin marker, transcription factor, or other chromatin-related factors). In some embodiments, a chromatin-related factor is a protein, a nucleic acid, or other biomolecule that associates with DNA to regulate chromatin architecture and cellular transcription, which includes (but not limited to) chromatin markers, histones, histone variant proteins, DNA-methyl-binding proteins, transcription factors, enhancers, repressors, various DNA sequences, various DNA secondary structures, and various RNA molecules. In a number of embodiments, signals from a chromatin signature are used to train a model in relation to a biological attribute such that the model is able to predict the presence of that biological attribute in nucleic acid sequence data to be tested. In other words, once a model is trained, nucleic acids from a source (e.g., cell-free DNA derived from an individual's blood) can be examined to determine whether the nucleic acid has the biological attribute, as determined from its chromatin signature. In some embodiments, biological attributes include (but are not limited to) a phenotype, a disorder, a physiological condition a tissue origin, chromatin status, or a cell type. Thus, in various embodiments, nucleic acids of an individual are utilized to determine if that individual has a particular phenotype, disorder, or physiological condition, or to determine the tissue or cell origin of the individual's nucleic acids.

Many embodiments are directed to utilizing sequencing data to establish reference frequency signal maps having a plurality signals that correspond to the frequency of read fragments at a particular genomic region. In various embodiments, V-plots are constructed for each signal of a frequency signal map. Some embodiments are directed to compressing V-plots and associating V-plots with one or more features. Multiple embodiments are directed to training a computational model using a plurality of V-plots associated with the one or more features such that the computational model is trained to predict the one or more features. In numerous embodiments, biological attributes of an individual or cohort can be revealed using trained computational models.

A number of embodiments are also directed to utilizing nucleic acids (e.g., cell-free DNA) in a diagnostic scan of an individual to indicate whether an individual has a clinical status of a medical disorder including (but not limited to) neoplasms, placental disorder, inflammation, tissue damage, and neurodegeneration. In several embodiments, a trained computational model utilizes the chromatin signature of an individual's cell-free nucleic acids to determine tissue origin, cell-type origin, and/or chromatin status, which in turn indicates a medical diagnosis. In many embodiments, based on an initial diagnostic scan, further diagnostic tests and/or treatments are performed.

Processes to Reveal Biological Attributes

A number of embodiments are directed to revealing biological attributes, such as a disposition, of an individual, a cohort, or some other collection of nucleic acid sequence data. Biological attributes, in accordance of many embodiments, are revealed via sequence signal profiles and computational models built and developed using signal profiles. Revealed biological attributes can be any attribute that can be defined by or associated with a feature. For example, disposition to a disease or disorder (e.g., cancer) can be revealed by various processes in accordance with a number of embodiments.

Input data, as utilized by processes in accordance with many embodiments, is chromatin derived nucleic acid sequence data (i.e., sequences and fragments of sequences related to active RNA transcription and sequences and fragments of sequences related to factors bound to nucleic acids such as, protein transcription factors, chromatin modifiers etc.). In several embodiments, relative levels of chromatin derived nucleic acid sequence data are used as signals to develop signatures associated with a feature. A feature, in accordance with numerous embodiments, is a biological description that can be used to describe a collection of signals. For example, in various embodiments, a feature is a phenotype, a disorder, tissue origin, a cell type, chromatin status, or an activation of a transduction pathway. Accordingly, multiple embodiments utilize signal collections derived from input data to build feature-related computational models, which in turn, can be used to reveal biological attributes.

Provided in FIG. 1 is an embodiment of an overview process to reveal biological attributes of chromatin-derived nucleic acids of an individual, a cohort, or some other collection of sequence data. As depicted, process 100 can begin by obtaining (101) chromatin derived nucleic acid sequences from a biological source or sequence database.

Chromatin derived nucleic acid sequences, in accordance with many embodiments, are sequences related to active RNA regulation, such as RNA molecules themselves and DNA molecules associated with factors, especially regulatory regions. These factors can be DNA-binding proteins (e.g., transcription factors, chromatin modifiers), or other factors that interact with nucleic acids. Chromatin derived nucleic acid molecules and their sequences can be obtained by a number of methods practiced in the art. Factor association with nucleic acids can be used as signals indicative of a number features, as to be discussed in further detail below.

Figure 2:
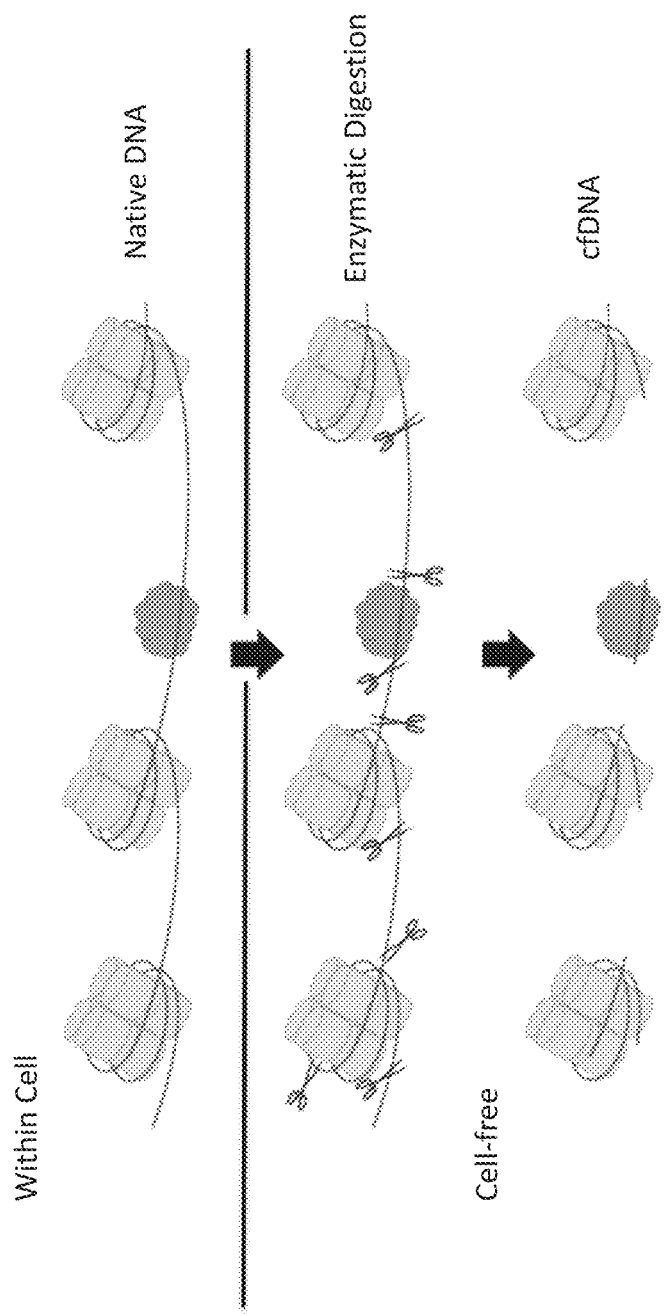
FIG. 2 provides a schematic diagram of cell-free nucleic acids, which are used in accordance with various embodiments of the invention.

In some embodiments, sequences of cell-free nucleic acid (cfNA) molecules are used as the input sequence. Cell-free DNA (cfDNA) and cell-free RNA (cfRNA) are excellent sources of chromatin derived nucleic acids due to, in part, the ease of acquisition of these biomolecules. Cell-free nucleic acids are fairly abundant in a number of easily obtainable biological sources, such as blood, plasma, lymphatic fluid, cerebral spinal fluid, urine, feces, etc. The appropriate cellular source will often depend on the process, the features to be examined, and resultant biological attributes to be revealed. Typically, cfNAs are highly abundant with both active RNA molecules and chromatin derived DNA, which is depicted in FIG. 2. Native DNA, as it would exist in a cell, are extended polymers with numerous portions the polymer attached to factors and chromatin modifiers. As DNA is released from a cell (e.g., cellular lysis) into an extracellular space, enzymes digest the nucleic acid into small pieces. DNA molecules associated with a factor, however, are more protected and thus exist in relatively higher numbers in extracellular spaces and thus are in higher numbers in biological fluids and waste. Once cfNAs are extracted from a biological source, they can be prepared and sequenced, by a number of methods known in the field. For more detailed description of chromatin-derived cfDNA, see Snyder, et al., *Cell* 164, 57-68 (2016). It is noted that although DNA is depicted in FIG. 2, similar mechanisms may also exist for RNA, as appreciated by those skilled in the art. It should be further understood that RNA molecules devoid of protein association, especially those actively and highly transcribed, can also be extracted biological sources and can be used as source of chromatin-derived nucleic acids.

Another source of RNA molecules are derived from exosomes, which are cell-derived vesicles that are present in bodily fluids (e.g., blood, plasma, lymphatic fluid, cerebral spinal fluid, urine, etc.) and in media derived from in vitro cultured cells. Exosomes can be harvested and/or isolated by a number of methods, from which RNA can be extracted and used as input sequence in accordance with various embodiments of the invention.

An emerging source of cfNAs is from in vitro cultures of organoids, which are three-dimensional multi-cellular, self-organized growth that often mimics actual organs on a much smaller scale. Organoids can release cfNAs into the media, which can easily be harvested, prepared and used as input sequence, in accordance with numerous embodiments.

In numerous embodiments, chromatin derived nucleic acids can be derived from a cellular source, such as a tissue (e.g., biopsy), an in vitro cell line, or isolated single cells (e.g., circulating tumor cells isolated from blood). The appropriate cellular source will often depend on the process, the features to be examined, and resultant biological attributes to be revealed. For any cellular source, chromatin derived nucleic acid molecules can be isolated, purified, or concentrated by a number of methods known in the field, such as (but not limited to) nucleic acid digestion and chromatin immunoprecipitation (ChIP). For example, cfDNA can be extracted from a biological source and chromatin modifier (e.g., H3K27ac) specific antibodies can be used to isolate and concentrate sequences that associated with a particular chromatin modifier, or a combination of chromatin modifiers, by ChIP. Accordingly, various embodiments isolate, purify, and/or concentrate chromatin-derived nucleic acids associated with chromatin modifiers that signify active and/or repressed regulatory regions. A number of chromatin modifiers are known in the art, including (but not limited to) H3K4me, H3K4me2, H3K4me3, H3K9me, H3K9me2, H3K9me3, H3K9ac, H3K27me, H3K27me2, H3K27me3, and H3K27ac. Chromatin derived nucleic acid molecules can be prepared into a library and sequenced by a number of known methods.

Several embodiments derive chromatin derived nucleic acid sequences from publicly or privately available databases, especially epigenetic databases. These databases store a number of experimental sequencing results from numerous biological sources. Databases that have a large amount of chromatin derived nucleic acid sequence data include (but are not limited to) Encyclopedia of DNA Elements (ENCODE), the International Human Epigenome Consortium (IHEC), the NIH Roadmap Epigenomics Mapping Consortium, The Cancer Genome Atlas (TCGA) and International Cancer Genome Consortium (ICGC).

It is to be understood by that DNA sequences associated with particular chromatin modifiers are closely linked to actively transcribed RNA sequences. Accordingly, in several embodiments RNA expression data can be derived from chromatin modifier DNA data, and vice versa. Integration of RNA expression data and chromatin modifier DNA data together can be used to enhance or cross correlate the various data sets.

In a number of embodiments, expression datasets (e.g., RNA-seq datasets) can be used to derive chromatin derived nucleic acid sequence data. By obtaining gene expression signatures and chromatin linkage data (e.g., chromatin conformation capture sequencing (Hi-C), coexpression, coregulation, genomic proximity, imputed gene-enhancer links, etc.) along with an input set of genomic regulatory elements, a set of chromatin-derived nucleic acid sequences is derived from the linkage between regulatory elements and expression signatures. Input transcripts, isoforms, or genes are linked to regulatory elements using the linkage information, and scores for each regulatory elements are calculated based on a function of transcripts they are linked to, and information on the linkage edges. Such a function can be written as a diffusion process, where the linkage matrix is the coupling between the transcript, isoform, or gene space, and weights from transcripts are propagated to regulatory elements. Priors may exist over regulatory elements, which can be formulated as an additional term in the equation.

Some embodiments also incorporate expression profiles of pseudogenes, alternative transcripts, and/or alternative isoforms to derive chromatin-derived nucleic acid sequence data using chromatin linkage data. Such analysis may be common in, for example, single-cell RNA-seq, and can also be used to overcome dataset-specific biases. In various approaches, sets of genes, transcripts, or isoforms ("pseudogenes", "pseudotranscripts", or "pseudoisoforms") are linked to regulatory elements as described in the preceding description.

Multiple embodiments also group and cluster chromatin-derived nucleic acid sequences a priori or adaptively, including using prior knowledge such as co-regulation or regulatory element interaction priors (e.g., chromatin-derived nucleic acid sequences known to be activate cooperatively upon transduction pathway activation). Adaptive clustering is possible based on linkage terms and factor analysis.

Returning to FIG. 1, chromatin-derived nucleic acid sequences can be used to derive (103) a chromatin-derived nucleic acid signal profile related to at least one feature. In many embodiments, chromatin-derived nucleic acid sequences are processed and mapped to determine their genomic regions. Sets of regions may define a signature, and can be annotated with a feature. Signal profiles, in accordance of a number of embodiments, can be weighted and/or filtered.

A feature, in accordance with numerous embodiments, is a biological description that can be used to describe a signature of signals. For example, in some embodiments, a feature is a phenotype, a disorder, tissue origin, a cell type, physiological condition, chromatin status, or an activation of a transduction pathway. It should be understood that signal profiles can be created for a single feature, a combination of features, or a collection of signals lacking a feature (e.g., signal profile excluding a certain cell type).

Figure 3:
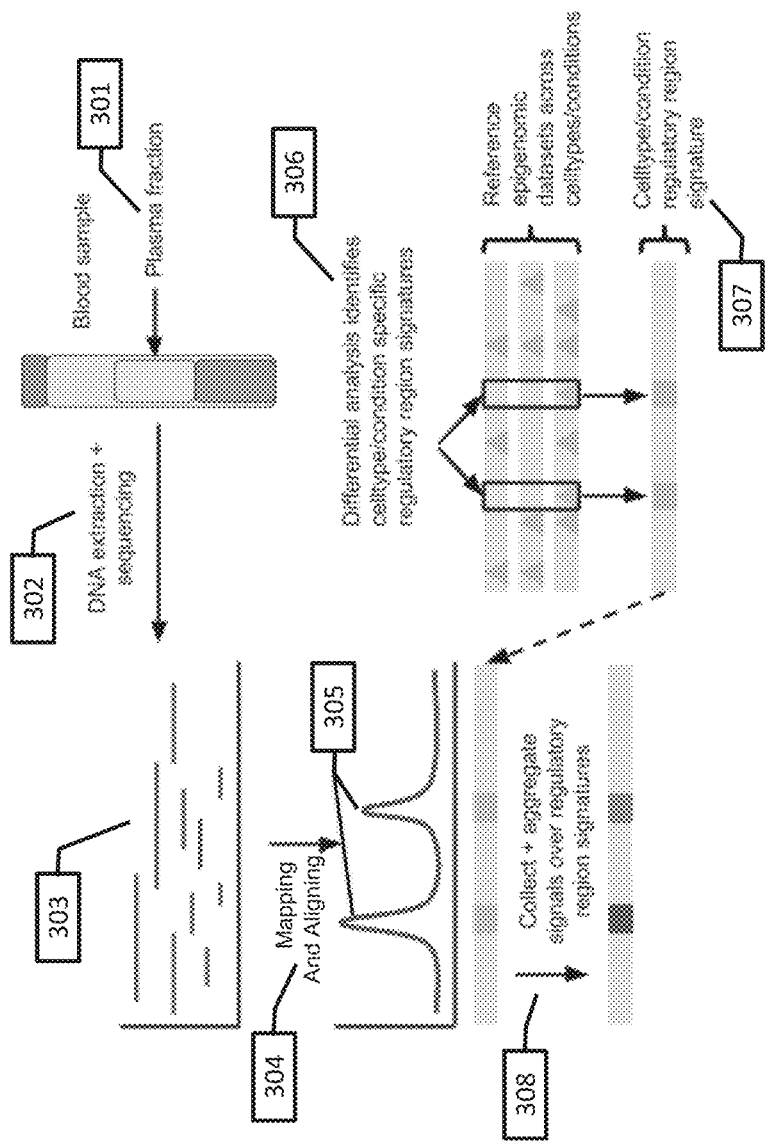
FIG. 3 provides a schematic flow chart to derive a signature sequence signal from a nucleic acid source such as plasma in accordance with an embodiment of the invention.

Provided in FIG. 3 is an exemplary overview process to derive a chromatin-derived nucleic acid signal profile. In this example, chromatin-derived nucleic acid sequences are obtained from the cfDNA source (e.g., plasma fraction of a blood sample) (301), which are extracted and sequenced (302) to obtain a plurality of sequencing reads (303). Sequencing reads are processed, mapped, and aligned (304) to reveal signals (305) associated with chromatin-derived sequence reads (e.g., regulatory regions). Differential analysis identifies (306) feature-associated (e.g., cell type, physiological condition) signatures (307), which are a collection of signals that are signify the feature. The signals can be collected and aggregated (308), which can be stored in a memory or presented to a user for downstream analysis.

Using feature-associated signal profiles, computational models can be trained (105) classify the signal profiles. In several embodiments, signal profiles that are annotated with a feature are used as training data to train a machine learning model. A variety of machine models can be used, including (but not limited to) generative adversarial networks (GANs), convolutional neural networks (CNNs), random forests, support vector machines (SVMs), and boosted decision trees. It should be understood that any appropriate machine learning model may be used as appropriate to the requirements of specific applications in accordance with a number of embodiments of the invention.

Trained computational models can be used to reveal (107) biological attributes that are associated with chromatin-derived nucleic acid sequences derived from an individual or cohort. A chromatin-derived signal profile of an individual (or group of individuals) can be inserted into a feature-associated trained model to reveal whether that profile has the signals that associate with a particular biological feature. In some embodiments, a signal profile is inserted in a number of feature-associated trained models to determine a variety of features that may be signified by the profile of an individual (or group of individuals). Accordingly, numerous embodiments can reveal a variety of biological attributes, including (but not limited to) tissue origin, cell type, signal transduction pathway activation, immune activation, tumor immune suppression and immune tumor surveillance, phenotype disposition, propensity for a disorder, and pathogenicity of a disorder. Any phenotype or disorder having a genetic and/or molecular signal signature can be revealed, including (but not limited to) oncogenic, autoimmune, cardiovascular, and neurodegenerative diseases.

Furthermore, in various embodiments, a signal profile is inserted into multi-feature and/or hierarchical trained models to reveal multilayered features associated with a signal profile. For example, a signal profile derived from an individual's cfDNA extracted from plasma may be first inserted into models to determine tissue origin, then inserted into models to determine cell type, then inserted into models to determine activation of a transcriptional pathway, then inserted into models to determine a disease condition revealing a precise phenotype/disorder (e.g., ER+/HER2+breast cancer).

Once biological attributes are revealed, various embodiments can utilize the knowledge for a number of applications, including (but not limited to) development of research tools, developing diagnostics, diagnoses of individual, and treating individuals. Accordingly, embodiments as described herein can improve diagnostics based on nucleic acid signatures, such as those that can be derived from cfDNA and cfRNA.

Development of Frequency Signal Maps

Several embodiments are directed to developing frequency signal maps using a computing system. A frequency signal map, in accordance with a multitude of embodiments, is a map that combines genomic region identity and signal strength in relation to a sequencing read profile. In many embodiments, frequency signal maps highlight various sequences that are abundant in a sample. For example, when sequencing cfNAs, sequences that are protected by association with a protein factor would be expected to be in higher frequency and thus stronger signal. Furthermore, in several embodiments, a frequency signal map highlights factors that are elevated in a certain condition. For example, a cfDNA sample derived from a patient having a particular cancer may result in a frequency sequence signal map that highlights DNA sequences that associate with factors that are elevated in that particular cancer.

Depicted in FIG. 4 is a process to develop a signature frequency signal map in accordance with an embodiment of the invention. As depicted in the figure, process 400 obtains (401) chromatin-derived nucleic acid sequences from a biological source or sequence database. In several embodiments, chromatin-derived nucleic acid sequences are sequences related to factors bound to nucleic acids. These factors can be DNA-binding proteins (e.g., transcription factors, chromatin modifiers), RNA-binding proteins, or other factors that interact with nucleic acids.

A number of methods of obtaining chromatin-derived nucleic acid sequences are described herein, such as discussed in the preceding section. Accordingly, in some embodiments, chromatin-derived nucleic acid sequences may be derived from cfNAs extracted from biological source, such as blood, plasma, lymphatic fluid, cerebral spinal fluid, urine, feces, cell cultures, organoid cultures, etc. In many embodiments, chromatin-derived nucleic acid sequences may be derived from a cellular source, such as a tissue (e.g., biopsy), exosomes, an in vitro cell line, or isolated single cells (e.g., circulating tumor cells isolated from blood), which in turn may be concentrated by a number of known methods (e.g., nuclease digestion, chromatin immunoprecipitation). In additional embodiments, chromatin-derived nucleic acid sequences are derived from publicly or privately available databases, especially epigenetic databases (e.g., ENCODE). Numerous embodiments can utilize expression datasets (e.g., RNA-seq datasets) to derive chromatin-derived nucleic acid sequence data by linking expression with an epigenetic and factor-related profile.

Process 400 trims, processes, and maps (403) sequencing data. Many methodologies are known to process sequence data, and any appropriate method can be used. For example, the sequence data can be trimmed from the publicly available Trim Galore (http://www.bioinformatics.babraham.ac.uk/projects/trim_galore/) or cutAdapt (https://code.google.com/p/cutadapt/) methods, which remove adapter sequences and trim poor-quality bases. Mapping can be performed with any appropriate annotated genome, such as, for example, UCSC's hg19 (http://support.illumina.com/sequencing/sequencing_software/igenome.html) and alignment tool, such as, for example, Bowtie2 (http://bowtie-bio.sourceforge.net/bowtie2/index.shtml). Processing of the data will be dependent on the user's goal, and thus is adaptable to the results desired. In some embodiments, sequence fragments are tagged with unique molecular identifiers (UMIs), which may help differentiate copy numbers of sequences from PCR amplification, and thus PCR duplicates can be removed from sequencing results. Although only a few methods of trimming, processing, and mapping sequence data are disclosed, it should be understood many more methods exist and would be covered by various embodiments of the invention.

Process 400 identifies (405) genomic regions and clusters sequencing signals. Given a set of sequencing data, sequencing reads can be annotated with genomic location and clustered based on that location. Frequency peaks can be identified resulting in a signal (e.g. ATAC-seq or DNase-seq fragment counts, or RNA quantifications). In some embodiments, signals are annotated with a set of features, which include (but are not limited to) tissue origin, cell type, transduction pathway activation, immune activation, phenotype disposition, propensity for a disorder, and pathogenicity of a disorder.

Clustered sequencing signals with annotated genomic regions are used in process 400 to develop (407) a frequency sequence signal map, which is a collection of signals across a whole or partial genome. In many embodiments, frequency signals identify chromatin-derived nucleic acid sequences from a particular nucleic acid source or related to a particular individual, cohort, or feature. In some embodiments, a collection of frequency signals when associated with source, individual, cohort, or feature, is a signature sequence signal map for that association. For example, in various embodiments, a feature is a cell type and a collection of frequency signals associated with a cell type is a signature signal map for that cell type (e.g., T-cell signature signal map). In a similar manner, in some embodiments, a collection of frequency signals associated with nucleic acids obtained from an individual (e.g., an individual's cfDNA) is a signature signal map for that individual's nucleic acid sample.

Process 400 has an option of performing (409) differential analysis on at least two signal maps. By comparing signals between maps, signals that are specific to one mapping can be identified. In some embodiments, differential analysis is used to identify signals that are particular to various features, source, individual, or cohort. For example, a particular individual's signal map can be differentially compared with a control reference to identify, which, if any, signals are unique. Unique signals could be related to a particularity (e.g., unique phenotype) or an abnormality (e.g., a disease) and thus could potentially provide new insights into nucleic acids examined. In an alternative example, a signal map of a cohort of individual's having a disease can be compared with a signal map of a cohort of healthy individuals to reveal signals particular to a disease. Other examples include contrasting signal maps between activated immune cells and non-activated immune cells; cell types of one origin to cell types of another origin; or oncogenic cell from healthy cell. It should be understood that differential analysis does not have be binary, but can be variadic functions, such as multivariate factor models, and thus any number of comparisons can be performed in an analysis to obtain signatures of each condition examined. Accordingly, differential analysis can be performed on numerous cell types (e.g., all immune cell types) or on a phenotype that presents on a spectrum (e.g., autism), for example.

In various embodiments, signal maps are refined using clustering techniques. In clustering, blockwise adaptive hierarchical approaches such as Weighted Gene Co-expression Network Analysis (WCGNA) can be especially useful. In alignment, the problem can be posed as maximizing correlation in cfDNA signal between regions. When performing module clustering, it is also possible to include additional regions and tissues than are used for signal maps. Including additional regions and samples grows the size of the matrix, and can allow better cluster detection and annotation. For regional cluster annotation, any annotated signal map dataset can be used to build annotations for clusters, including (but not limited to) enhancer-linked gene ontology and tissue-specific TF binding sites and Genomic Regions Enrichment Annotation Tool (GREAT; great.stanford.edu).

Process 400 also stores and/or reports (411) frequency signal maps. As is discussed herein, frequency signal maps can be used for experimental analyses and conclusions, diagnostics, treatments, and/or further computational analysis.

While specific examples of processes for developing frequency sequence signal maps are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for developing frequency sequence signal maps appropriate to the requirements of a given application can be utilized in accordance with various embodiments of the invention.

V-Plot Construction

A number of embodiments are directed to constructing and compressing V-plots using frequency sequence signal maps. In several embodiments, a V-plot is a 2-D pattern of a number sequence read fragments, wherein the fragment length is plotted against fragment position. Schematic examples of constructing V-plots are provided in FIG. 5A. In these examples, a 2-D V-Plot is plotted on top a 1-D sequence signal reads.

Figure 5A:
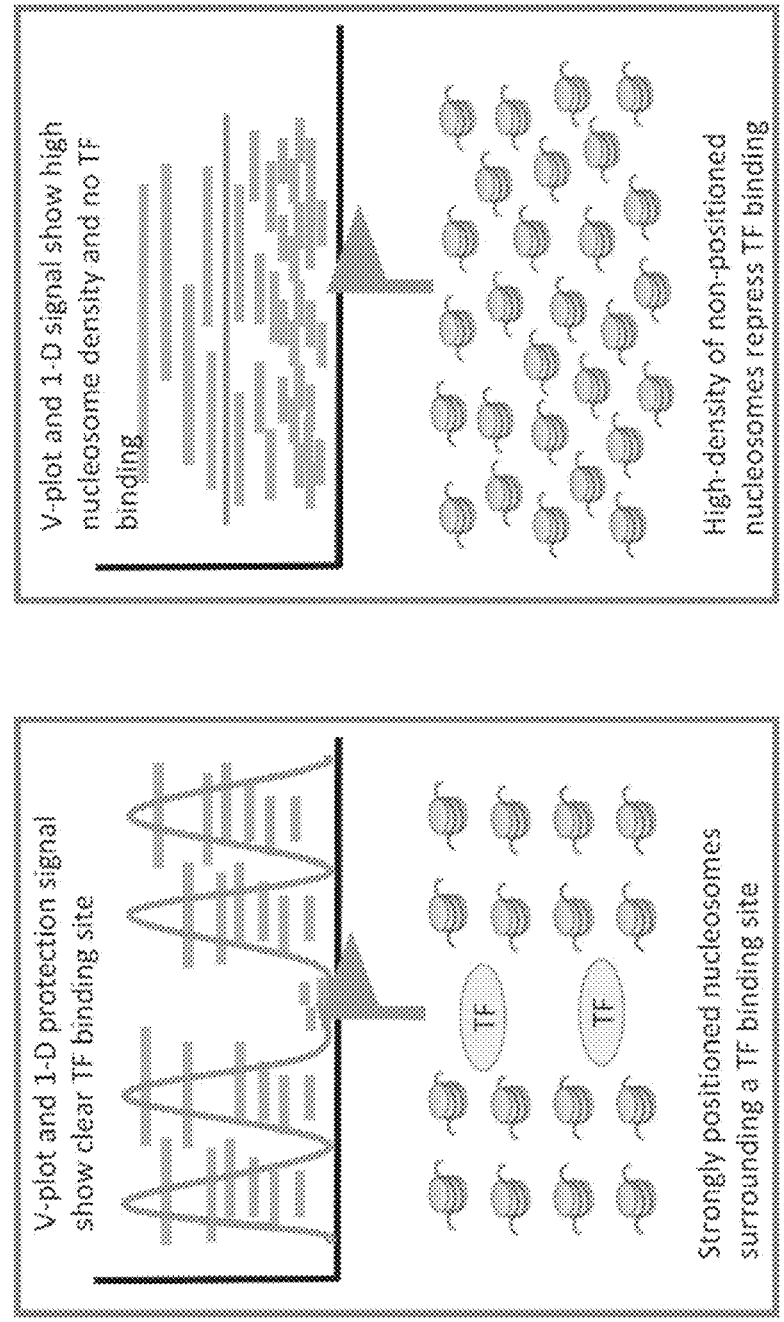
FIGS. 5A & 5B provide schematic representations of V-plots, which are generated in accordance with various embodiments of the invention.
Figure 5B:
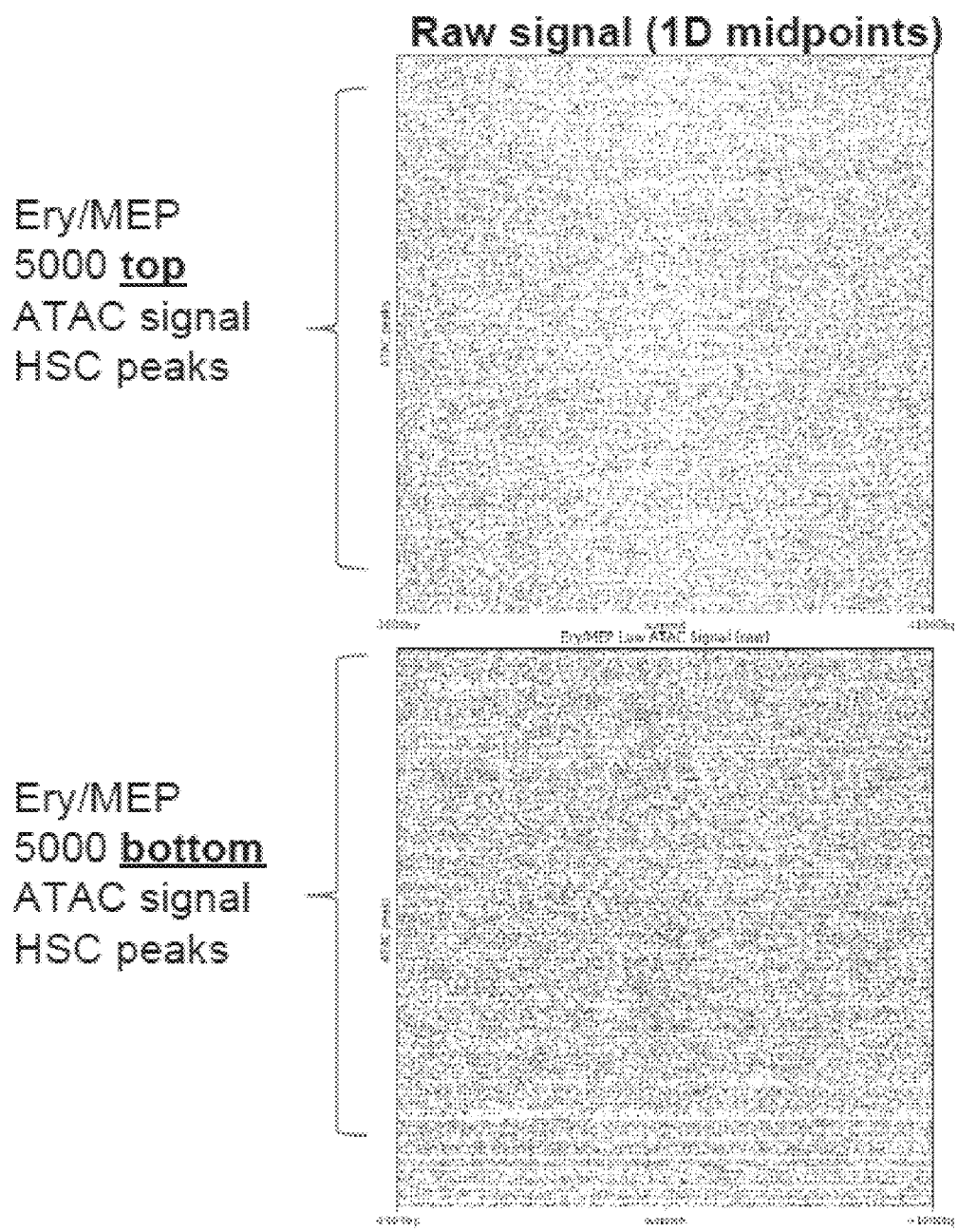
Figure 5B:
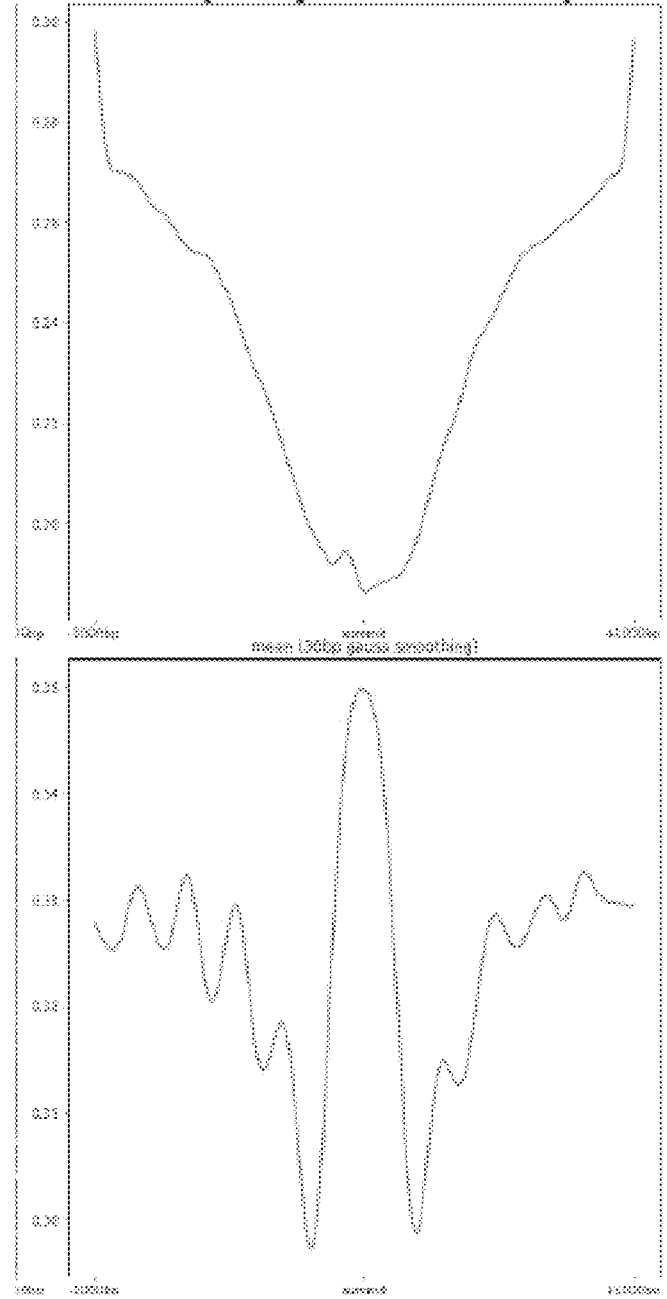

Depicted in the left panel of FIG. 5A, binding of an active transcription factor (TF) to a sequence results in a regional pattern of sequences due to the epigenetic architecture. Several shorter read fragments (approximately 100 bases) hover around the TF binding site, while several longer reads (approximately 160 bases) are spaced outward from the TF bind site, corresponding with sequences likely bound within a nucleosome. Accordingly, the sequences read fragments from the 1D plot can be used to create a signal pattern in a 2D V-plot, centering a chromatin-derived sequence at a particular genomic region. In a number of embodiments, chromatin-derived sequence signals are created for enhancers (e.g., FIG. 5B, top row) and/or repressors (e.g., FIG. 5B, bottom row). As shown in FIG. 5B, the raw signal 1-D plots (left panels) can be smoothed out into to depict a clarified signal (middle panels) and converted into a smoothed 2D V-plot (right panels).

Depicted in the right panel of FIG. 5A is a 1-D plot of high density of sequence read fragments having a length that likely correspond with nucleosomes, lacking patterned spacing. When converted into a 2-D V-plot, no specific signal is depicted due to the lack of patterned spacing of read fragment length in relation to genomic position when no factor is present. Thus, based on read fragment size, patterned spacing, and genomic locality, signals can be extracted from a chromatin-derived nucleic acid sequence data set.

Depicted in FIG. 6 is a process to construct V-plots derived from frequency signal maps in accordance with an embodiment of the invention. As depicted in the figure, process 600 obtains (601) signature frequency signal maps. Any appropriate signature signal map can be used, especially maps having signals relating chromatin-derived sequences having patterned spacing. In some embodiments, signature frequency maps are developed as shown in FIG. 4 and described in the accompanying text.

Process 600 constructs signature frequency signal maps into V-plots. In several embodiments, sequence read fragments can are mapped by their genomic location, which can be used to create a one-dimensional plot. Sequence read fragments that form a patterned alignment could indicate a signal. For instance, nucleosomes and TFs are known to have a sequence length of approximately 160 and 100 bases, respectively. Accordingly, when numerous sequence read fragments align to a particular genomic locus, it is likely due to factor-association at that location. For example, transcription factors that bind regulatory elements (e.g., enhancers, repressors) will create a patterned alignment that can be detected (see, e.g., FIG. 5B).

In many embodiments, V-plots are created by encoding sequence read fragments as indexes in a matrix. The matrix can be binarized (e.g. to remove duplicate entries) or continuous (counts are incremented for each fragment mapping to a given genomic position, fragment length pair).

Returning to FIG. 6, V-plots are optionally compressed by binning or pooling sequence read fragments. In several embodiments, the mapping between matrix coordinates and genomic coordinates/base pair length is a projection from base pair domain over a discrete multinomial range, and is adjustable. Maximal resolution is achieved, in accordance with some embodiments, when each bin is a single base pair in each direction, though bin size can be increased along either axis to reduce sparsity and/or to improve generalization error by reducing dimensionality. Resulting compressed mappings are sometimes referred to as "binned V-plots" or "maxpooled V-plots".

Various embodiments encode sequence fragments encoded as one or more coordinates in the V-plot matrix. For example, to encode positional uncertainty, in some embodiments, a fragment may be spread over multiple coordinates that can be adjacent or separated. In multiple embodiments, fragment endpoints are encoded instead of or in addition to midpoints, although this may require adjustments to filter parameterization.

In their software representation, in accordance with a number of embodiments, V-plots are stored in coordinate-major format to improve random interval access time and compression. For example, in some embodiments, a compressed column store with bitshuffle filters and dictionary run length encoding to achieve >100× compression of V-plots on disk and in memory is used, which still allows efficient data retrieval.

Process 600 also optionally reweights sequence signal V-plots based on the sequence composition (e.g., GC content) or frequency (e.g., copy number aberrations). Chromatin-derived sequencing libraries often present different GC biases. cfDNA, for example, is typically GC biased because has a high composition of DNA associated with nucleosomes, which are known to have strong GC positional bias. An issue may arise when different samples have different GC fragment biases, which may result in a sample/batch specific effect that can confound differential analyses.

To combat GC fragment biases, a method has been developed to reweight V-plots based on their GC content. In some embodiments, a reference GC distribution is calculated and\or conditioned on fragment GC proportion. A reference distribution could be obtained through any number of approaches, including (but not limited to) computational simulation, MNase datasets, and averaging multiple cfNA datasets. Given such a distribution, a mapping between a sample's empirical GC distribution and the reference GC distribution is calculated. Accordingly, a mapping results as a function of the two distributions, and re-weights samples of the empirical distribution to match the reference distribution. In many embodiments, entries are re-weighted for a sample V-plot based on the mapping function. Since V-plots are scalar valued, this amounts to re-weighting the V-plot based on the sample-specific GC bias. Re-weighted V-plots can be used in further analysis.

If copy number aberrations (CNAs) are present in a sequencing data set, copy number bias can affect sequence signal analysis. CNAs can arise when an abnormal number of copies of a particular sequence arise, which may occur, for example, in cells having aneuploidy. CNAs are often found in neoplastic cells, such as cancer. In many embodiments, a whole genome sequencing (WGS) depth-based copy number detection algorithm (e.g. IchorCNA) can be applied to a sequencing data set, and then the output copy number estimates can be used to re-weight V-plots. In several embodiments, copy number values that are abnormally high can be normalized to diploid copy number and values detected that are abnormally high can be up-sampled. In various embodiments, a generative neural network with zero inflated mixture loss can be utilized for upsampling.

Process 600 also optionally filters signature frequency sequence signal V-plots to further differentiate signals. In several embodiments, a V-plot can be reduced to a set of lower-dimensional signals using a filter bank. Such filters can be designed (e.g. a gaussian filter), or learned (e.g. an autoencoder, a wavelet projection, or a supervised learning model), or a combination of both, using a prior initialization and optimization. Various embodiments of filter banks can include multiple filters, where different filters can correspond to different fragment lengths. This separates signals for nucleosome-derived sequence fragments and shorter TF-derived sequence fragments. In a number of embodiments, filters can split a signal by frequency, e.g. using an array of bandpass filters spanning different frequency windows of signals.

Examples of designed filters to be used in accordance with various embodiments include (but are not limited to) Gaussian filters, median filters, nucleosome profile filters such as WPS filters, simulation-based filters, projection into spectral components, and bandpass array filters.

In many embodiments, learned filters can reconstruct a signal in a supervised or unsupervised manner to optimize their fit. Examples of learned filters include (but are not limited to) convolutional autoencoders, variational autoencoders (VAEs), generative adversarial neural networks (GANs), spectral decompositions including wavelet decompositions with selected frequency components, principal component analysis (PCA), and linear filters.

In several embodiments, optimization is performed with respect to reconstruction loss, variational priors, maximal divergence, or supervised objectives such as gene expression, accessibility, or other annotation prediction. Various supervised learned filters, in accordance with multiple embodiments, transform an input V-plot into a more predicted signal by genomic loci labeling, (e.g., learning TF-binding sites, nucleosome occupation sites).

In numerous embodiments, learned filters use outputs of designed/fixed filters as input. For example, VAEs and GANs can be trained from wavelet decompositions of V-plots. Such models use a wavelet transformation as input to a generative model, which learns a low-dimensional embedding. In another example, a Fourier transformation of a nucleosome occupancy correlation filter can be used as input to a VAE, which models high-order correlation in the frequency domain in a low-dimensional and interpretable latent space.

Unsupervised learning directly from V-plots can be difficult due to their sparsity. To overcome this hardship, in some embodiments, zero-inflated mixture models are used, which may provide an advantageous benefit owing to the fact they directly model the zero-inflated characteristic of the data. These models typically use a deep neural network as the factor for zero inflation.

In multiple embodiments, a smoothness prior (e.g., total variation denoising (TVD)) in learned filter objectives is used as a compound objective for gradient-based updates. This constrains the filter to learn embeddings that jointly minimize variance in the predictions with the primary optimization objective, which may lead to faster convergence and more interpretable embeddings.

In some embodiments, signal filters are used sequentially. For example, a frequency transformation with a low-pass filter to remove high frequency noise can be used to convert the output to a coordinate space, and then a density filter can be applied to extract a 1-D trace.

Process 600 also stores and/or reports (611) constructed V-plots. As is discussed herein, constructed V-plots can be used for experimental analyses and conclusions, diagnostics, treatments, and/or further computational analysis.

While specific examples of processes for constructing V-plots are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for constructing V-plots appropriate to the requirements of a given application can be utilized in accordance with various embodiments of the invention.

Signal Aggregation and Model Training

Numerous embodiments are directed to aggregating signals from V-plots and utilizing frequency signals to train machine-learning models. Depicted in FIG. 7 is an embodiment of a process to aggregate and align signals and train a computational model for a feature.

Process 700 begins by obtaining (701) sequence signal V-plots of at least one collection of chromatin-derived nucleic acid sequences. Any appropriate collection of sequence signal V-plots can be used, including a collection of V-plots that can be defined by a feature. A feature, in accordance with numerous embodiments, is a biological description that can be used to describe a collection of signals that are constructed into V-plots. For example, in some embodiments, a feature is a phenotype, a disorder, tissue origin, a cell type, physiological condition, chromatin status, or an activation of a transduction pathway. It should be understood that a collection of V-plots can be constructed for a single feature, a combination of features, or a collection of signals lacking a feature (e.g., signature profile excluding a certain cell type).

As depicted in FIG. 7, signals of V-plots are aggregated and aligned (703). Across a set of genomic regions, in accordance with various embodiments, V-plot signals can be aggregated from each of the different regions to measure their enrichment for different region sets corresponding to a feature. In several embodiments, relative scores of enrichment can be used to estimate the likelihood that an aggregation of signals represents a feature.

In many embodiments, to increase precision of signal, aggregated V-plots can be aligned to a more precise location. Positional uncertainty in region locality can induce undulations in output signal. Chromatin-derived nucleic acid signals often consist of both low-frequency (wavelength 500-2000 bp) and higher frequency nucleosome components (wavelength ~160 bp). Positional uncertainty of accessibility or TF peak calling is typically ~100 bp, which is within the wavelength of the nucleosome component and yields constructive interference in the high frequency domain, disturbing nucleosome resolution. The lack of resolution is challenging for resolving chromatin-derived signal because nucleosome positioning and TF occupancy is highly informative. To overcome this interference, in some embodiments, stochastic optimization is used on offset coordinates to maximize similarity (e.g. cosine distance, least squares, difference in numerical gradients, etc.).

Utilizing aggregated and aligned signals of frequency sequence signal V-plots, computational machine-learning models can be trained (705) to predict feature outcome. A variety of machine-learning models can be implemented, in accordance with numerous embodiments, including (but not limited to) GANs, CNNs, random forests, SVMs, and boosted decision trees. In several embodiments, a feature is a biological attribute (i.e., an attribute shared by a collection of chromatin-derived sequences used to build the set of V-plots for training). In many embodiments, a variety of features can be used in training for biological attribute prediction, including (but not limited to) a phenotype, a disorder, a tissue origin, a cell type, a physiological condition, chromatin status, or an activation of a transduction pathway.

In many embodiments, sequence signal V-plots are annotated to perform region-level and/or sample-level feature predictions. Examples region-level features include (but are not limited to) gene expression prediction, region accessibility prediction, and chromatin state annotation. Furthermore, examples of sample-level features include (but are not limited to) disease vs. healthy, disease stage, immune activation level, and treatment response level.

In a number of embodiments, machine-learning models are trained to improve signal resolution (e.g., low quality resolution to super resolution). By training generative neural networks on subsampled cfDNA data, it has been demonstrated that original higher resolution data can be predicted using a zero-inflated mixture loss. VAE and GAN models are often referred to as "super resolution" models because they infer higher coverage data from lower coverage data can, and be adapted to improve signal resolution. Additionally, domain adversarial compound objectives can be used in these generative models to overcome sample or batch specific artifacts.

It should be understood that multiple computational models can be trained concurrently or sequentially to yield multi-feature or hierarchical feature predictions in accordance with a number of embodiments. Accordingly, multiple region-level, sample-level, and/or signal resolution models and training sets can be combined to yield combinatorial feature predictions.

Process 700 also stores and/or reports (707) trained machine-learning models. As is discussed herein, trained models can be used for experimental analyses and conclusions, diagnostics, and/or further computational analysis.

While specific examples of processes for training computational models are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for training computational models appropriate to the requirements of a given application can be utilized in accordance with various embodiments of the invention.

Biological Attributes Revealed

Many embodiments are directed to processes that reveal biological attributes of an individual, a cohort, or a collection of nucleic acid sequences utilizing computational models that were trained with signal V-plots. Provided in FIG. 8 is an embodiment of a process to reveal biological attributes. Process 800 begins with obtaining (801) frequency sequence signal V-plots of at least one individual, cohort, or collection of nucleic acid sequences. Any appropriate collection frequency sequence signal V-plots can be used. In some embodiments, V-plots are constructed using a frequency signal map developed from chromatin-derived sequences. The source of chromatin-derived sequences can be any appropriate source, including cfNAs extracted from a biological source, such as blood, plasma, lymphatic fluid, cerebral spinal fluid, urine, feces, or chromatin-derived sequences derived from a biopsy or isolated single cell.

Process 800 also obtains (803) at least one trained model that has been trained to predict a feature. Any appropriate computational model can be used in accordance with a number of embodiments, such as various models described in the preceding section. In many embodiments, a model to be used is trained to predict a feature selected from a variety of biological attributes, including (but not limited to) a phenotype, a disorder, a tissue origin, a cell type, a physiological condition, chromatin status, or an activation of a transduction pathway. In some embodiments, a model predicts a region-level or sample-level feature. Examples region-level features include (but are not limited to) gene expression prediction, region accessibility prediction, and chromatin state annotation. Furthermore, examples of sample-level features include (but are not limited to) disease vs. healthy, disease stage, immune activation level, and treatment response level. Numerous embodiments of models also provide signal nucleotide resolution improvement. Furthermore, a multitude of embodiments incorporate hierarchical and/or multi-feature models.

Frequency signal V-plots are entered (805) into at least one trained model to reveal (807) biological attributes of an individual, a cohort, or a collection of nucleic acid sequences in relation to a feature that the model is trained to predict. Accordingly, in several embodiments, a phenotype, a disorder, tissue origin, a cell type, a physiological condition, and/or a transduction pathway activation is revealed, depending on which trained models are utilized. Also in some embodiments, gene expression, region accessibility, chromatin state, disease state, stage of disease, immune activation level, and treatment response are predicted.

Process 800 also stores and/or reports (809) biological attributes of an individual, a cohort, or a collection of nucleic acid sequences. As is discussed herein, biological attributes can be used for experimental analyses and conclusions, diagnostics, treatments, and/or further computational analysis.

While specific examples of processes for revealing biological attributes are described above, one of ordinary skill in the art can appreciate that various steps of the process can be performed in different orders and that certain steps may be optional according to some embodiments of the invention. As such, it should be clear that the various steps of the process could be used as appropriate to the requirements of specific applications. Furthermore, any of a variety of processes for revealing biological attributes appropriate to the requirements of a given application can be utilized in accordance with various embodiments of the invention.

Systems of Detecting Sequence Signals and Revealing Biological Attributes

Figure 9:
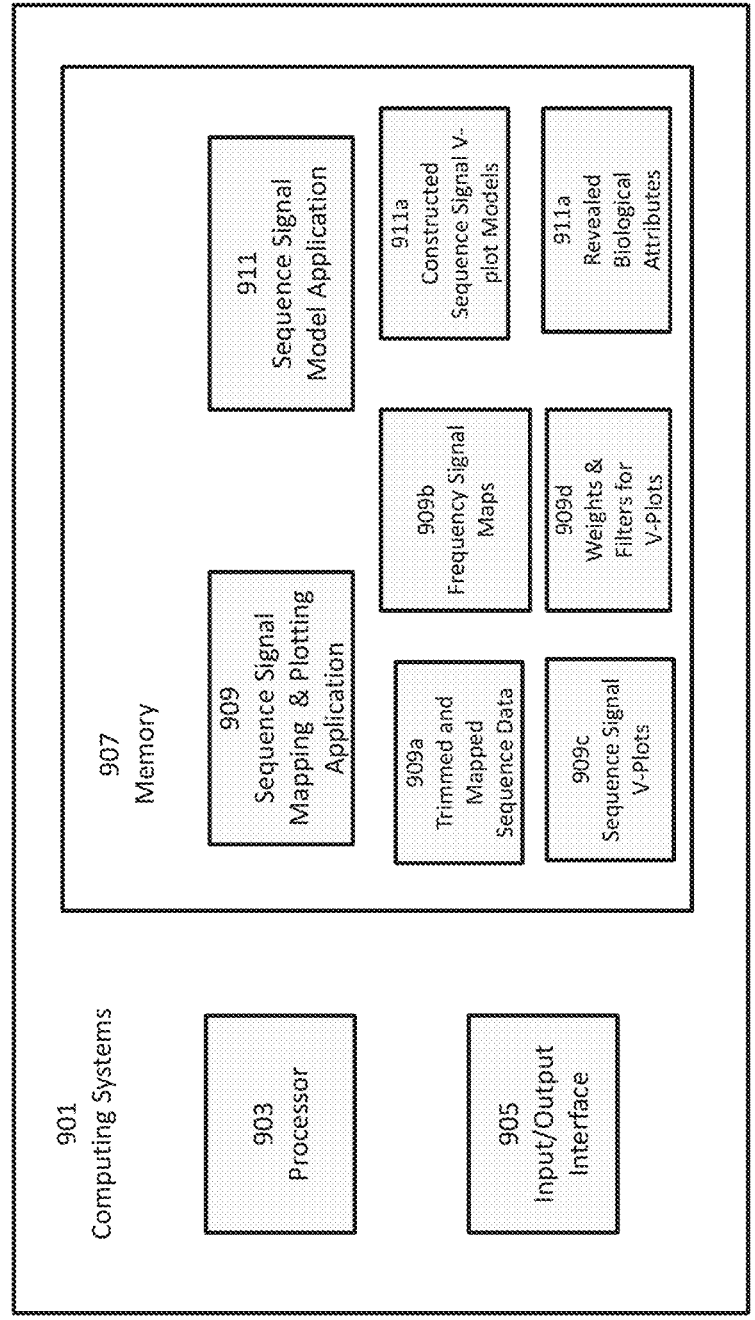
FIG. 9 provides a schematic diagram of computing systems in accordance with various embodiments of the invention.

Turning now to FIG. 9, computing systems (901) may be implemented on a single or a plurality of computing device (s) in accordance with some embodiments of the invention. Computing systems (901) may be a personal computer, a laptop computer, any other computing device with sufficient processing power, or any plurality and/or combination of computing devices for the processes described herein. Computing systems (901) include a processor (903), which may refer to one or more devices within the computing systems (901) that can be configured to perform computations via machine readable instructions stored within a memory (907) of the computer system (901). The processor may include one or more microprocessors (CPUs), one or more graphics processing units (GPUs), and/or one or more digital signal processors (DSPs).

In a number of embodiments of the invention, the memory (907) may contain a sequence signal mapping and plotting application (909) and sequence signal model application (911) that performs all or a portion of various methods according to different embodiments of the invention described throughout the present application. As an example, processor (903) may perform a process to develop frequency signal maps similar to any of the processes described above with reference to FIG. 4 and a process to reveal biological attributes similar to any of the processes described above with reference to FIG. 8, during which memory (907) may be used to store various intermediate processing data such as trimmed and mapped sequence data (909*a*), frequency signal maps (909*b*), sequence signal V-plots (909*c*), weights and filters for V-plots (909*d*), constructed sequence signal V-plot models (911*a*), and revealed biological attributes (711*b*).

In some embodiments of the invention, the computer system (901) may include an input/output interface (905) that can be utilized to communicate with a variety of devices, including but not limited to other computing systems, a projector, and/or other display devices. As can be readily appreciated, a variety of software architectures can be utilized to implement a computer system as appropriate to the requirements of specific applications in accordance with various embodiments of the invention.

Although computer systems and processes for detecting sequence signals and revealing biological attributes and performing actions based thereon are described above with respect to FIG. 9, any of a variety of devices and processes for data associated with detecting sequence signals and revealing biological attributes as appropriate to the requirements of a specific application can be utilized in accordance with many embodiments of the invention.

Applications of Revealing Biological Attributes

Various embodiments are directed towards utilizing a revealed biological attributes. In some embodiments, a biological attribute is a phenotype, a disorder, a tissue origin, a cell type, a physiological condition, chromatin status, or an activation of a transduction pathway. In some embodiments, a model also predicts a region-level or sample-level knowledge, which can also be used in downstream applications. Examples region-level features include (but are not limited to) gene expression prediction, region accessibility prediction, and chromatin state annotation. Furthermore, examples of sample-level features include (but are not limited to) disease vs. healthy, disease stage, immune activation level, immune proliferation, immune cell type composition, immune cell epigenetic state, and treatment response level. These revelations can be further utilized in an experimental or clinical setting.

Determining Tissue of Origin and Chromatin

In several methods as described herein a tissue of origin and/or cell type of the starting nucleic acid material can be determined. This is especially useful when the tissue of origin and/or cell type of the starting nucleic acid material is not known, such as (for example) when utilizing extracellular nucleic acids (e.g., cfDNA) from blood, serum, cerebrospinal fluid, lymph fluid, urine and feces. Accordingly, in a number of embodiments, nucleic acids are extracted having unknown origin and chromatin status and then processed to determined their origin and chromatin status. This process is especially useful in a clinical setting to provide a diagnostic scan.

An exemplary procedure for a diagnostic scan of an individual is as follows:

(a) extract extracellular nucleic acids
(b) determine chromatin-related nucleic acid signals
(c) determine a phenotype, a disorder, tissue origin, a cell type, chromatin status, and/or an activation of a transduction pathway from chromatin-related nucleic acid signal, which in turn indicates a clinical status such as pathological status of a disorder, activation of the immune system, neoplasia, inflammation, placental disorder, tissue damage, and neurodegeneration Typically, when performing a diagnostic scan of a healthy individual, most extracellular nucleic acids in blood is provided by non-solid tissue (i.e., hematopoietic and lymphocytic tissue) and thus the major chromatin-related nucleic acid signals are derived from these tissues. Other sources of material (e.g., serum, cerebrospinal fluid, lymph fluid, urine, feces) will have a set of predominant chromatin-related nucleic acid signals as well. In various cases of disease and/or disorder, the affected tissue will release nucleic acids into a source material (e.g., blood), which can be detected by various methods as described herein.

Detection of abnormal origins of nucleic acids has several inferences that result in clinical action to be taken, such as further diagnostic tests and/or treatments. For instance, detection of abnormal nucleic acids could infer inflammation, toxicity, neoplasia, or some other ailment that results in the release of extracellular nucleic acids. Accordingly, in several embodiments, a diagnostic scan detects disorders involving inflammation, toxicity, and cancer including, (but not limited to) various neoplasms including cancer, placental disorders, tissue damage (e.g., cirrhosis), neural toxicity (e.g., neurodegeneration), and inflammatory diseases (e.g., autoimmune disease). In many embodiments, follow-up diagnostic test or a treatment of the disorder is performed on the basis of the diagnostic scan.

In a similar manner, detection of abnormal epigenetic status has several inferences that result in clinical action to be taken, such as further diagnostic tests and/or treatments. For instance, detection of abnormal epigenetic status could infer disease-associated activation, immune activation, or neoplastic growth. Accordingly, in several embodiments, a diagnostic scan detects pathological status of disease, activation of the immune system, or neoplasia. In many embodiments, follow-up diagnostic test or a treatment is performed on the basis of the diagnostic scan.

Cancer Diagnostics and Treatments

A number of embodiments are directed towards performing a diagnostic scan on extracellular DNA of an individual and then based on results of the scan indicating neoplastic tissue, performing further diagnostic tests and/or treating the individual.

Neoplasms are typically characterized by accelerated growth and an open chromatin status. Accelerated growth also causes necrosis of neoplastic cells and stimulation of the immune system. Accordingly, neoplasms including cancer release a substantial amount of extracellular nucleic acids that can be detected by various methods as described herein. When a diagnostic scan detects solid tissue nucleic acids (i.e., tissue not typically detected in a scan of healthy individual), chromatin architecture characteristic of neoplastic cells, and/or activation of tumor surveillance via immune response, it indicates that a neoplasm exists, and often in a particular tissue detected. Based on this indication, a further diagnostic test or a treatment may be performed on the individual.

In accordance with various embodiments, numerous types of neoplasms can be detected, including (but not limited to) acute lymphoblastic leukemia (ALL), acute myeloid leukemia (AML), anal cancer, astrocytomas, basal cell carcinoma, bile duct cancer, bladder cancer, breast cancer, cervical cancer, chronic lymphocytic leukemia (CLL) chronic myelogenous leukemia (CML), chronic myeloproliferative neoplasms, colorectal cancer, endometrial cancer, ependymoma, esophageal cancer, esthesioneuroblastoma, Ewing sarcoma, fallopian tube cancer, gallbladder cancer, gastric cancer, gastrointestinal carcinoid tumor, hairy cell leukemia, hepatocellular cancer, Hodgkin lymphoma, hypopharyngeal cancer, Kaposi sarcoma, Kidney cancer, Langerhans cell histiocytosis, laryngeal cancer, leukemia, liver cancer, lung cancer, lymphoma, melanoma, Merkel cell cancer, mesothelioma, mouth cancer, neuroblastoma, non-Hodgkin lymphoma, non-small cell lung cancer, osteosarcoma, ovarian cancer, pancreatic cancer, pancreatic neuroendocrine tumors, pharyngeal cancer, pituitary tumor, prostate cancer, rectal cancer, renal cell cancer, retinoblastoma, skin cancer, small cell lung cancer, small intestine cancer, squamous neck cancer, T-cell lymphoma, testicular cancer, thymoma, thyroid cancer, uterine cancer, vaginal cancer, and vascular tumors.

In some embodiments, a diagnostic scan as described herein provides early cancer detection. In some embodiments, a diagnostic scan is specifically directed to check for certain types of cancerous tissue detection, especially when an individual has a familial history of cancer or has a susceptibility to a particular cancer.

In accordance with several embodiments, once a diagnosis of neoplastic growth is indicated, a number of follow-up diagnostic procedures can be performed, including (but not limited to) physical exam, medical imaging, mammography, endoscopy, stool sampling, pap test, alpha-fetoprotein blood test, CA-125 test, prostate-specific antigen (PSA) test, biopsy extraction, bone marrow aspiration, and tumor marker detection tests. Medical imaging includes (but is not limited to) X-ray, magnetic resonance imaging (MRI), computed tomography (CT), ultrasound, and positron emission tomography (PET). Endoscopy includes (but is not limited to) bronchoscopy, colonoscopy, colposcopy, cystoscopy, esophagoscopy, gastroscopy, laparoscopy, neuroendoscopy, proctoscopy, and sigmoidoscopy.

In accordance with many embodiments, once a diagnosis of neoplastic growth is indicated, a number of treatments can be performed, including (but not limited to) surgery, chemotherapy, radiation therapy, immunotherapy, targeted therapy, hormone therapy, stem cell transplant, and blood transfusion. In some embodiments, an anti-cancer and/or chemotherapeutic agent is administered, including (but not limited to) alkylating agents, platinum agents, taxanes, vinca agents, anti-estrogen drugs, aromatase inhibitors, ovarian suppression agents, endocrine/hormonal agents, bisphosphonate therapy agents and targeted biological therapy agents. Medications include (but are not limited to) cyclophosphamide, fluorouracil (or 5-fluorouracil or 5-FU), methotrexate, thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolomide, topotecan, vincristine, vinblastine, eribulin, mutamycin, capecitabine, capecitabine, anastrozole, exemestane, letrozole, leuprolide, abarelix, buserelin, goserelin, megestrol acetate, risedronate, pamidronate, ibandronate, alendronate, zoledronate, tykerb, daunorubicin, doxorubicin, epirubicin, idarubicin, valrubicin mitoxantrone, bevacizumab, cetuximab, ipilimumab, ado-trastuzumab emtansine, afatinib, aldesleukin, alectinib, alemtuzumab, atezolizumab, avelumab, axitinib, belimumab, belinostat, bevacizumab, blinatumomab, bortezomib, bosutinib, brentuximab vedotin, brigatinib, cabozantinib, canakinumab, carfilzomib, ceritinib, cetuximab, cobimetinib, crizotinib, dabrafenib, daratumumab, dasatinib, denosumab, dinutuximab, durvalumab, elotuzumab, enasidenib, erlotinib, everolimus, gefitinib, ibritumomab tiuxetan, ibrutinib, idelalisib, imatinib, ipilimumab, ixazomib, lapatinib, lenvatinib, midostaurin, necitumumab, neratinib, nilotinib, niraparib, nivolumab, obinutuzumab, ofatumumab, olaparib, olaratumab, osimertinib, palbociclib, panitumumab, panobinostat, pembrolizumab, pertuzumab, ponatinib, ramucirumab, regorafenib, ribociclib, rituximab, romidepsin, rucaparib, ruxolitinib, siltuximab, sipuleucel-T, sonidegib, sorafenib, temsirolimus, tocilizumab, tofacitinib, tositumomab, trametinib, trastuzumab, vandetanib, vemurafenib, venetoclax, vismodegib, vorinostat, and zivafliber-cept. In accordance with various embodiments, an individual may be treated, by a single medication or a combination of medications described herein. A common treatment combination is cyclophosphamide, methotrexate, and 5-fluorouracil (CMF).

Many embodiments are directed to diagnostic or companion diagnostic scans performed during cancer treatment of an individual. When performing diagnostic scans during treatment, the ability of agent to treat the neoplastic growth can be monitored. Most anti-cancer therapeutic agents result in death and necrosis of neoplastic cells, which should release higher amounts nucleic acids from these cells into the samples being tested. Accordingly, the level of neoplastic nucleic acids can be monitored over time, as the level should increase during treatments and begin to decrease as the number of neoplastic cells are decreased. In addition, some embodiments utilize diagnostic scans to determine the amount of nucleic acids derived from off-target healthy cells as an indication of off-target effects of the treatment. In some embodiments, treatments are adjusted based on the treatment effect on neoplastic and healthy cells. For instance, if the treatment isn't cytotoxic to neoplastic cells, a dosage amount may be increased or an agent with higher cytotoxicity can be administered. In the alternative, if a high level of off-target cytotoxicity is detected, a dosage amount can be decreased or an agent with lower cytotoxicity can be administered.

Various embodiments are also directed to diagnostic scans performed after treatment of an individual to detect residual disease and/or recurrence of neoplastic growth. If a diagnostic scan indicates residual and/or recurrence of neoplastic growth, further diagnostic tests and/or treatments may be performed as described herein. If the neoplastic growth and/or individual is susceptible to recurrence, diagnostic scans can be performed frequently to monitor any potential relapse.

Placental Disorders Diagnostics and Treatments

A number of embodiments are directed towards performing a diagnostic scan on extracellular DNA of an individual and then based on results of the scan indicating a placental disorder, performing further diagnostic tests and/or treating the individual.

A placental disorder is a disorder of the placenta during pregnancy, typically characterized by damage to the placenta that often leads to premature birth. Due to the damage of the placental tissue, a substantial amount of extracellular nucleic acids are released, which can be detected by various methods as described herein. When a diagnostic scan detects placental tissue nucleic acids, chromatin architecture characteristic of damaged tissue, and/or activation of an inflammatory immune response, it indicates a placental disorder. Based on this indication, a further diagnostic test or a treatment may be performed on the individual.

In accordance with various embodiments, numerous types of placental disorders can be detected, including (but not limited to) placental abruption, placenta accrete, placenta increta, placenta percreta, chorioamnionitis, intervillositis, TORCH infections, cytomegalovirus infection, chronic deciduitis, circumvallate placenta, placenta previa, vasa previa, chorangioma, placental infarction, choriocarcinoma, and hydatidiform mole.

In some embodiments, a diagnostic scan as described herein provides early detection of placental disorders. In some embodiments, a diagnostic scan is performed during gestational medical checkups.

In accordance with several embodiments, once a diagnosis of a placental disorder is indicated, a number of follow-up diagnostic procedures can be performed, including (but not limited to) physical exam, medical imaging, and blood tests. Medical imaging includes (but is not limited to) X-ray, magnetic resonance imaging (MRI), computed tomography (CT), ultrasound, and positron emission tomography (PET).

In accordance with many embodiments, once a diagnosis of inflammation and/or tissue damage is indicated, a number of treatments can be performed, including (but not limited to) surgery (e.g., Cesarean section), anti-inflammatories, antibiotics, antivirals, intravenous fluids, and pain reliever.

In some embodiments, a therapeutic agent is administered, including (but not limited to) ampicillin, sulbactam, penicillin, ganciclovir, valganciclovir, tocolytics, and chemotherapy.

Various embodiments are also directed to diagnostic scans performed during and/or after treatment of an individual to detect residual placental disorders. If a diagnostic scan indicates residual placental disorders, further diagnostic tests and/or treatments may be performed as described herein. Diagnostic scans can be performed frequently to monitor any potential relapse during pregnancy.

Inflammation and Tissue Damage Diagnostics and Treatments

A number of embodiments are directed towards performing a diagnostic scan on extracellular DNA of an individual and then based on results of the scan indicating inflammation and/or tissue damage, performing further diagnostic tests and/or treating the individual.

Tissue damage is typically characterized by high level of necrosis and inflammation. Accordingly, tissues that are damaged release a substantial amount of extracellular nucleic acids that can be detected by various methods as described herein. When a diagnostic scan detects solid tissue nucleic acids (i.e., tissue not typically detected in a scan of healthy individual), chromatin architecture characteristic of damaged tissue, and/or activation of an inflammatory immune response, it indicates that a tissue is damaged, and often in a particular tissue detected. Based on this indication, a further diagnostic test or a treatment may be performed on the individual.

In accordance with various embodiments, numerous types of tissue damage can be detected, including (but not limited to) appendicitis, colitis, Crohn's disease, cystitis, endocarditis, gastritis, hepatitis including cirrhosis, inflammatory bowel disease, myocarditis, neuritis, pancreatitis, pericarditis, and pneumonitis.

In some embodiments, a diagnostic scan as described herein provides early detection of inflammation and/or tissue damage. In some embodiments, a diagnostic scan is specifically directed to check for certain types of tissue damage, especially when an individual has a susceptibility to a particular type of inflammation and/or tissue damage (e.g., an individual with a history of high alcohol consumption and liver damage).

In accordance with several embodiments, once a diagnosis of inflammation and/or tissue damage is indicated, a number of follow-up diagnostic procedures can be performed, including (but not limited to) physical exam, medical imaging, biopsy extraction, endoscopy, echocardiogram, electrocardiogram, pulmonary function tests, and blood tests. Medical imaging includes (but is not limited to) X-ray, magnetic resonance imaging (MRI), computed tomography (CT), ultrasound, and positron emission tomography (PET). Endoscopy includes (but is not limited to) bronchoscopy, colonoscopy, colposcopy, cystoscopy, esophagoscopy, gastroscopy, laparoscopy, neuroendoscopy, proctoscopy, and sigmoidoscopy.

In accordance with many embodiments, once a diagnosis of inflammation and/or tissue damage is indicated, a number of treatments can be performed, including (but not limited to) surgery, anti-inflammatories, antibiotics, antivirals, intravenous fluids, and pain reliever. In some embodiments, a therapeutic agent is administered, including (but not limited to) 5-aminosalicylates, corticosteroids, colchicine, azathioprine, cyclosporine, infliximab, adalimumab, golimumab, vedolizumab, mercaptopurine, methotrexate, natalizumab, ustekinumab, antacids, acid blockers, proton pump inhibitors, ACE inhibitors, angiotensin II receptor blockers, beta blockers, and diuretics.

Various embodiments are also directed to diagnostic scans performed during and/or after treatment of an individual to detect residual inflammation and/or tissue damage. If a diagnostic scan indicates residual inflammation and/or tissue damage, further diagnostic tests and/or treatments may be performed as described herein. If the individual is susceptible to recurrence of inflammation and/or tissue damage, diagnostic scans can be performed frequently to monitor any potential relapse.

Neurodegeneration Diagnostics and Treatments

A number of embodiments are directed towards performing a diagnostic scan on extracellular DNA of an individual and then based on results of the scan indicating neurodegeneration, performing further diagnostic tests and/or treating the individual.

Neurodegeneration is typically characterized by high level of necrosis and cell death in the nervous system. Accordingly, tissues that are damaged release a substantial amount of extracellular nucleic acids, especially in cerebrospinal fluids, that can be detected by various methods as described herein. When a diagnostic scan detects abnormal nucleic acids (i.e., tissue not typically detected in a scan of healthy individual), and/or chromatin architecture characteristic of neurodegeneration, it indicates that neurological tissue is damaged. Based on this indication, a further diagnostic test or a treatment may be performed on the individual.

In accordance with various embodiments, numerous types of tissue damage can be detected, including (but not limited to) Alzheimer's disease, amyotrophic lateral sclerosis (ALS), dementia, Huntington's disease, and Parkinson's disease.

In some embodiments, a diagnostic scan as described herein provides early detection of neurodegeneration. In some embodiments, a diagnostic scan is specifically directed to check for certain types of tissue damage, especially neurological tissue.

In accordance with several embodiments, once a diagnosis of neurodegeneration is indicated, a number of follow-up diagnostic procedures can be performed, including (but not limited to) physical exam, medical imaging, biopsy extraction (e.g., spinal tap), neurological tests, electrodiagnostic tests, memory tests, genetic tests, and blood tests. Medical imaging includes (but is not limited to) X-ray, magnetic resonance imaging (MRI), computed tomography (CT), ultrasound, and positron emission tomography (PET).

In accordance with many embodiments, once a diagnosis of neurodegeneration is indicated, a number of treatments can be performed, including (but not limited to) surgery, anti-inflammatories, antibiotics, antivirals, intravenous fluids, and pain reliever. In some embodiments, a therapeutic agent is administered, including (but not limited to) cholinesterase inhibitors, memantine, riluzole, edaravone, tetrabenazine, antipsychotic drugs, carbidopa-levodopa, dopamine agonists, and MAO B inhibitors.

Various embodiments are also directed to diagnostic scans performed during and/or after treatment of an individual to detect neurodegeneration progress. If a diagnostic scan indicates continual neural tissue degeneration, further diagnostic tests and/or treatments may be performed as described herein.

EXEMPLARY EMBODIMENTS

The embodiments of the invention will be better understood with the several examples provided within. Many exemplary results of processes to develop sequence signal maps, construct V-plots, train computational models, and reveal biological attributes are provided.

Example 1: Fold-Change Signal Signature Map

Figure 10:
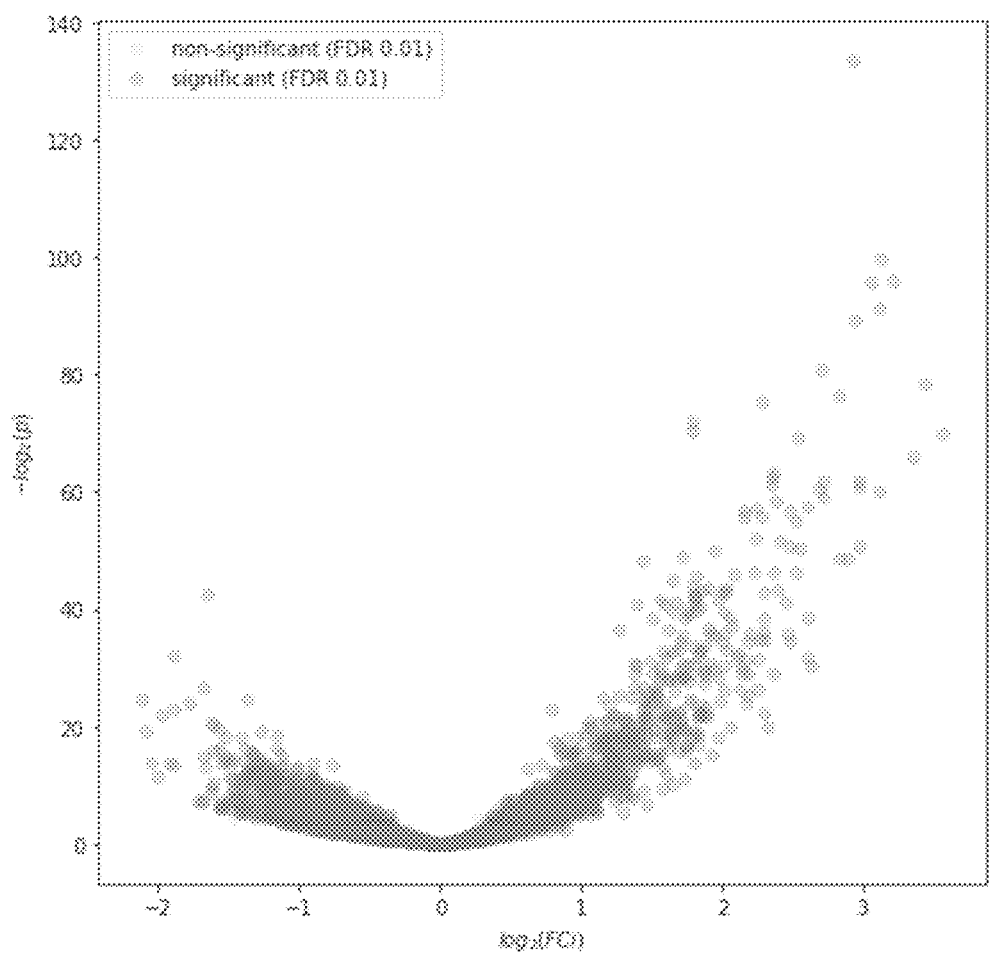
FIGS. 10 & 11 provide exemplary sequence signal maps, generated in accordance with various embodiments of the invention.

FIG. 10 is a signal signature map depicting a number of differential signals relating to a fold change of breast tissue to a control (i.e., non-breast tissue) at a number of genomic regions. Plotted on the x-axis is the fold change of a condition ($FC_i$) against significance of the change (p) on the y-axis. Each data point represents a differential signal peak at a genomic region. Accordingly, data points on the left side of the graph (i.e., $\log_2(FC_i)<0$) represent genomic region signals that are less active and data points on right side of the graph (i.e., $\log_2(FC_i)>0$) represent genomic region signals that are more active in the condition related to the control. It should be understood that signal activity refers to a read fragment frequency at a particular genomic region, and should not be confused with genetic enhancers and repressors. Accordingly, a highly active signal may arise from any chromatin-derived sequence, including sequences that are associated with genetic enhancers as well as genetic repressors.

Setting a particular threshold for significance, (e.g., Q<0.05 (where Q is a family-wise FDR correction of P) or top 1000 significant regions), significant signals at genomic regions can be used in further downstream applications. For example, the most significant genomic regions can be experimentally examined by a number of hypotheses. In addition, significant genomic regions can be used in a number of processes to construct V-plots, including within various embodiments as described herein. In some instances, it is desirable to use all significant regional peak signals. In other instances, it may be preferred to use only highly active regional peak samples when signal dilution may occur. The use of highly active signals may be particularly useful, for example, when trying to detect signature early-stage cancer signals in cfNAs extracted from a biological source like plasma, where cancer signals may be diluted within the abundance of signals that originate from circulatory blood tissue. Thus, it may be easier to detect highly active signals as they may be more prominent in a particular sample.

Example 2: Beta Value Signal Map

Figure 11:
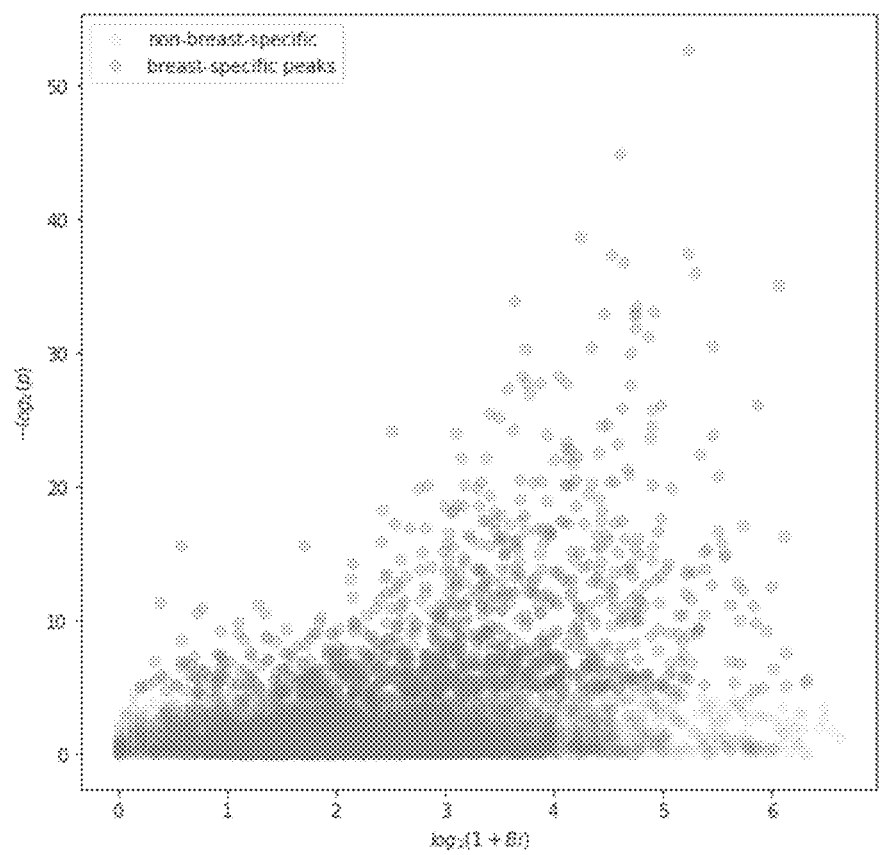

FIG. 11 is a signal signature map depicting a number of differential signals relating to a beta value of a feature compared to a control. Depicted in this data plot are signals related to the feature of breast tissue origin and a control. Plotted on the x-axis is the beta value of a feature (B1) against significance of feature signal (p) on the y-axis. Each data point represents a differential signal peak at a genomic region. Accordingly, data points greater than particular threshold (e.g., Q<0.05 (where Q is a family-wise FDR correction of P)) represent signals that are representative of the breast tissue.

The signals plotted in FIG. 11 are epigenetic signals of healthy breast tissue derived from the ENCODE database. In many instances, healthy tissue signals may be indicative of certain disorders or diseases when a rise of tissue origin signals is present. For example, cfNAs derived from plasma typically have a high abundance of signals derived from circulatory blood tissue but a low abundance of signals from other tissues (e.g., breast). When signals of a particular tissue are increased in sample compared to normal range, it could indicate a number of conditions, including (but not limited to) neoplastic tissue growth, malignancy, and/or irregular hormone/tissue signaling. Accordingly, detection of aberrant tissue origin in an individual's biological sample is used to screen and/or diagnose that individual.

Example 3: Weighting Sequence Signals Based on GC Content

Figure 12:
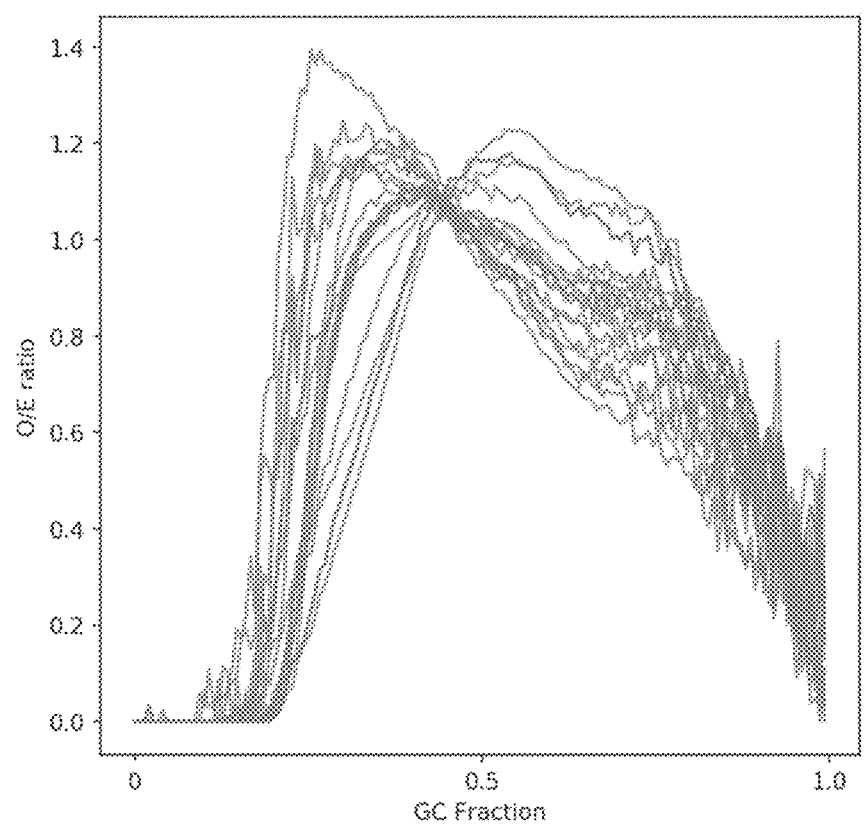
FIGS. 12 & 13 provide data charts depicting variation of GC content of various cell-free DNA libraries, generated in accordance with various embodiments of the invention.

As described herein, sequence signal V-plots can be reweighted in relation to GC content. Samples having disproportionate GC content may arise during various stop of sample preparation, such as library preparation. Depicted in FIG. 12 is a data graph revealing GC content of a number of prepared sequence libraries. On the X-axis is GC fraction of read plotted against the observed/expected ratio of GC content. Each line represents a library of cfDNA sample. As can be seen, there is a wide variance between the libraries, which could confound signal results.

Figure 13:
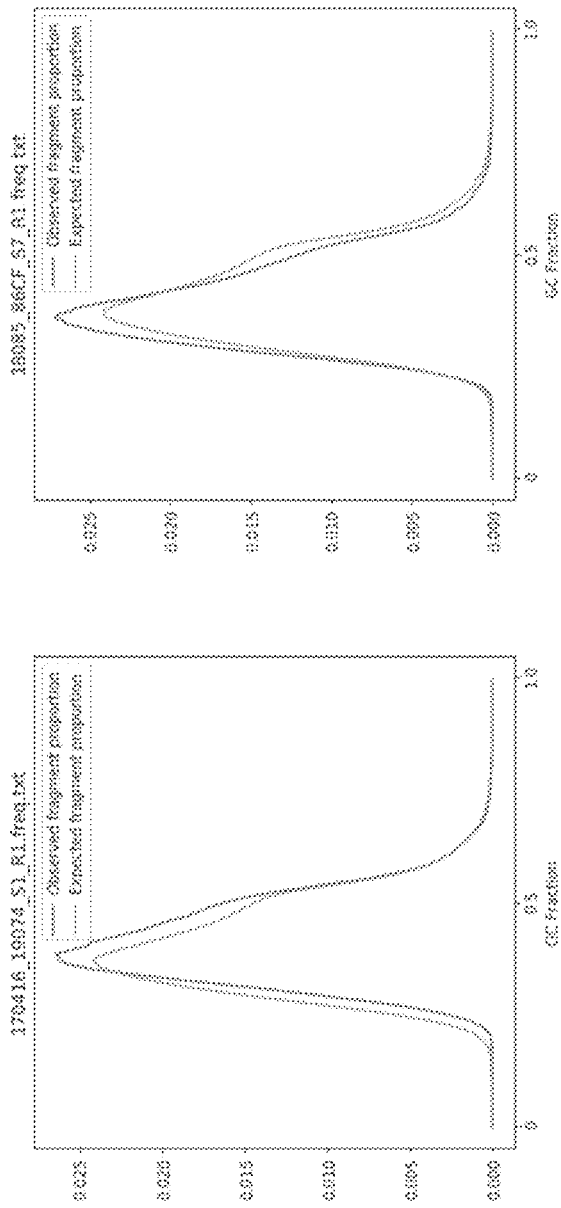

Depicted in FIG. 13 are two individually prepared sequence libraries, each of which has an observed GC fraction that deviates from the expected GC fraction. Based on these data sets, in some instances when GC content of libraries are varied, it may be beneficial to reweight V-plots to mitigate confounding of sequence signals.

Example 4: Fourier Transformation of Sequence Signal

Figure 14:
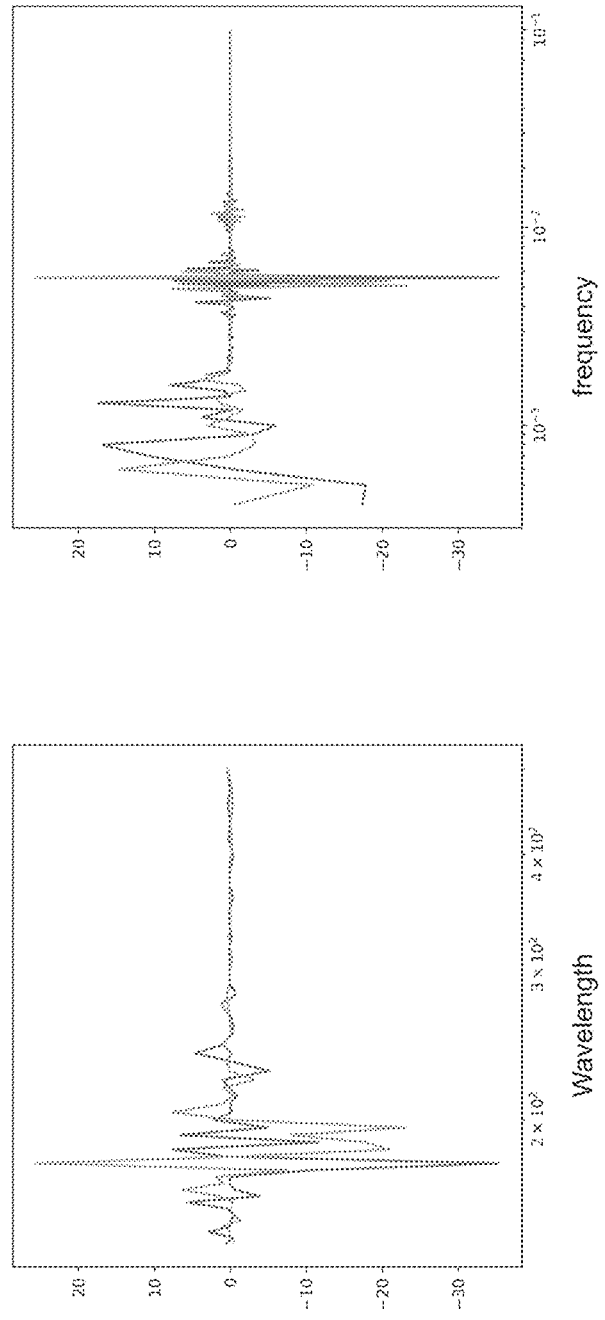
FIG. 14 provides data charts depicting the results of filtering V-plots with a Fourier transform filter, generated in accordance with various embodiments of the invention.

Depicted in FIG. 14 are examples of Fourier transformations of signals derived from a cfDNA sample. Because wavelength of sequence signal is periodic (e.g., see sine-like waves in FIGS. 5A & 5B), sequence signal can be transformed by a Fourier transformation filters. The Fourier transformation filters reveal that the dominant wavelength of the signal is approximately 100-200 bp (FIG. 14, left panel), which corresponds to the expected sequence length of the dominant species of nucleosome-associated DNA in cell-free samples. The frequency of this exemplary signal is depicted in the right panel of FIG. 14.

Example 5: Prediction of Sequence Signal Source Based on Gene Expression

Figure 15:
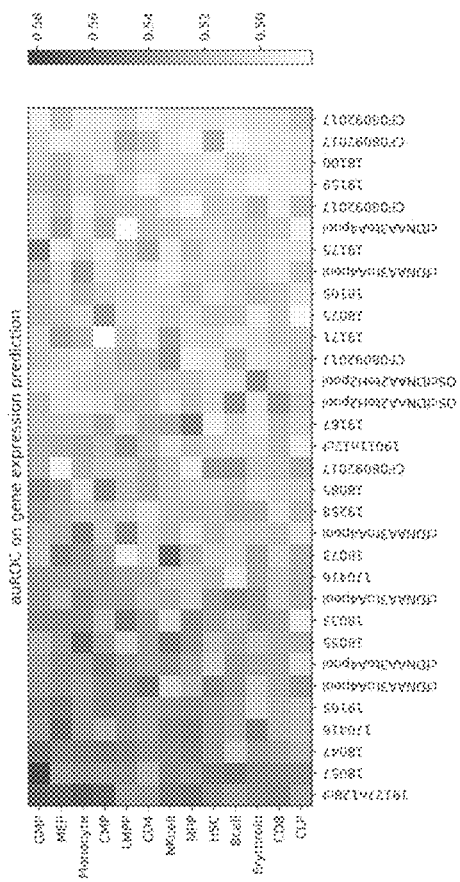
FIG. 15 provides a heat map of area under receiver operating characteristic curves for gene expression prediction, generated in accordance with various embodiments of the invention.

Depicted in FIG. 15 is an area under Receiver Operating Characteristic (auROC) heat map showing the predictive ability of trained models to predict the cell-type source (y-axis) of signals of a number of cfDNA samples (x-axis). To create this auROC heat map, a sequential training process was used to train three machine-learning models. First, a model was trained to predict from that filtered signal a promoter for every gene in the genome. Those results were trained on a model to determine whether every gene in the genome was expressed or not expressed. Then, based on those results, a model was trained to determine whether that expression profile was derived from a particular cell type, by training whether each gene was expressed or not in each cell type (e.g., expressed in GMP cells). These results were then used to determine accuracy of prediction, which is plotted heat map depicted in FIG. 15.

Example 6: Filtered and Compressed V-Plots to Detect Autoimmune Disorders

Figure 16:
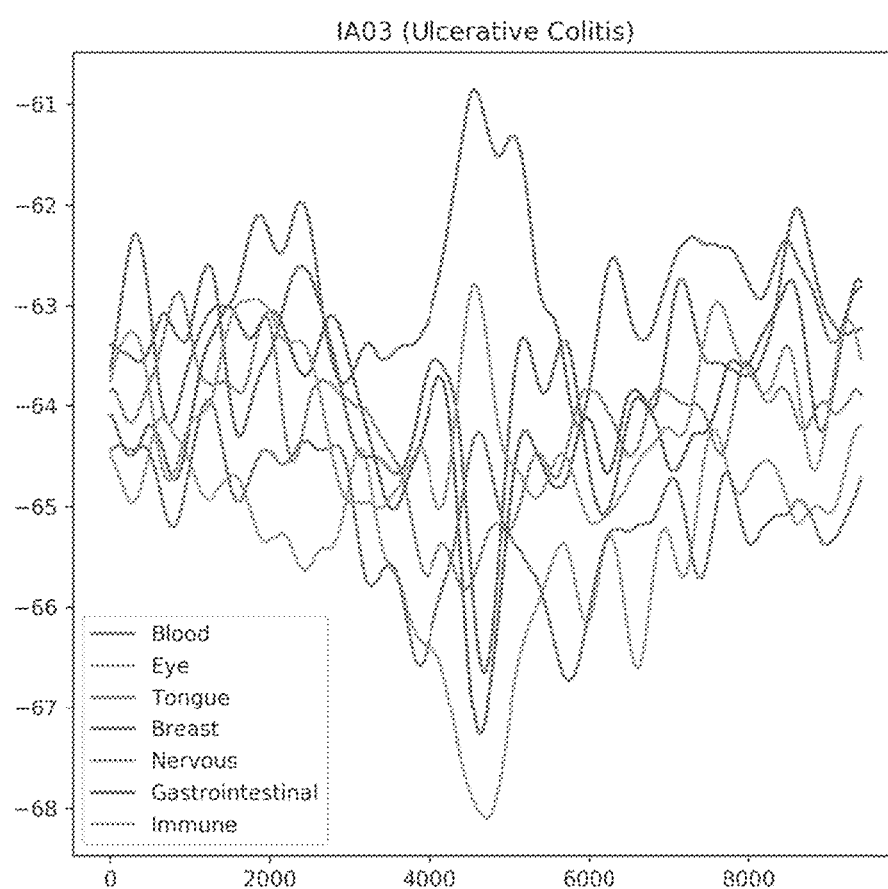
FIGS. 16 & 17 provide exemplary filtered and compressed V-plots of cell-free DNA samples derived from individuals having an autoimmune disorder, generated in accordance with various embodiments of the invention.
Figure 17:
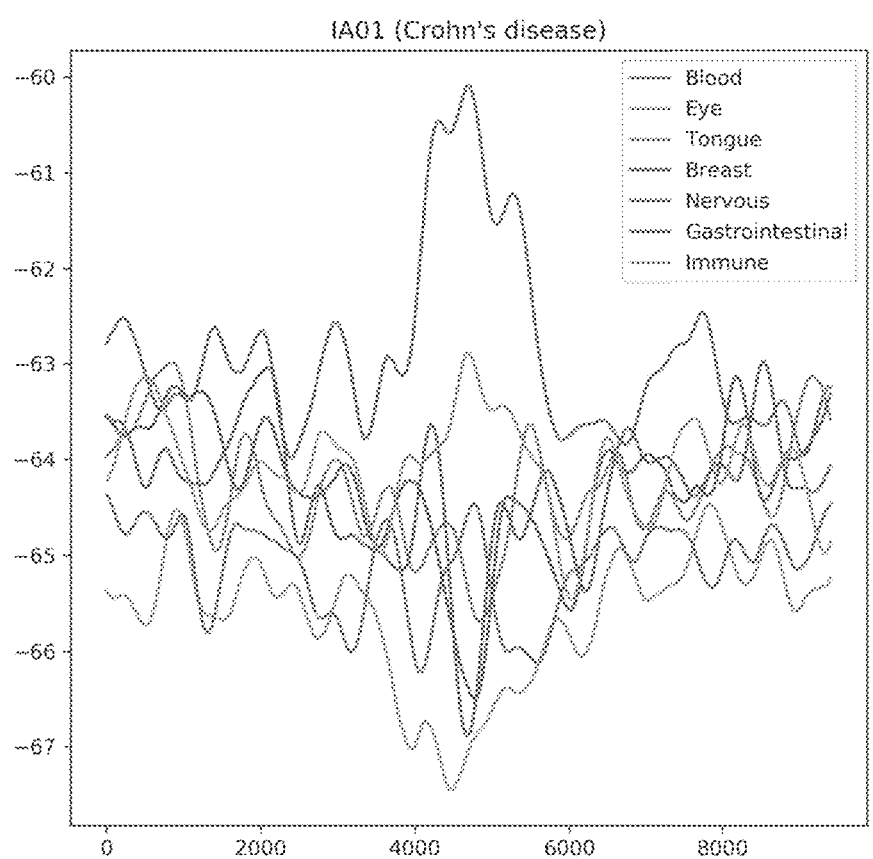

FIGS. 16 and 17 depict filtered V-plots for two autoimmune disorders: ulcerative colitis (FIG. 16) and Crohn's disease (FIG. 17). Cell-free DNA samples were used to make sequencing data sets for each disease, which were used to derive signature sequence signal maps and subsequent V-plots. The V-plots for each disease were filtered based on tissue origin and subsequently aggregated. The aggregated V-plots were plotted onto the same axes, as shown in of FIGS. 16 and 17, such that the X-axis is genomic position, with each signal V-plot centered on 5000. On the Y-axis is window protection score, which is a value where higher scores correspond to higher signal activity (i.e., more sequence signal present in sample). FIGS. 16 and 17 demonstrate that signals from circulatory blood tissue are highest, which is expected when cfDNA is extracted plasma. The second highest signal is lymphoid tissue of the immune system, indicating that the immune system may be highly active, as would be expected in samples derived from patients having autoimmune disorders. Also of note is that ocular tissue of the eye is very low, which can be used as control, as signals corresponding to ocular tissue would be expected to be very low in cfDNA samples.

Example 7: Filtered and Compressed V-Plots to Detect Neoplasms

Figure 18:
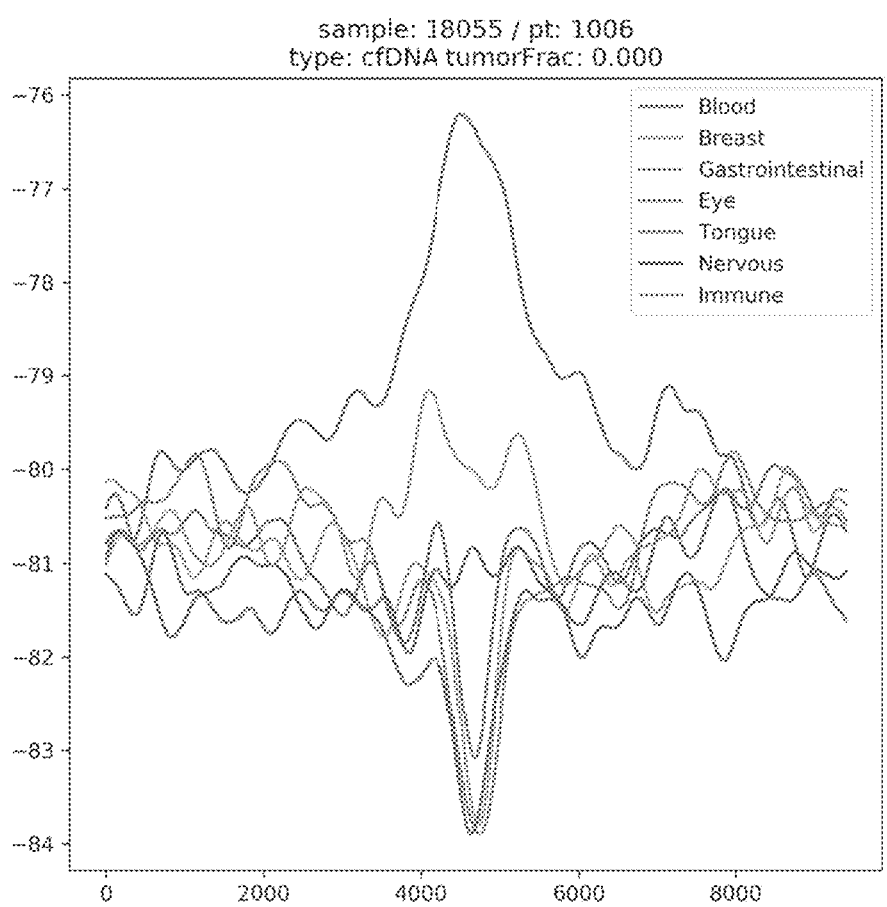
Figure 19:
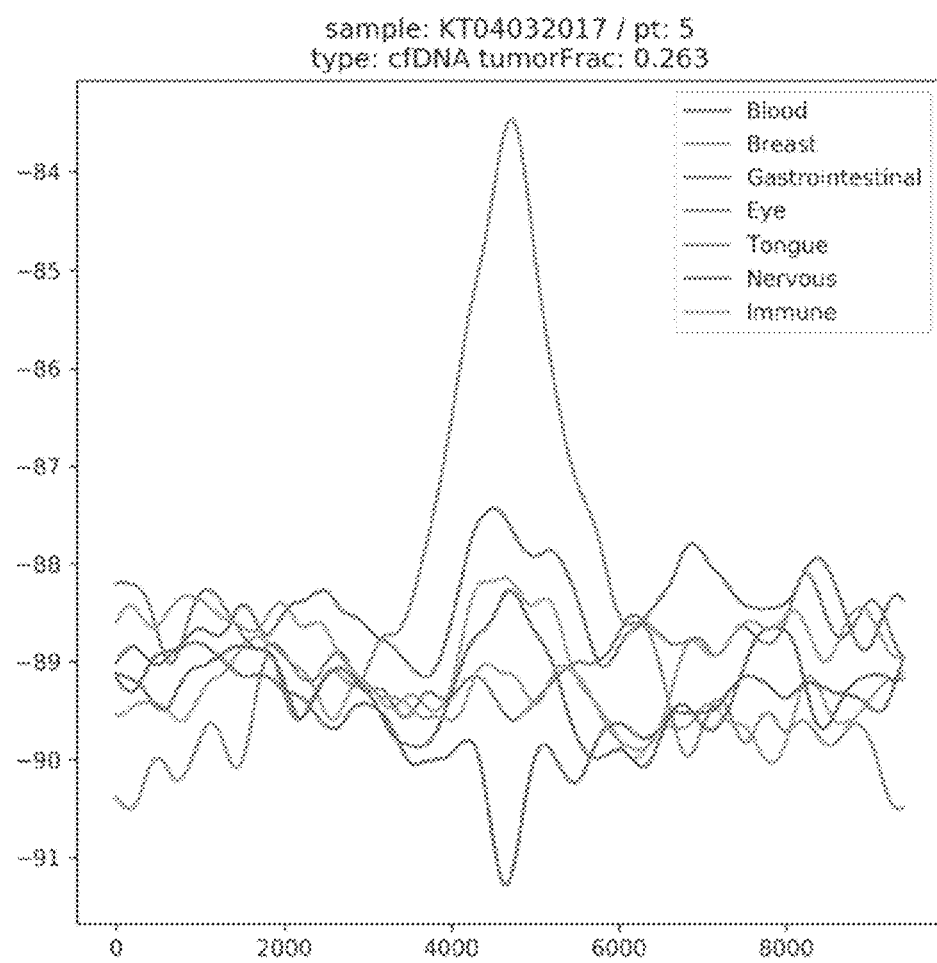
Figure 20:
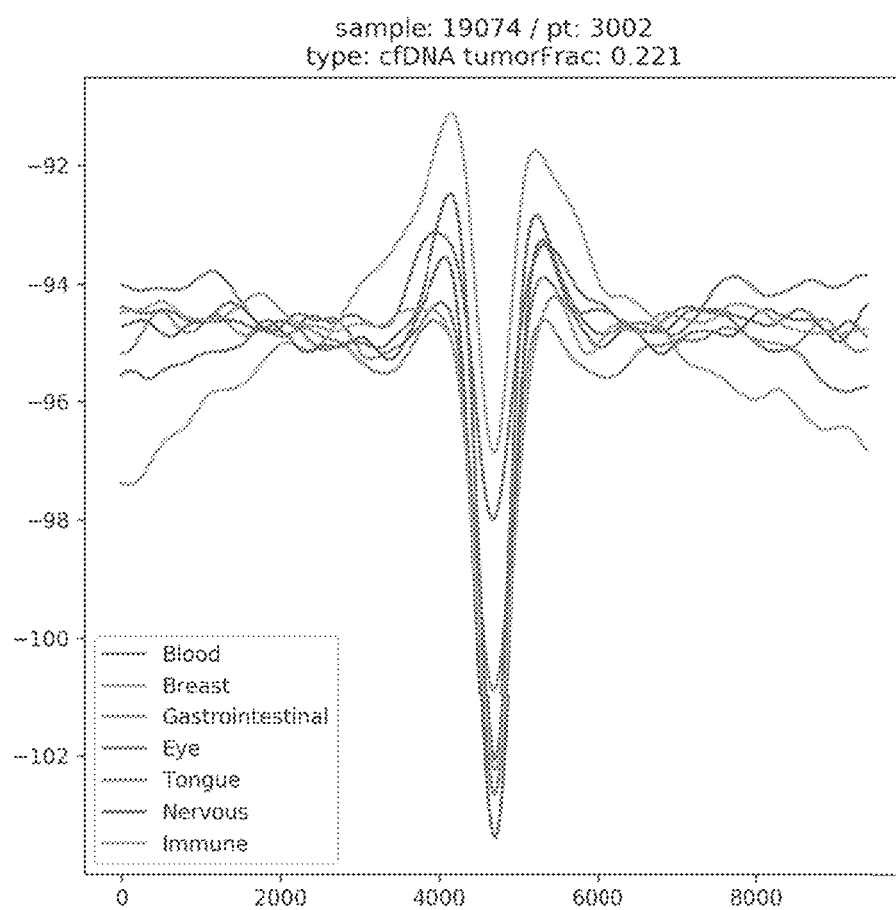

Provided in FIGS. 18 to 20 are filtered and compressed V-plots of three cfDNA samples extracted from plasma samples of three individual patients. The V-plots for each disease were filtered based on tissue origin and subsequently aggregated. The aggregated V-plots were plotted onto the same axes such that the X-axis is genomic position, with each signal V-plot centered on 5000. On the Y-axis is window protection score, which is a value where higher scores correspond to higher signal activity (i.e., more sequence signal present in sample).

In FIG. 18, the patient was diagnosed with early stage breast cancer. As the filtered and compressed V-plots show, the circulatory blood tissue provides most of signal in the cfDNA. Breast tissue remain low, likely due to the fact that the cancer is very rudimentary, and thus hasn't produced many signals that can be picked up in cfDNA derived from plasma. Interestingly, lymphoid tissue signals from the immune system are elevated in the sample, which may indicate that the immune system is activated in response to the neoplastic growth. Thus, in some instances, a higher level of lymphoid tissue signals may be an indication of early stage cancer.

The filtered and compressed V-plot signals in FIG. 19 are derived from a patient that has a rare type of malignancy of the ovary that has metastasized from a primary site (often the gastrointestinal tract). As can be seen in the data, the cfDNA has a high level of gastrointestinal signal, likely due damage, fibrosis, and/or cellular lysis of gastrointestinal tissue due to the invading metastases. Accordingly, this data suggests that nucleic acid signal derived from cfNAs may be useful in identifying and locating sites of metastases.

In FIG. 20, the patient was diagnosed with metastatic breast cancer. Unsurprising, breast tissue signals are the highest signals in the sample, likely a result of metastatic breast tissue. This data confirms that advanced stage neoplasms, and especially metastatic cancerous tissue, can be readily detected in a patient's cfDNA derived from plasma.

Example 8: More Filtered and Compressed V-Plots to Detect Neoplasms

Provided in FIGS. 21 to 24 are filtered and compressed V-plots of four cfDNA samples extracted from plasma samples of four different experiments. The V-plots for each patient were constructed using the top 1000 or top 5000 tissue origin signal peaks and subsequently aggregated. The aggregated V-plots were plotted onto the same axes such that the X-axis is genomic position, with each signal V-plot centered on 1000. The V-plots were smoothened using a Gaussian density kernel, and thus the Y-axis is Gaussian density kernel score, which is a value where lower scores correspond to higher signal activity (i.e., more sequence signal present in sample).

Figure 21:
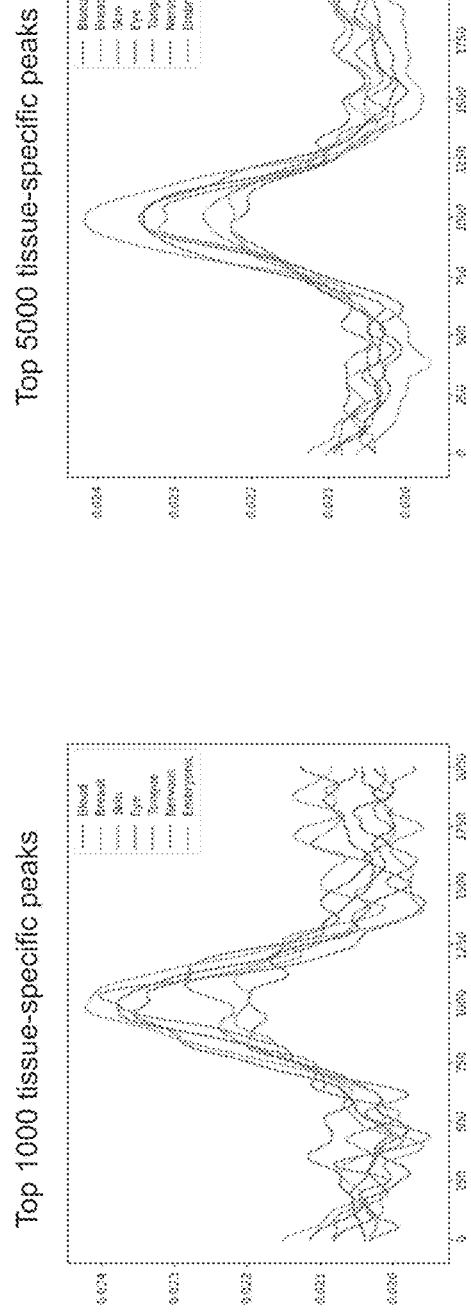

FIG. 21 provides filtered and compressed V-plots of a cfDNA extracted from a patient having breast cancer with skin metastases. As shown in the two plots, both breast and skin tissue signals are elevated as a result.

Figure 22:
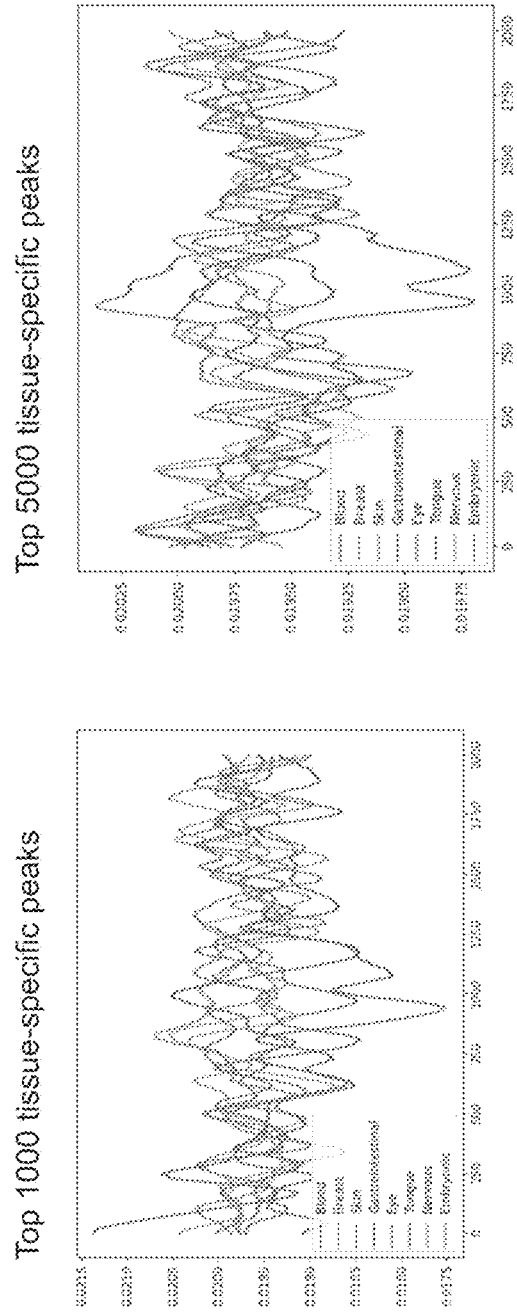

In FIG. 22, the cfDNA sample utilized to produce FIG. 19, is reanalyzed to provide alternative filtered and compressed V-plots. As can be seen, gastrointestinal tissue signals are elevated, confirming the results of FIG. 19 by an alternative methodology.

Figure 23:
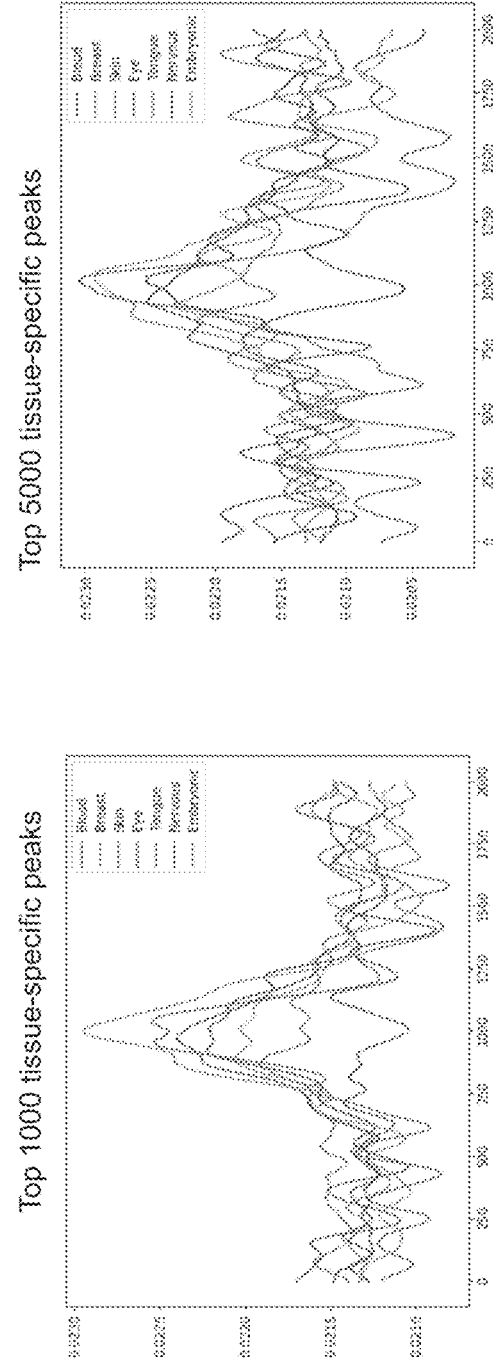

The filtered and compressed V-plot signals in FIG. 23 are derived from cfDNA extracted from a patient having melanoma. The V-plot signals indicate an elevation of skin tissue signals, which would be expected.

In FIG. 24, filtered and compressed V-plot signals are provided that are derived from pooled cfDNA extracted from a cohort of patients having early stage breast cancer. The plots indicate that circulatory blood tissue provides the most active signals, while breast tissue signals remain low.

Example 9: Filtering of V-Plots

Figure 25A:
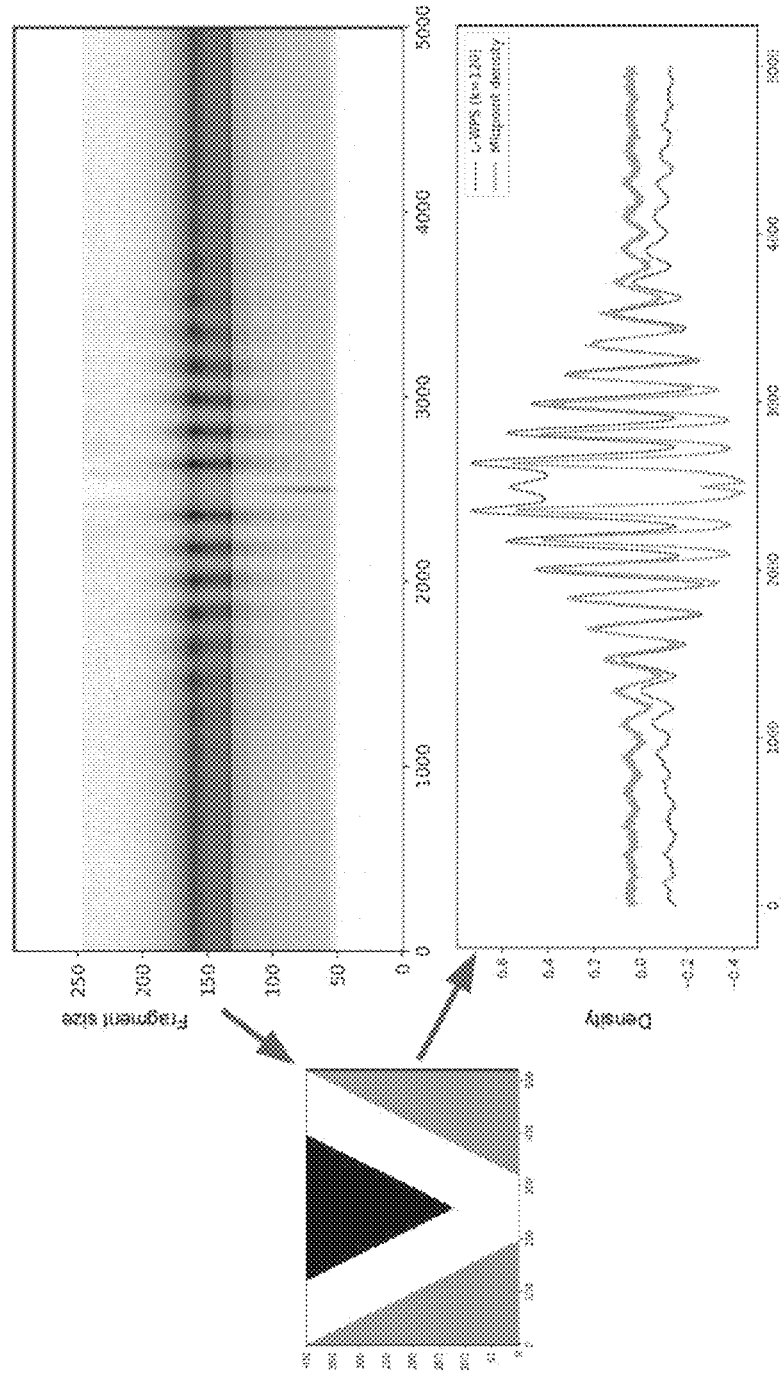
FIG. 25A provides an example of a cross-correlation filter, extracting a density plot from the V-plot signal in accordance with various embodiments of the invention.

In FIG. 25A, a sample V-plot is provided in the top panel, which is centered at 2,500. Plotted on the y-axis of the V-plot is fragment size. The V-plot is filtered through a cross-correlation filter to yield density of signal.

A parameterized filter having various lengths is provide in FIG. 25B. The sample V-plot in the top panel is filtered, and separated by parameter length (k), which is depicted in the lower V-plot.

Provided in FIG. 26 is a separation of sequence signals of greater than 140 bp (top panel) and less than 140 bp (bottom panel). Nucleosomes yield sequences around 160 bp, whereas sequences associated with factors often yield sequences around 120 bp. By separating the sequence by size, the lower panel presents a strong signal centered in the middle for a sequence associated with a factor. Likewise, the top panel presents a sine curve representing evenly spaced out nucleosomes.

Example 10: Filtered V-Plots for Detecting Neoplasms, Cancer Progression, and Treatment Response FIGS. 27 to 33 provide V-plots of various patients having neoplasms. The V-plots for each disease were filtered based on tissue origin and subsequently aggregated. The aggregated V-plots were plotted onto the same axes such that the X-axis is genomic position, with each signal V-plot centered at peak summit. On the Y-axis is normalized window protection score, which is a value where higher scores correspond to higher signal activity (i.e., more sequence signal present in sample).

Figure 27:
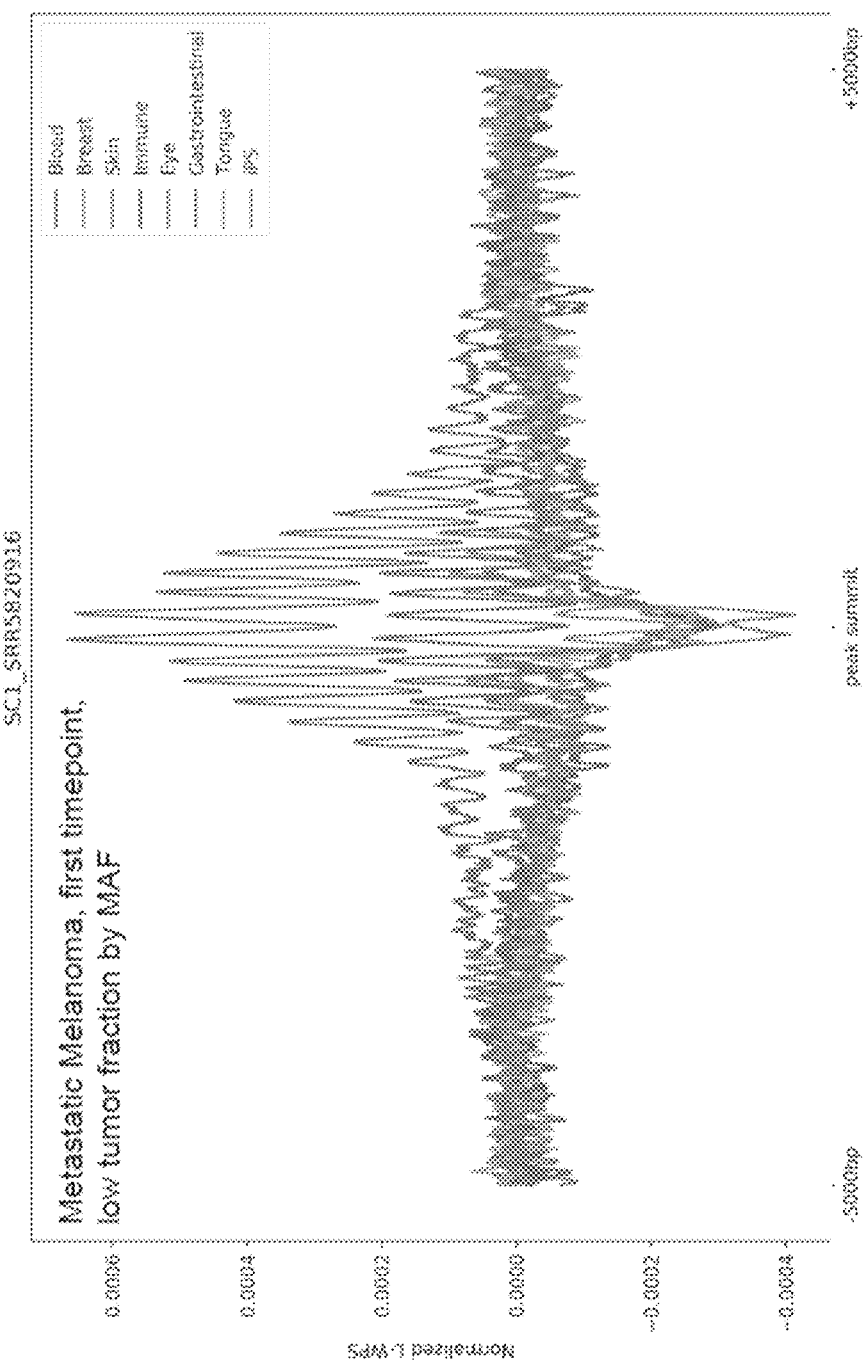
FIGS. 27-33 provide exemplary filtered and compressed V-plots of cell-free DNA samples derived from individuals having a neoplasm, including results from treatments, generated in accordance with various embodiments of the invention.
Figure 28:
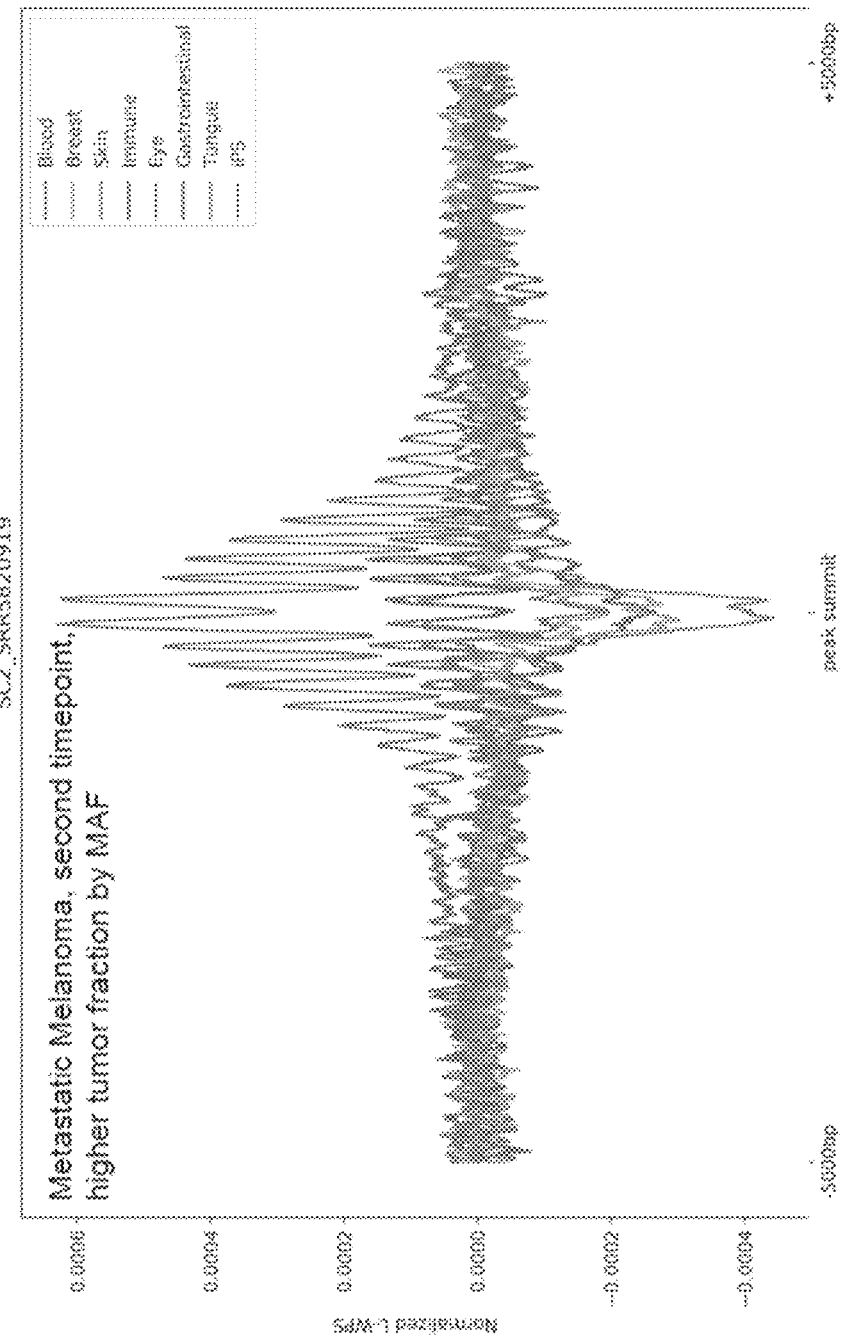

In FIGS. 27 and 28, compressed V-plots of a patient diagnosed with early stage melanoma are presented at two time points. In the first time point (FIG. 27), the immune response is relatively high (2nd to blood), likely indicating an activated immune response to the early stage cancer. Also of note is that signals related skin tissue is also elevated, likely due to the melanoma itself. In the later time point (FIG. 28), the immune response remains high and the skin response increases, suggesting an advancement of the cancer and/or response to treatment which leads to more melanoma cell lysis that is detected.

Figure 29:
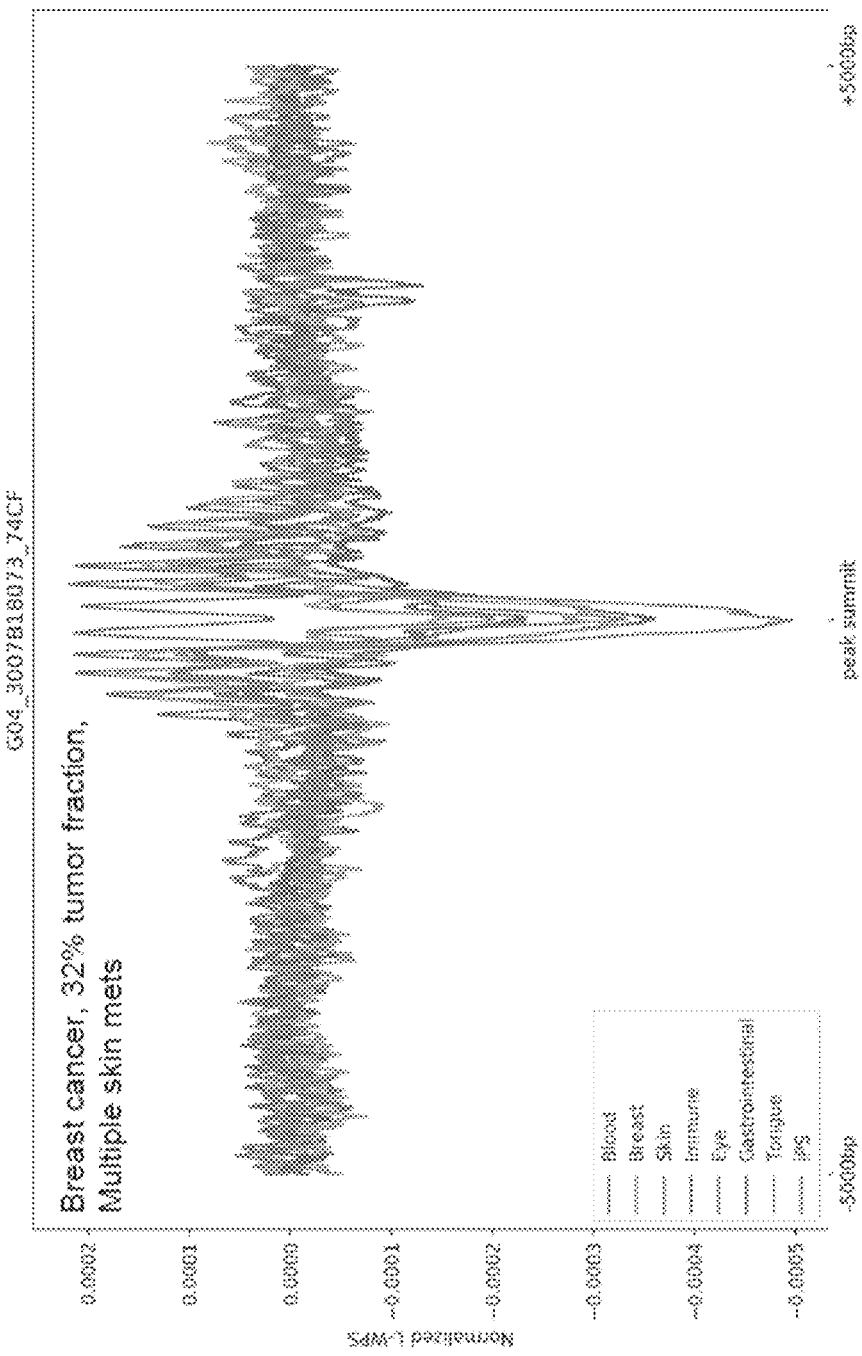
Figure 30:
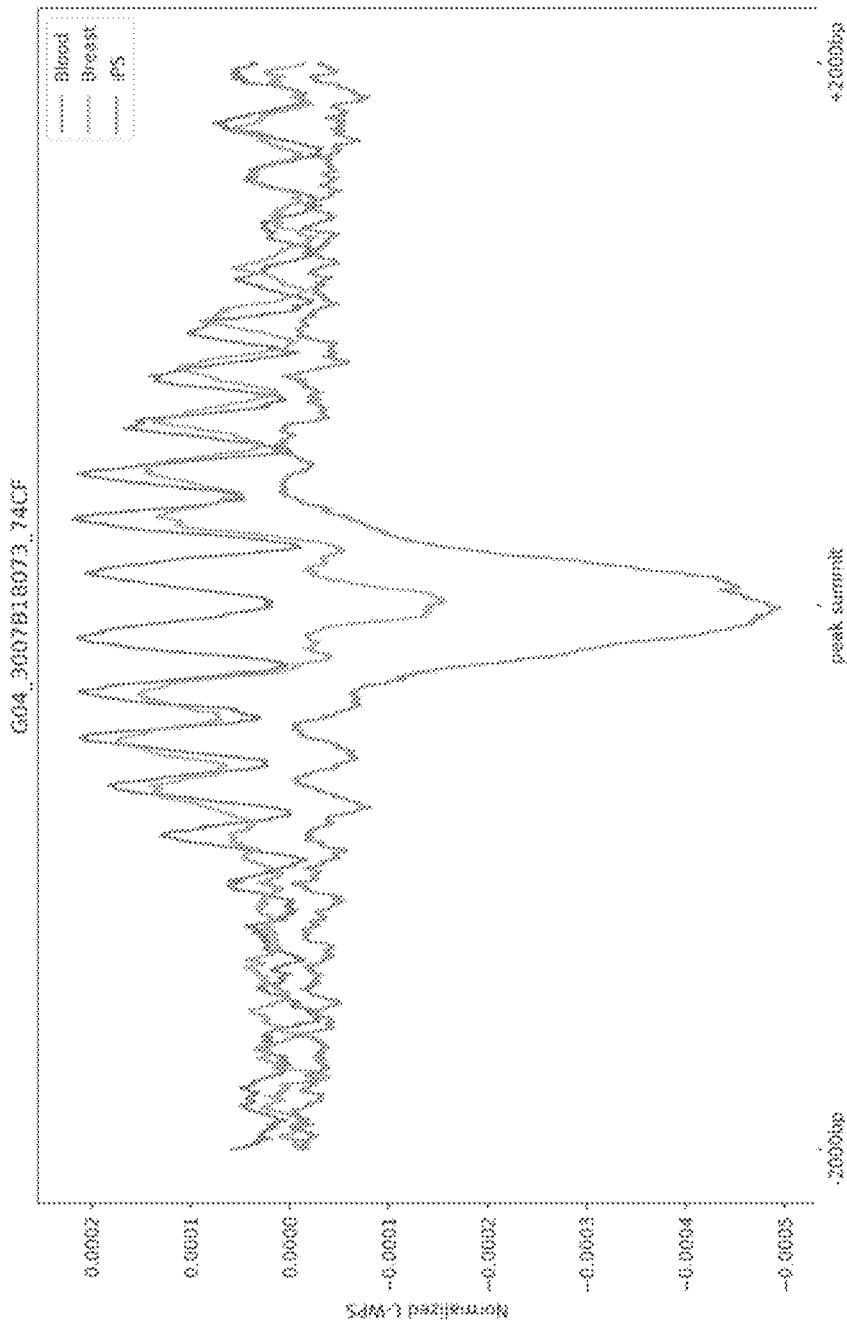

Provided in FIG. 29 are compressed V-plots of a breast cancer patient having multiple skin metastases. The V-plots reveal a high tissue signal for both breast and skin, likely due to the breast cancer itself and the metastases disrupting skin tissue. FIG. 30 provides a highlighted V-plot only looking at signal from breast tissue, positive control (blood tissue), and negative control (iPS tissue).

Figure 31:
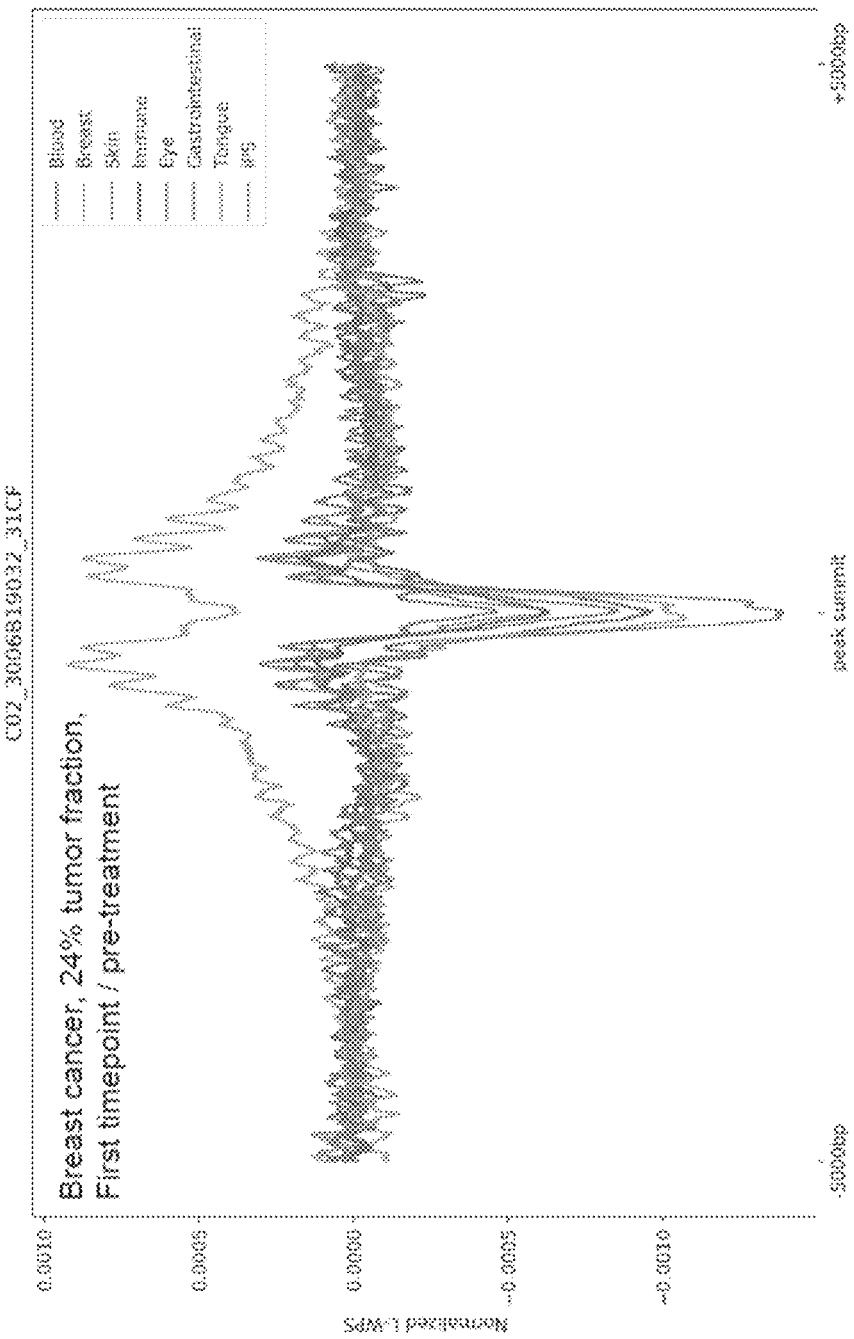
Figure 32:
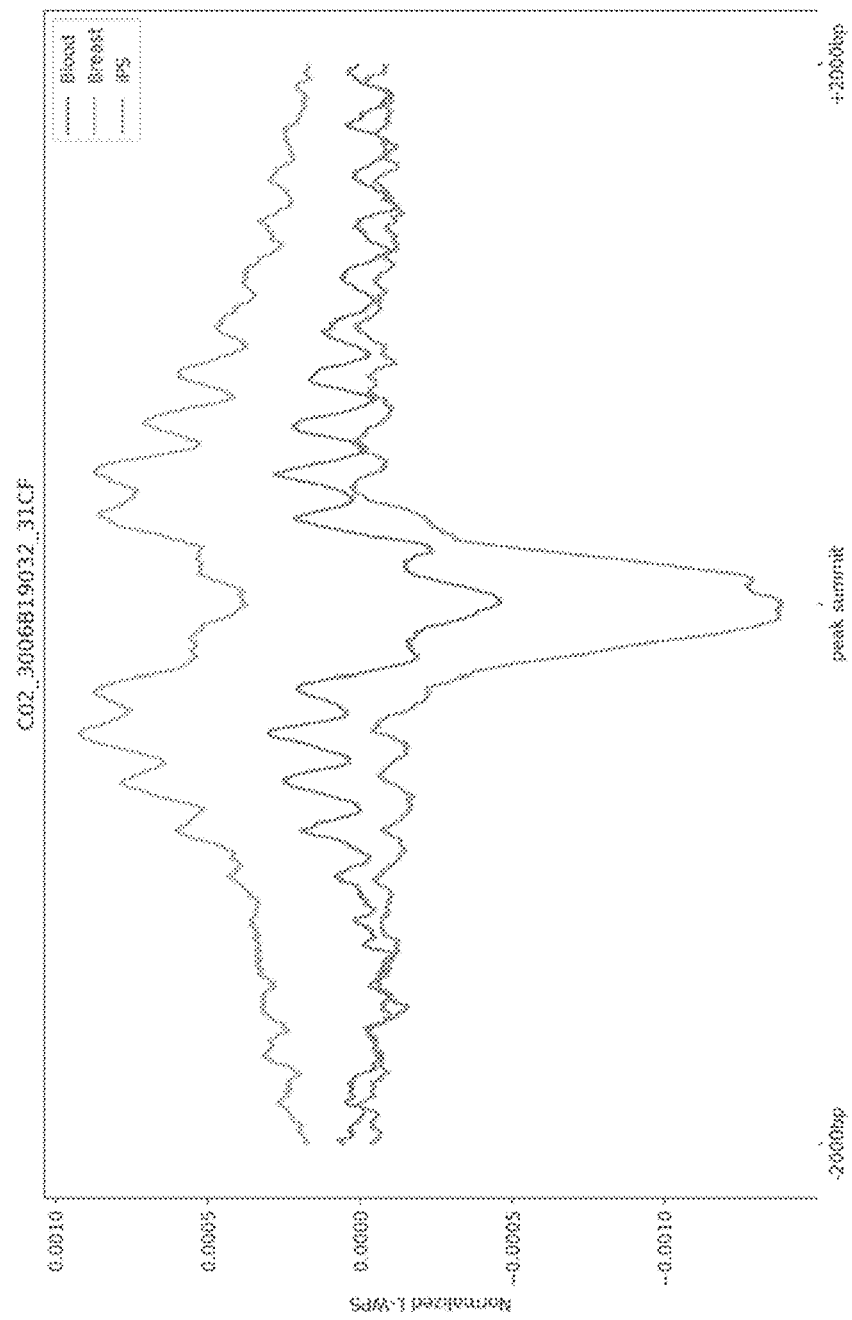
Figure 33:
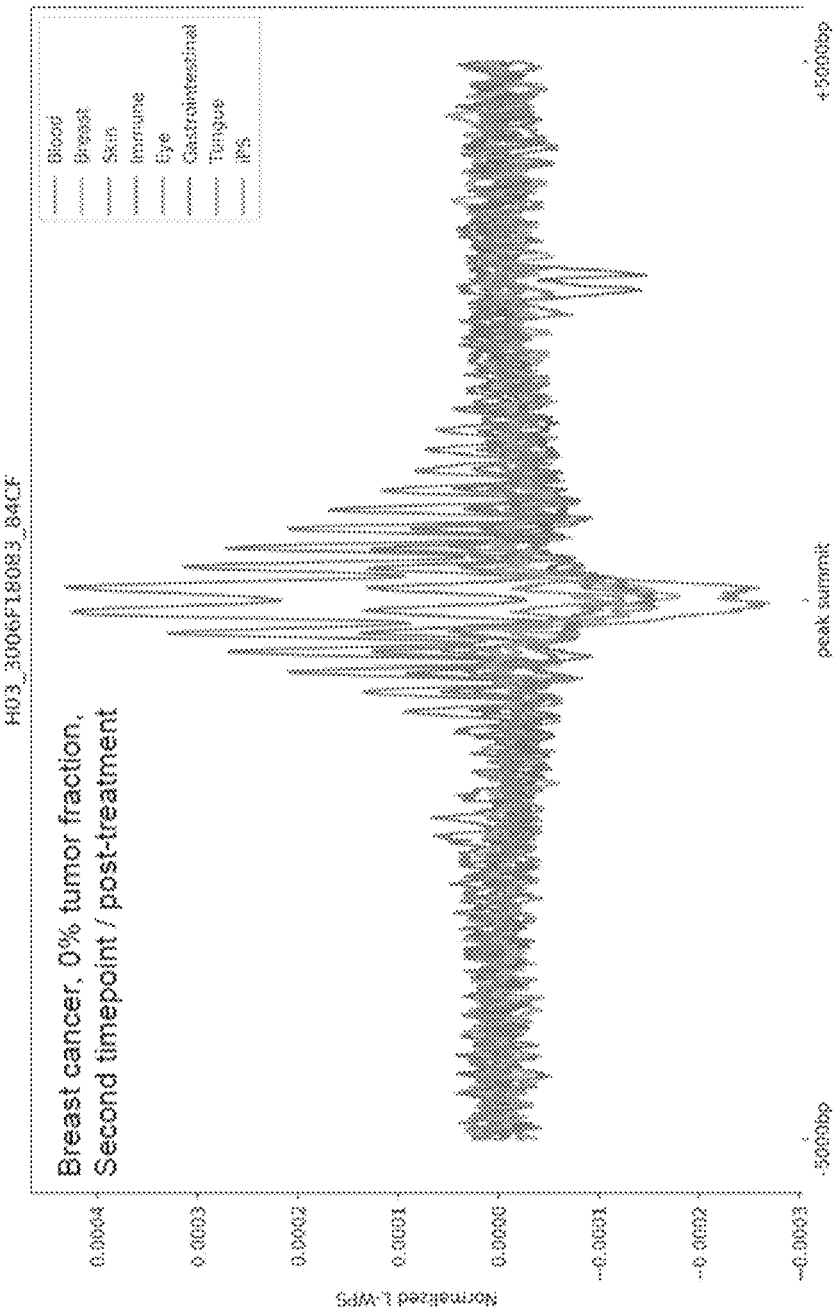

The V-plots provided in FIGS. 31 to 33 represent signals before and after treatment of a patient having metastatic breast cancer. In FIG. 31, the V-plots show that the patient had very high breast tissue signal in her cfDNA, likely due to the cancerous growth. FIG. 32 provides a highlighted V-plot, depicting only the breast tissue signals along with positive (blood tissue) and negative (iPS tissue) controls. In FIG. 33, the V-plots show very low breast tissue signal, potentially signifying that the treatment the patient received eliminated the cancerous breast tissue.

Example 11: Quantification of Signal from V-Plots

Figure 34:
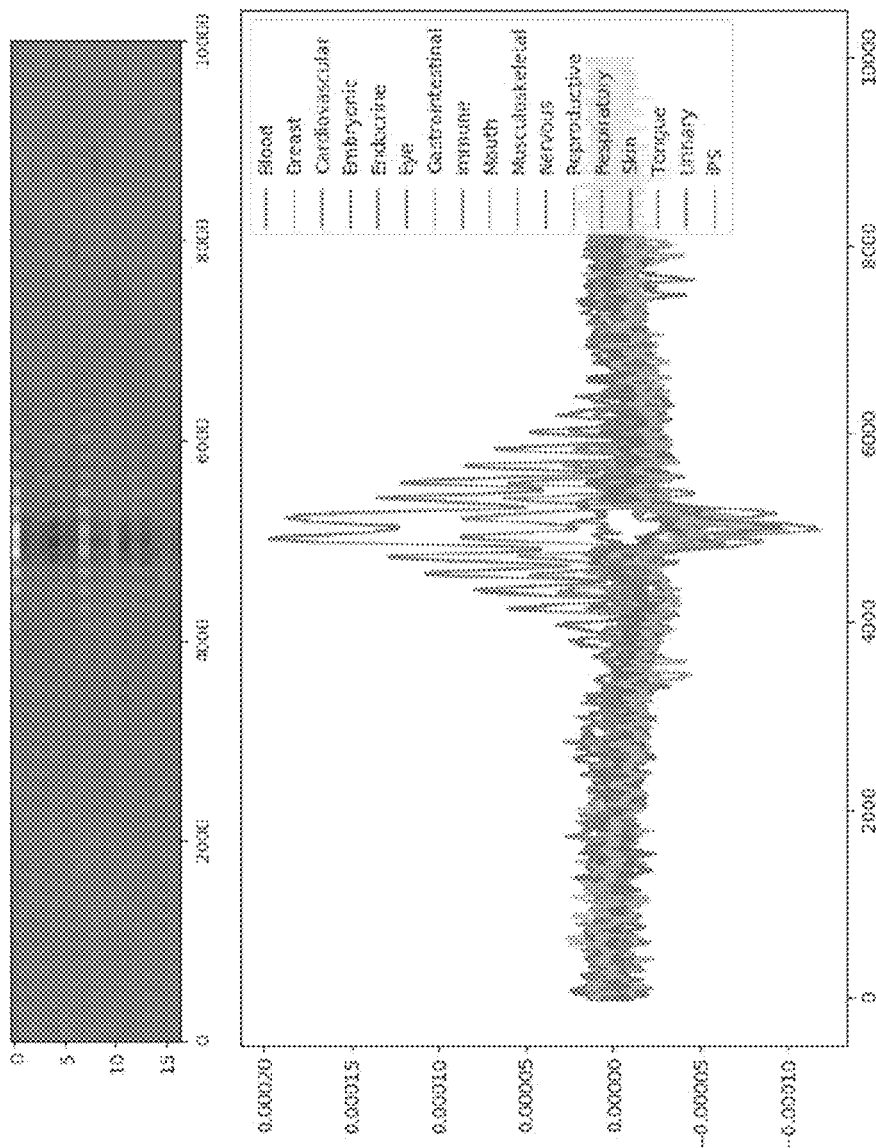
FIG. 34 provides a heat map quantifying a compressed V-plot, generated in accordance with various embodiments of the invention.
Figure 35:
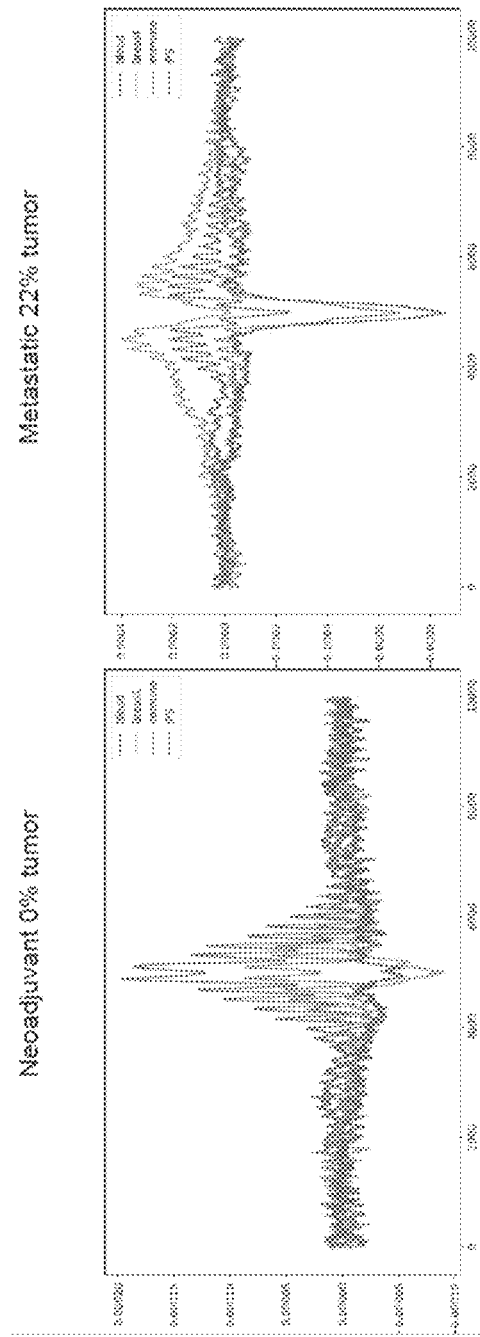
FIGS. 35-38 provide a relative quantification of compressed V-plot signals, generated in accordance with various embodiments of the invention.

Various embodiments are described to quantify the relative signal of tissue origins. For example, FIG. 34 provides V-plots depicting relative abundance of signal. The signal traces can be converted into colorimetric heat map, as depicted in the upper panel.

Figure 36:
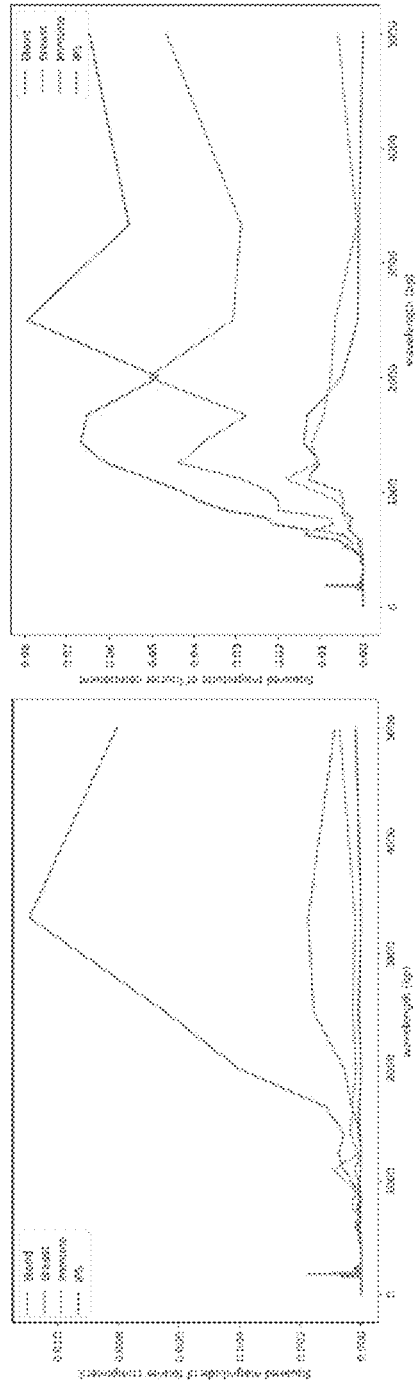
Figure 37:
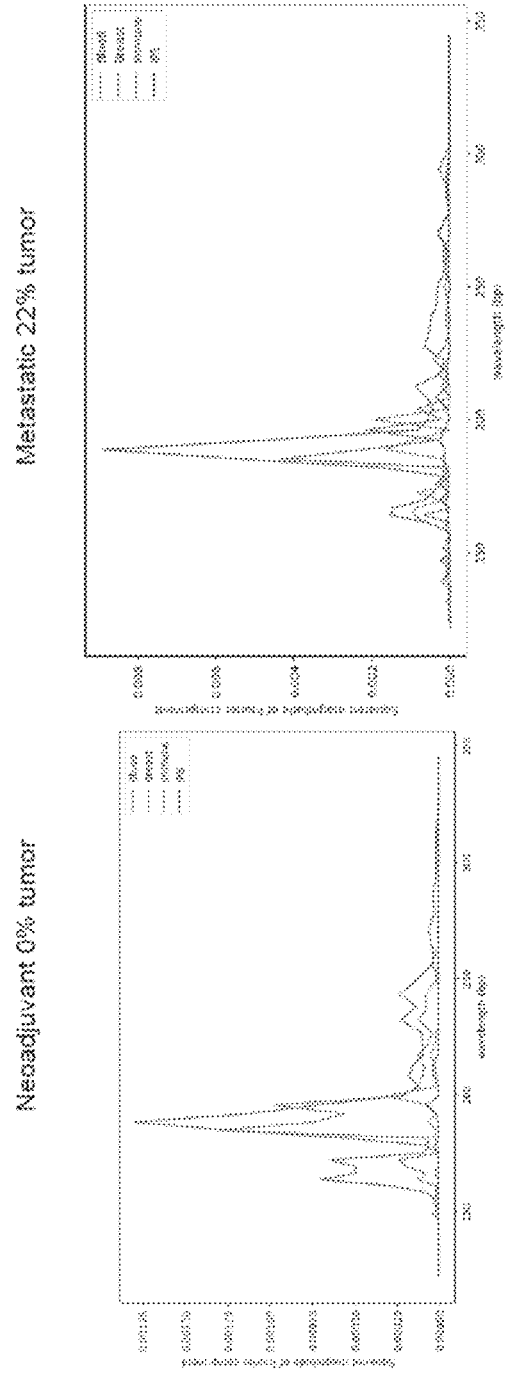
Figure 38:
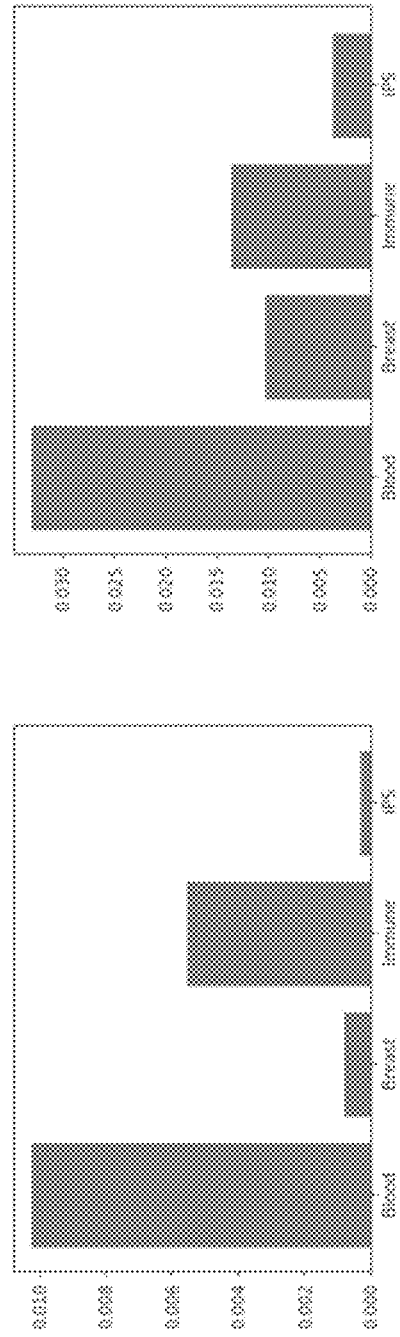

FIGS. 35 to 38 provide a method to quantify V-plot signal. In the left panel of FIG. 36 are V-plot signals of patient have very early-stage breast cancer. In the right panel, the V-plots are derived from the same patient, but after further development of the cancer, including metastases. The signals each V-plot are transformed via Fourier transformation to yield plots depicting wavelength (i.e., sequence length) against squared magnitude of the Fourier component. FIG. 38 focuses sequences less than 300 bp, which should be primarily sequence signals derived from nucleosomes and other protein factors. Utilizing these peaks, integrals (i.e., area under the curve) for each sample signal can be calculated, which is presented in FIG. 39. From these integral calculations, the signal of breast tissue to blood is rather low in the early stages of breast cancer, but rises significantly by the later, metastatic stages. Although the signals of breast tissue are low in the early stages of breast cancer, the signals for immune system are relatively high likely indicating an activated immune response. The immune system signals remain relatively high by the later stages as well. These data suggest that cfDNA sequences can signify whether the immune system is active, which can be used as an early-stage diagnosis and/or confirmation of diagnosis in various disorders, such as cancer.

Example 12: Use of Cell-Free DNA to Reveal Chromatin State and Tissues of Origin A major challenge in the field of non-invasive cell-free DNA diagnostics is inferring tissue of origin. This task is critical for the early detection of malignancy and may enable the detection of occult metastatic deposits in patients with established disease as well as the appropriate diagnosis of cancers of unknown primary (CUP) origin. As described in this example, a method was developed to accurately measure the relative abundance of tissues present in a sample by comparing the molecular fragmentation patterns around tissue-specific chromatin regulatory elements, outlined in FIG. 39. The analytical validity and internal consistency of the approach is demonstrated on primary samples from both healthy controls and cancer patients with diverse sites of disease, as well as through in silico titration and subsampling experiments, establishing a limit of detection of 0.5% tissue fraction. The approach includes an optimized method for detecting positioned nucleosomes from cell-free DNA V-plots, and thus creating the highest available resolution map of in vivo nucleosome positioning in human, and surveying extensive inter and intra TF diversity of in vivo nucleosome chromatin context across binding sites. The findings highlight the non-coding chromatin regulatory landscape captured in cell-free DNA, and reveal an orthogonal axis through which liquid biopsies may interrogate the epigenomic states of the tissues of origin.

Liquid biopsies have significant potential to transform how cancer and other diseases are diagnosed and treated. Diverse approaches to these non-invasive diagnostics are under intense academic and industrial development, including peripheral blood plasma cell-free molecular analytes such as linearized and circular cell-free RNA (cfRNA), exosomes, metabolites, and cell-free DNA (cfDNA). One of the key outstanding questions in the field are the processes and relative rates by which health and diseased tissues give rise to circulating nucleic acids, and how tissues of origin can be inferred from peripheral blood plasma cfDNA.

cfDNA has been known to exist in humans for >50 years, and extensive experimental work demonstrates its primary hematopoietic and lymphocytic origin. Other endogenous cells such as those in muscle and cardiovascular tissues have also been shown to contribute detectable amounts of plasma cfDNA, varying widely by physiologic state. In the case of pregnancy, fetal and placental cfDNA is detectable, often contributing >10% of maternal cfDNA fragments in the third trimester of pregnancy. In cancer, circulating tumor DNA (ctDNA) levels have been widely shown to correlate with disease stage, tumor burden, progression, and response to treatment.

Figure 39:
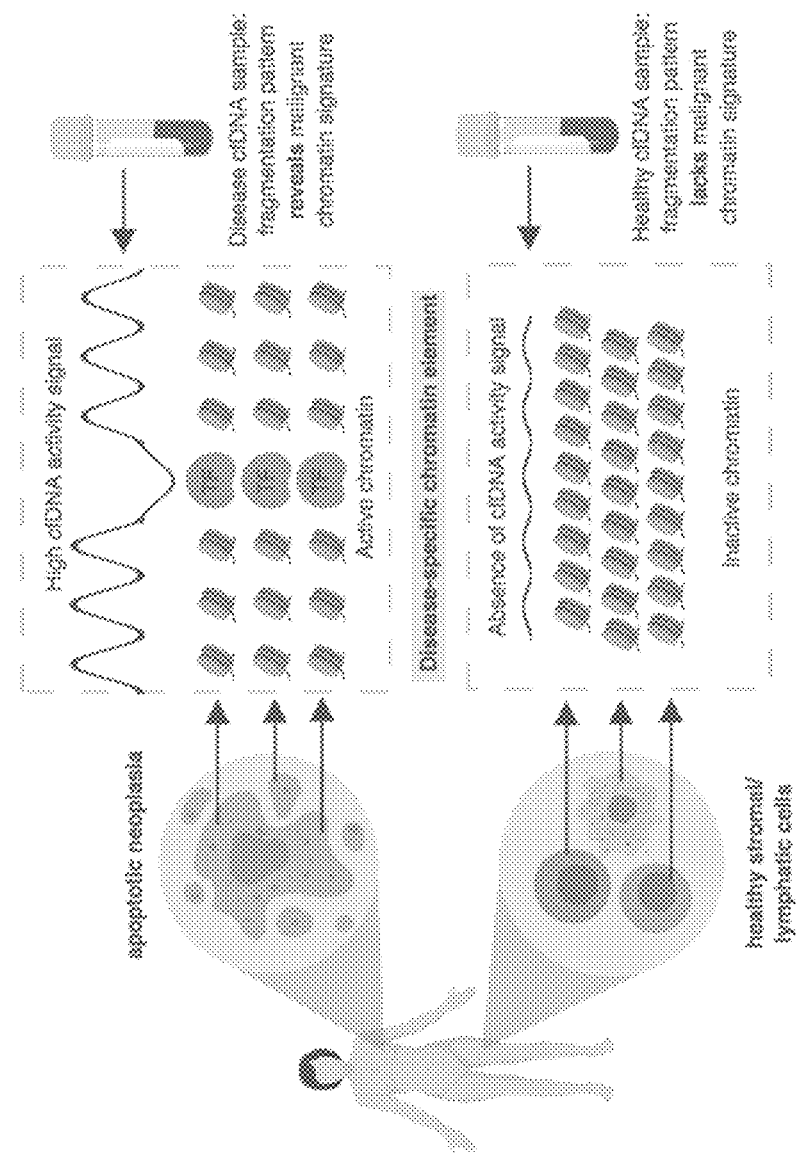
FIG. 39 provides a schematic diagram of cell-free nucleic acids in neoplasia and healthy tissue, which are used in accordance with various embodiments of the invention.

Here, a novel approach is presented to infer tissue of origin from cfDNA that measures cfDNA fragmentation patterns across millions of chromatin accessible elements whose activity is maximally discriminative to specific tissues and cell types, illustrated in FIG. 39. Using a biophysical phenotypic view, chromatin elements are defined as regions of the genome that are DNase sensitive, which may be considered putative regulatory regions or putative functional elements. Compared to existing approaches, using chromatin elements has many advantages: there are two orders of magnitude more distal chromatin elements (>2M) than genes (~18K), and differences in their activity across cell types are far more binary than the continuous valued differences typically observed in transcript expression between tissues. Additionally, chromatin accessibility is an epigenomic phenotype underlying virtually all known types of chromatin element state variation, whereas CpG methylation exists at only a very small subset of repressed chromatin elements, providing a strong advantage over tissue of origin methods relying on methylation signatures. Moreover, the input requirements are cfDNA WGS, and do not require specialized chemistry such as bisulfite conversion.

Figure 40:
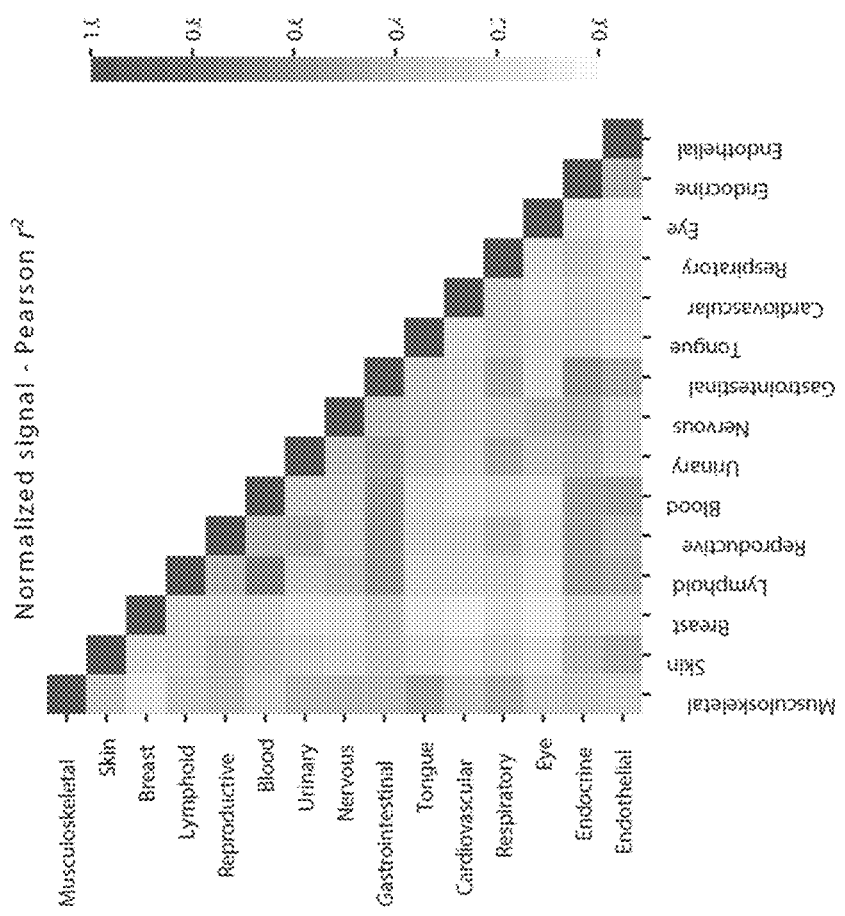
FIGS. 40 & 41 provide data graphs detailing origins of cell-free nucleic acids, utilized in accordance with various embodiments of the invention.
Figure 41:
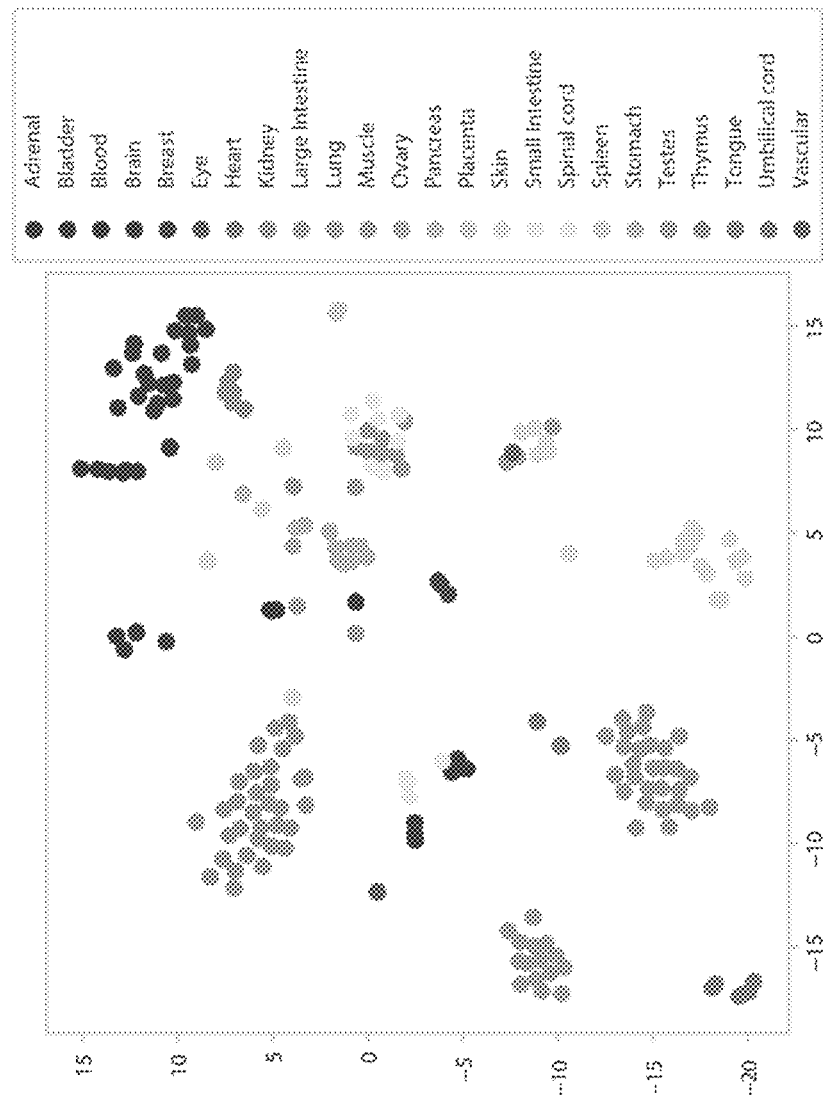
Figure 42:
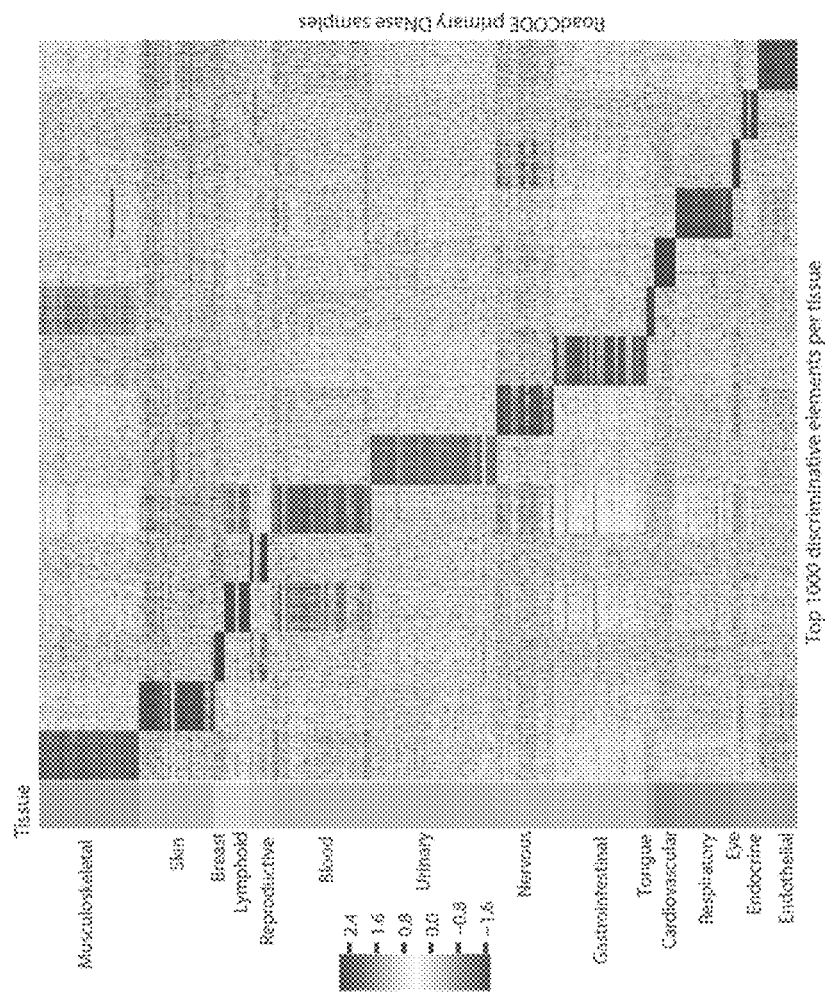
FIG. 42 provides top discriminative elements in various tissues, generated in accordance with various embodiments of the invention.

To establish reference chromatin signatures for analysis of cell-free DNA sequencing data, a large set (n=212) of DNase-seq samples was uniformly-reprocessed and annotated, shown in FIGS. 40, 41, and 42. An information-theoretic correlation metric was used to identify the 10,000 most discriminative chromatin elements for each annotation, yielding a catalog of >1M chromatin elements whose activity is maximally specific to each organ, tissue, and cell type, shown in FIGS. 40, 41, and 42. Overlaying cell-free DNA fragmentation patterns across these discriminative elements revealed tissue-specific signatures that correlate with the clinical information regarding the primary and metastatic sites of disease and tumor burden, illustrated in FIG. 39. The tissue of origin signal measurements also correlate with previous studies using methylation and imputed gene expression of the joint hematopoietic/lymphatic lineage of cell-free DNA in humans. In several clinical case studies, it was also demonstrated that longitudinal signal from our assay between samples correlates with clinical observation of response to targeted therapy (FIGS. 44, 52, 54), indicating potential uses of our technology in monitoring disease progression and treatment response.

Plasma cfDNA was collected from a cohort of 8 cancer patients, including 3 patients with multiple treatment time points, and 3 samples from healthy controls. By applying the analytic framework to cfDNA-derived WGS data from 11 samples spanning 8 patients with metastatic breast, skin, and gastric cancer, several with multiple time points it was demonstrated that it is possible to accurately estimate fractional abundance of tissues of origin using chromatin accessibility (FIGS. 43-48, 50, 52, 53), which has not been demonstrated with gene expression based approaches. The method is also able to detect non-mutated tissues, making it applicable to a far broader range of indications than methods that focus on detecting somatic variation from cfDNA, which also suffer from the background signal due to somatic mosaicism in the blood. Thus, the findings demonstrate the utility of cell-free DNA derived chromatin activity signatures for detecting a scientifically and clinically important variation across disease states.

Figure 43:
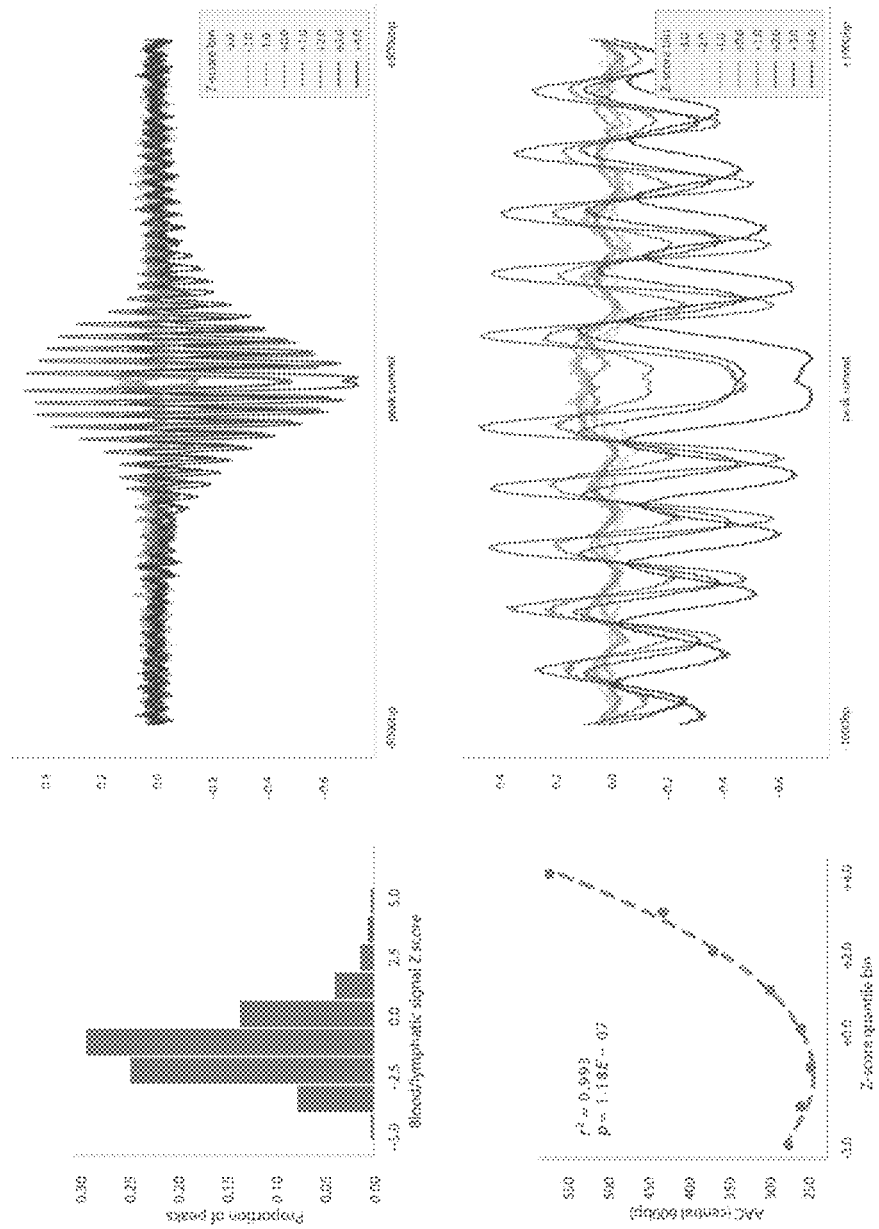
FIG. 43 provides various data graphs and V-plots, generated and utilized in accordance with various embodiments of the invention.
Figure 44:
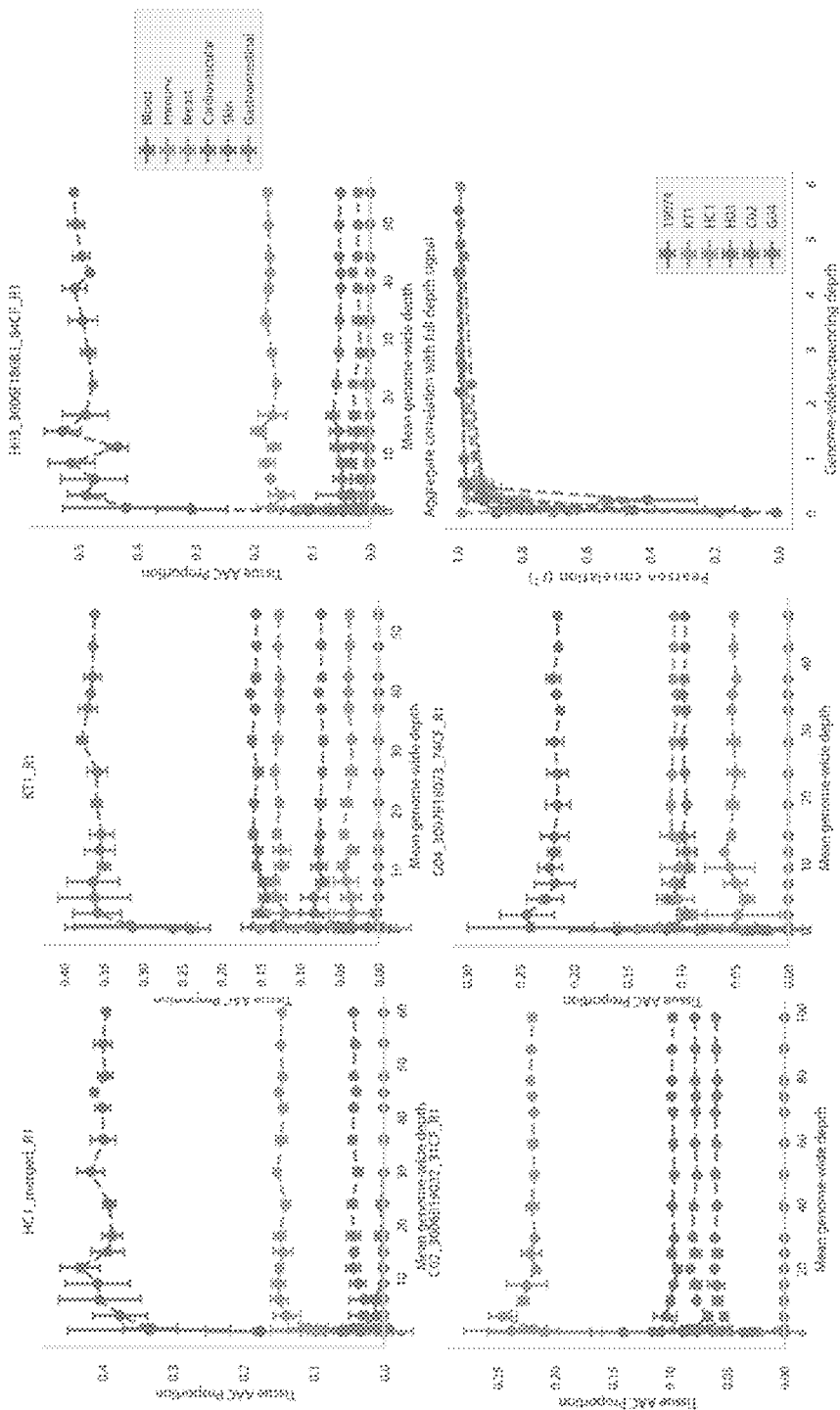
FIG. 44 provides data graphs of AAC estimates at each mean genome-wide depth sampled, generated in accordance with various embodiments of the invention.
Figure 45:
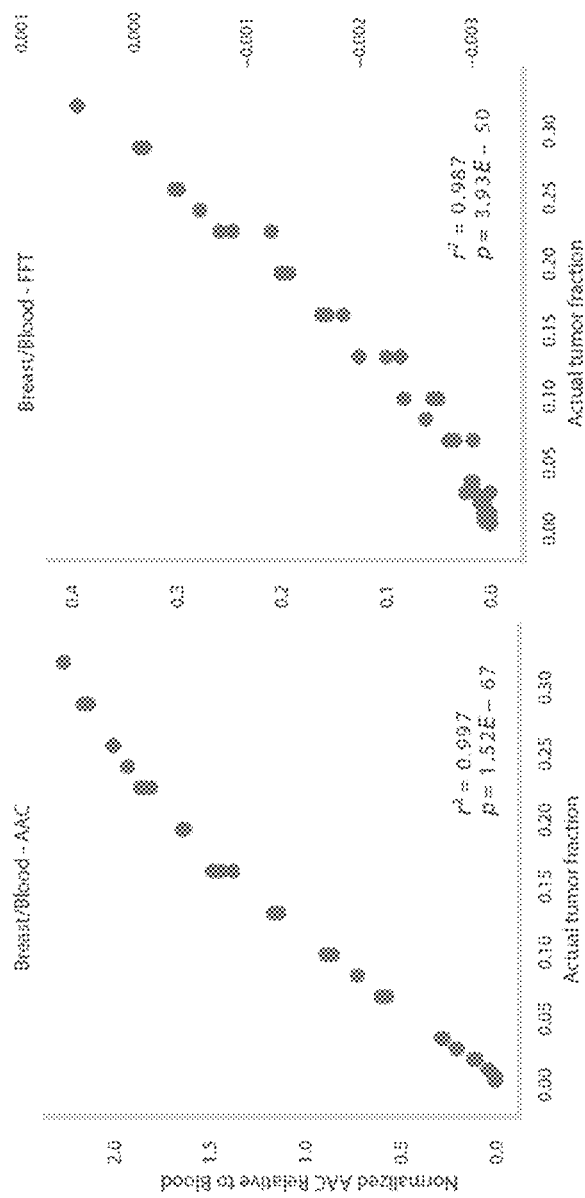
FIGS. 45 & 47 provide data graphs of normalized AAC relative to blood, generated in accordance with various embodiments of the invention.
Figure 46:
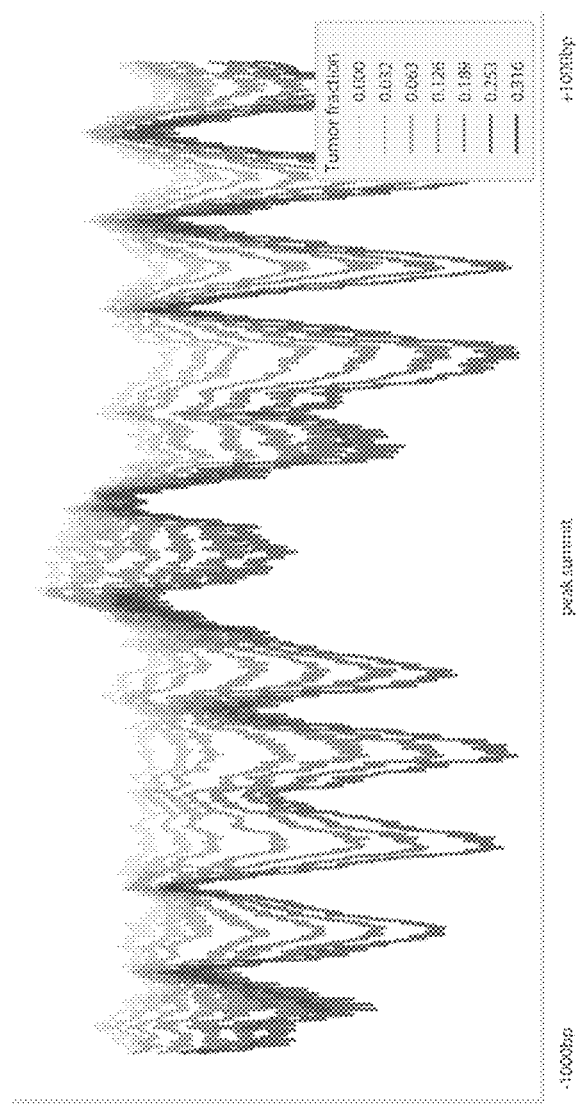
FIGS. 46 & 48 provide V-plot graphs, generated and utilized in various embodiments of the invention.
Figure 47:
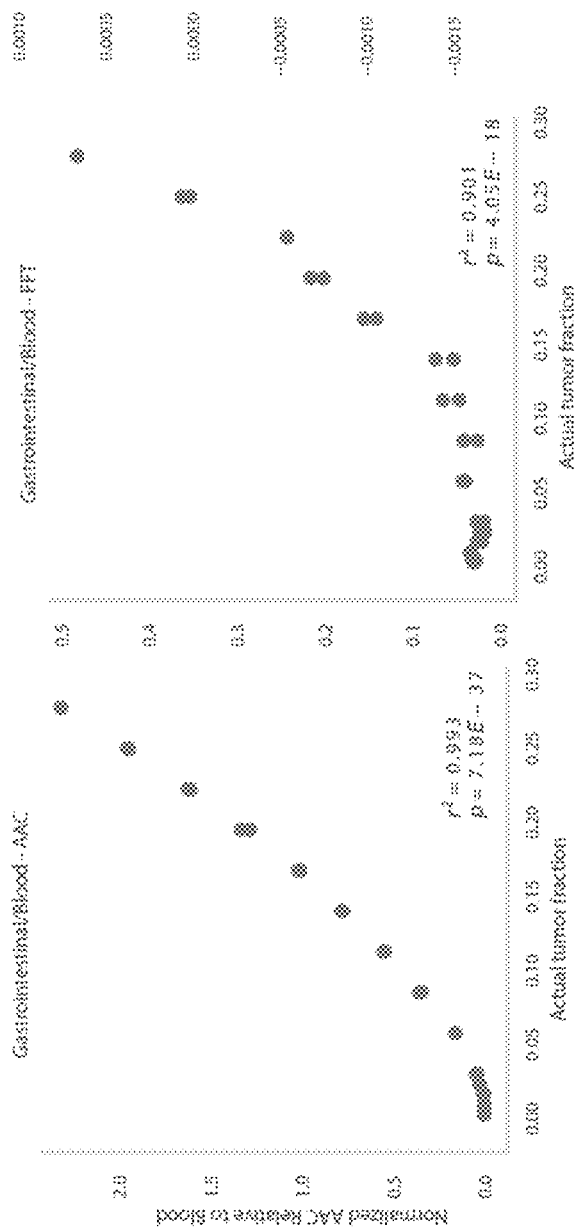
Figure 48:
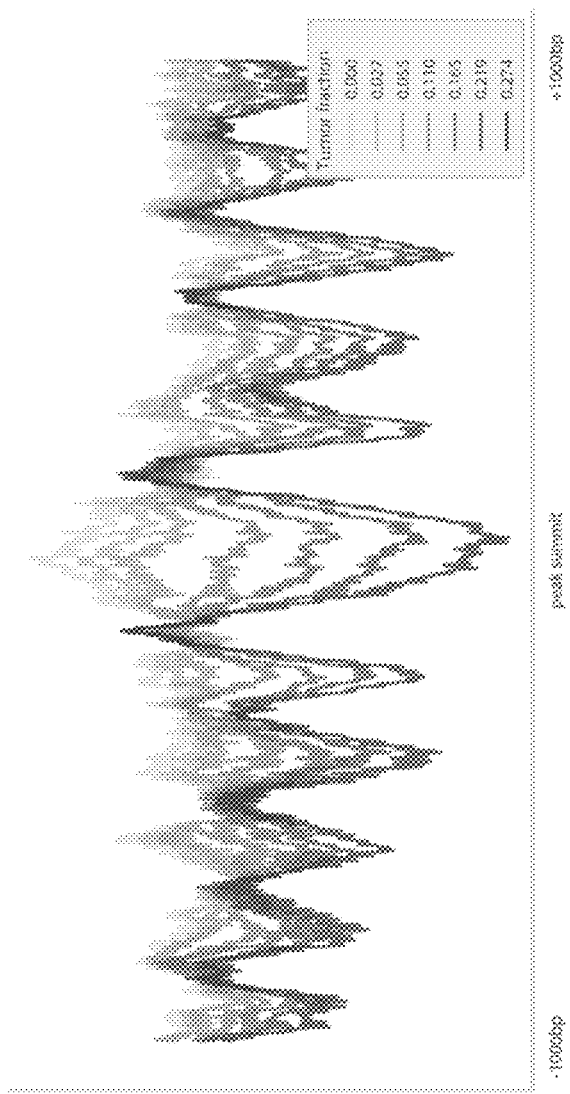

A Multi-Scale Index of Discriminative Chromatin Elements Across Hundreds of Human Tissues and Cell Lines To identify sets of maximally discriminative chromatin regulatory elements across all major human tissues and cell types, a large collection of DNase-I hypersensitivity sequencing (DNase-seq) datasets from the NIH ENCODE and Roadmap projects were uniformly reprocessed and reanalyzed, illustrated in FIGS. 43, 44, 45. These data sets have profiles of the accessible chromatin landscape of hundreds of human tissues and cell lines. The integration of these datasets is especially challenging because technical differences in sample quality, library preparation, sequencing, analysis pipelines, and metadata between and within the datasets confound (and often outweigh) biological differences. These issues were overcome by uniformly reprocessing the datasets from raw sequencing files, applying stringent quality filtering and batch correction steps, and developing a pipeline to automatically collect and facilitate manual curation of uniformly comprehensive sample metadata at multiple physiologic levels of annotation.

327 DNase-seq datasets of unique samples were first identified and downloaded from phases I-III of the NIH ENCODE and Roadmap Epigenomics project. The datasets were trimmed to a uniformly equal read length (36 bp), starting from the 5' end of the read, which empirically minimizes sequencing platform-specific position-dependence of base call quality scores and mappability, and subsampled each dataset to 35M unique, aligned, non-mitochondrial fragments. The metadata for all 327 samples were also programmatically downloaded and manually curated, including generating multi-scale annotations at the organ system, organ, tissue, and cell type level for each sample, as well as covariates including lab, platform, and original sequencing depth. Outputs of this process are illustrated in FIGS. 43, 44, 45.

The uniformly trimmed, subsampled datasets were reprocessed using an optimized DNase processing pipeline (detailed in Methods), which performs standard alignment, filtering, peak calling, and quality control steps. After quality control analysis, 115 samples were discarded due to low alignment rates, poor peak call quality, or erroneous signal clustering with respect to other samples from the same tissue. This yielded a final set of 212 high quality DNase-seq datasets, which were used for all further analysis. Outputs of this process are illustrated in FIGS. 43, 44, 45.

The full set of 212 high quality samples contains 1.6 million unique high-confidence signal peaks, representing a large-scale encyclopedia of regulatory elements across human tissues and cell lines, representing 31 unique tissues in total. The peak summit positions were further refined to improve alignment across peaks by examining evidence from the original sequencing datasets, as well as the occurrence of known ChIP-seq derived TF motifs present in the peak intervals (as further detailed in the Methods section below). Outputs of this process are illustrated in FIGS. 43, 44, 45.

For each sample, the number of fragments overlapping each element was calculated, producing a peak-sample fragment count matrix. Limma (see M. E. Ritchie, et al., *Nucleic Acids Res.* 43, e47 (2015), the disclosure of which is incorporated herein by reference), a transcript quantification tool, was then used to transform the raw counts into normalized signal by modeling count dependence and overdispersion. Discriminative regions for each level of physiologic annotation (system, organ, and cell type) were identified using two different techniques: using Voom to perform differential accessibility calls for each annotation compared to the mean of all other annotations, as well as a weighted mutual information score that provides a normalized metric of the Mutual Information (MI) between each element and each annotation class. Both approaches reveal thousands of elements that are highly discriminative to each cell type, organ, and system measured, and provide a weight for the specificity of each element. Reassuringly, the intersection between the top 10,000 elements identified by Voom and by weighted MI was high (0.61 IoU), suggesting the identity of such elements is robust to the method used for selection. This catalog of tissue discriminative elements was used as the basis for all further tissue of origin quantification from cell-free DNA samples. The level of tissue discrimination can be seen in FIG. 42.

Cell-free DNA can be modeled as a nuclease-driven chromatin degradation process at equilibrium. Chromatin molecules are released when cells apoptose and are rapidly degraded by nucleases prevalent in blood plasma. This degradation process exhibits nonlinear degradation rate, with seemingly quantized DNA molecule fragment length states, because individual nucleosomes protect DNA in discrete 160-180 bp intervals. Internucleosomal regions are preferentially cleaved because they lack protection, but nucleosomes provide chemical and steric hindrance to nuclease degradation. Robust in vivo and in vitro evidence shows cfDNA exists in an exponentially attenuated sinusoidal "ladder" density distribution with a dominant frequency component of ~180 bp, corresponding to integer multiples of nucleosome protection. In cfDNA libraries prepared for this study, as well as in 3/3 publicly available sources of high-coverage cfDNA from metastatic patients that were examined, >99% of the unique mapped fragments are 150-180 bp long, which corresponds to the expected size distribution of fragments protected by mononucleosomes.

Figure 49:
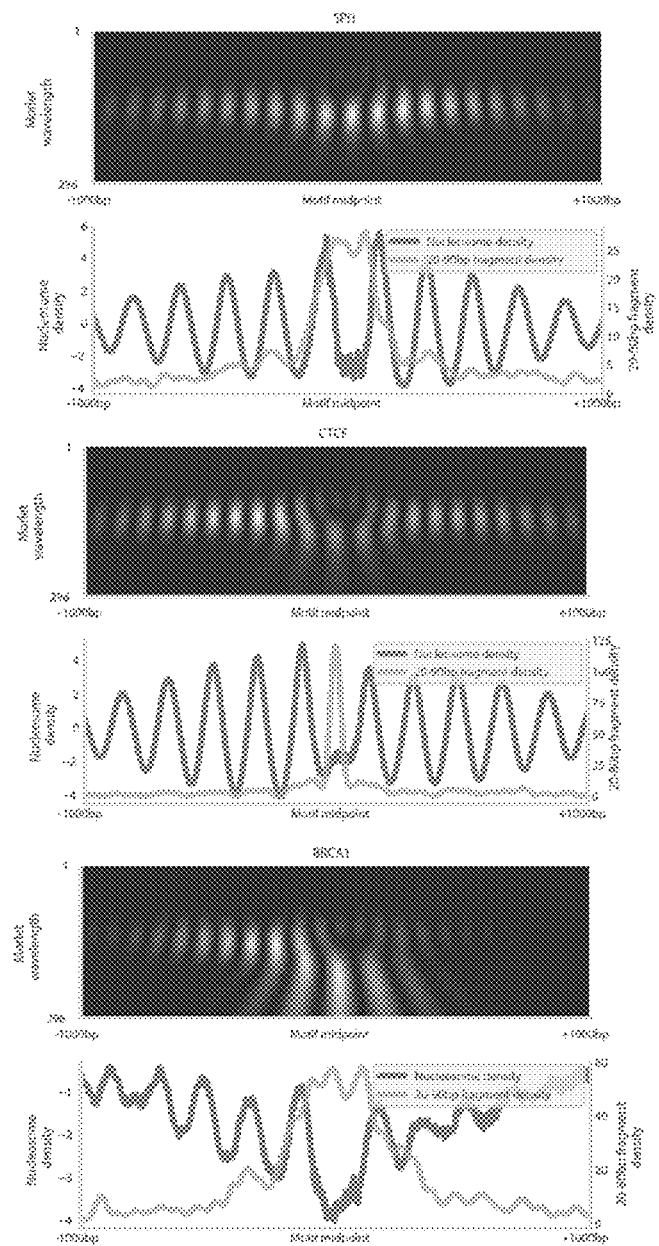
FIGS. 49 & 50 provide V-plots of various motifs at various genomic loci, generated in accordance with various embodiments of the invention.
Figure 50:
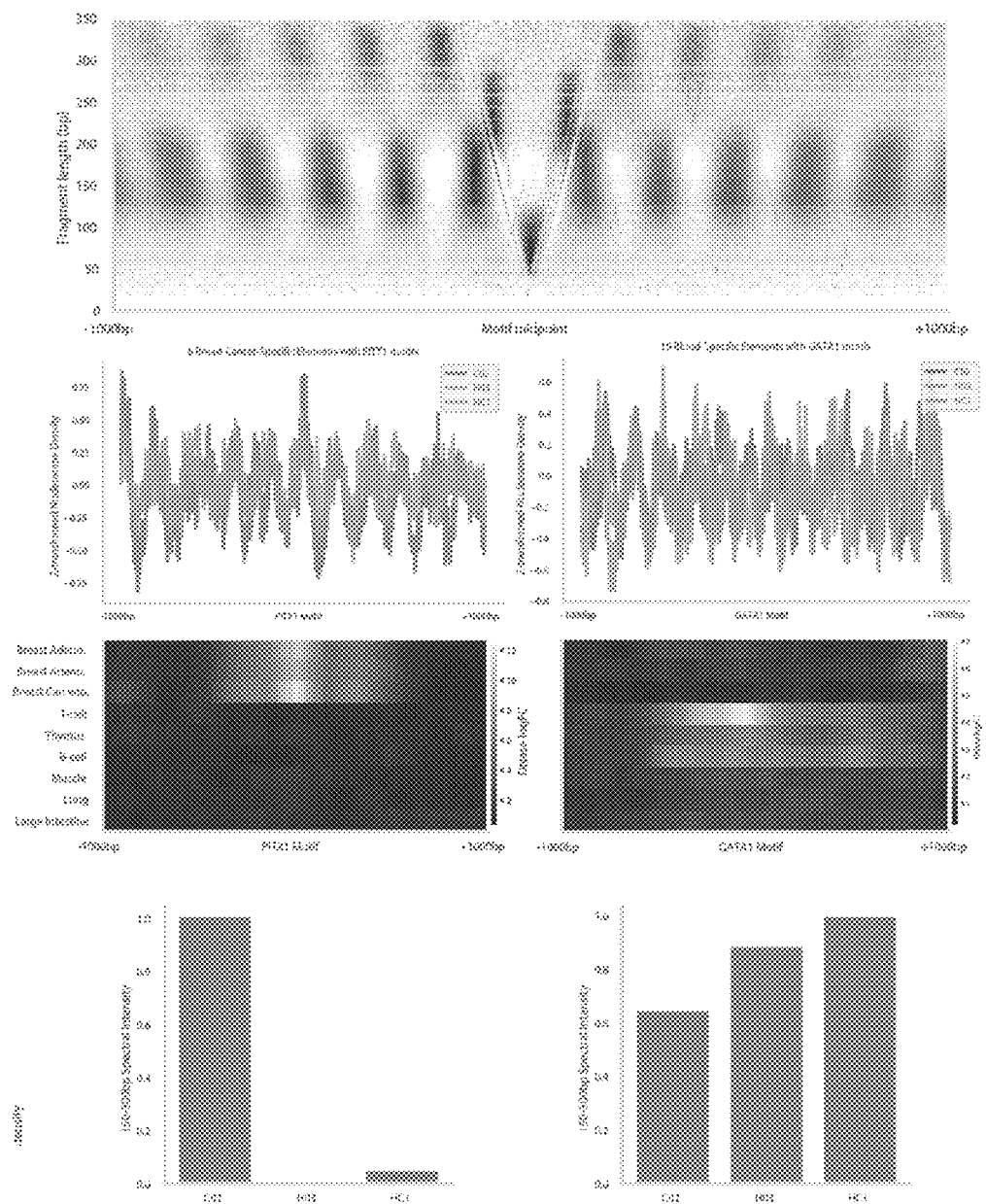
Figure 51:
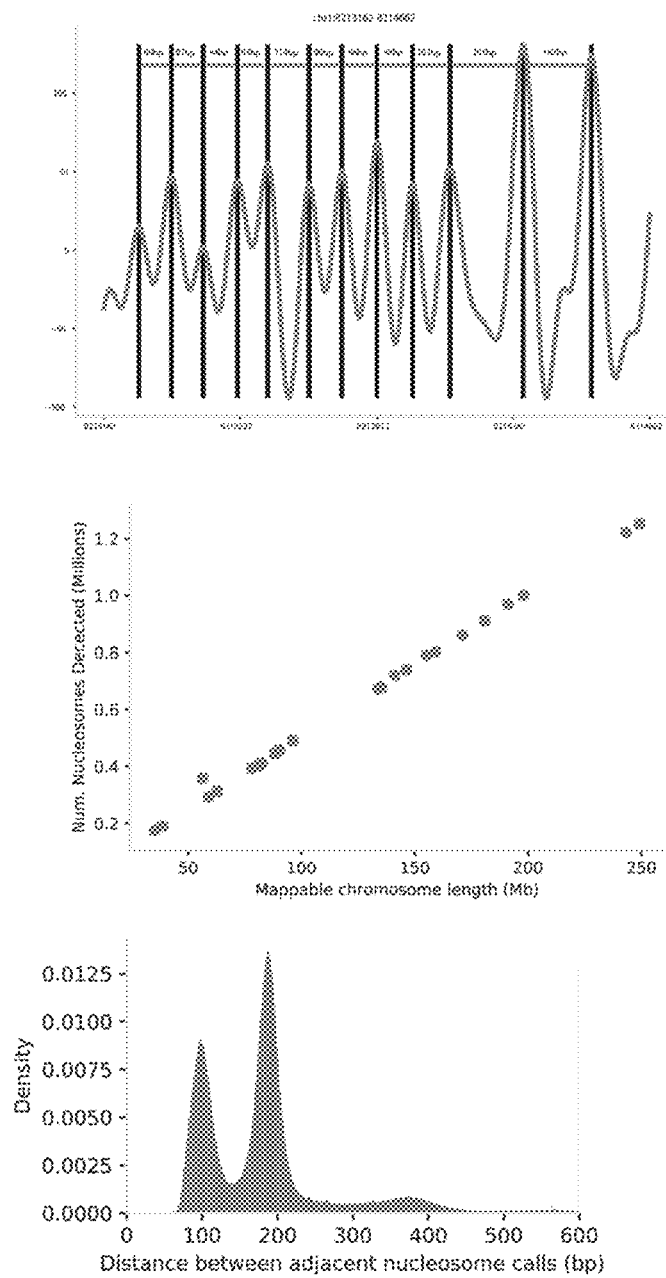
FIG. 51 provides various data graphs characterizing nucleosomes detected, generated in accordance with various embodiments of the invention.

Given the central role of nucleosome positioning in cfDNA sequence, an optimal filter to detect nucleosome positioning from cfDNA fragmentation matrixes was determined. A conditional expectation-maximization procedure was used to learn a novel nucleosome detection filter (Nucd) that is highly optimized for detecting positioned arrays of nucleosomes at active regulatory sites with minimal background signal or edge effects. An extremely high coverage (700× median coverage, 28B unique fragments) genome-wide cfDNA fragmentation V-plot was first generated by pooling sequencing data from 18 unrelated individuals. To design the Nucd filter, reads were aggregated across 15K high-confidence CTCF peaks from CTCF ChIP-seq in the GM12878 cell line, selecting only peaks in which a single high-confidence CTCF motif overlapping the called peak summit. The resulting aggregate V-plot contains 151M cfDNA fragments over a 2000 bp interval, and depicts a canonical TF binding site flanked by strongly positioned nucleosomes. Row-wise mean background subtraction was performed, and then aggregated a nucleosome profile across the column-wise summed density summit positions of the 6 density maxima (nucleosomes) with closest distance from the motif midpoint. This provides an initial filter, which depicts an approximately Gaussian mass centered on 171 bp length, with radially symmetric standard deviation 11 bp. This analysis is shown in FIGS. 49, 50, and 51.

Ten thousand chromatin elements were used as a training set to optimize over from the merged peakset with maximal mean normalized signal over all hematopoietic and lymphoid celltypes. Since cfDNA is thought to arise primarily from hematopoietic and lymphatic cell types, this peak set was expected to correspond to peaks with strong signal across individuals, including in individuals with fetal or malignant cfDNA sources, since the maximum described proportion of plasma cfDNA from such sources is ~30%. In each subsequent step of the optimization procedure, the filter is cross-correlated with a 5000 bp interval centered on the summit of each of the 10K high blood signal peaks. The expectation-maximization procedure used to learn the Nucd filter is further described in the Methods section below. This analysis is shown in FIGS. 49, 50, and 51.

Compared to existing nucleosome detection filters, the learned Nucd filter is remarkably sparse. Less than 1% of the cells in the 400 bp×200 bp filter contain >99% of the mass. In other nucleosome detectors, such as Gaussian distributed filters, and the Window Protection Score (WPS), the mass is spread over a large proportion of the filter, >60% of the area in both cases.

The performance of the Nucd filter was analyzed relative to two other approaches: Gaussian-smoothed fragment midpoint counts, and the window protection score (WPS). Within a single locus, the outputs of all 3 filters are very similar, however Nucd has a higher proportion of energy focused on the nucleosome frequency band than either WPS or Gaussian filters. Nucd also has a significantly higher mean window displacement for windows 30 bp-300 bp than WPS or Gaussian filters. Both results suggest that Nucd is marginally more sensitive to individual nucleosomes at a single locus than WPS or Gaussian filters.

Filter performance and signal coherence was also evaluated in an aggregate of loci, which is also the signal type used for tissue of origin inference (described below). In these settings, Nucd has substantially higher proportion of spectrogram energy contained in the mononucleosome (150-300 bp) frequency band. Nucd also exhibits higher mean windows displacement at corresponding window sizes (30-300 bp). These findings demonstrate that Nucd is superior to L-WPS or Gaussian smoothing for detection of positioned nucleosomes in aggregates of multiple aligned loci.

The 20 deepest cfDNA samples were combined from 18 unrelated individuals to produce an aggregate reference map of in vivo nucleosome positioning. The dataset comprises 28 billion unique paired-end fragments, yielding >700× median genome-wide coverage. By comparison, the deepest such in vivo map which is available publically contains only 1.2 billion fragments, so this map is ~24× greater maximum resolution. This data is shown in FIGS. 49, 50, and 51.

An optimized single base pair resolution nucleosome detection pipeline was developed (detailed in Methods section below) which uses the Nucd learned nucleosome cross-correlation filter to detect nucleosome fragmentation profiles from raw V-plots and gradient-based post processing to refine candidate nucleosome calls. Using the Nucd nucleosome detector, 15.7M nucleosome sites was identify in the high-coverage aggregate sample. Notably, the calls have single base pair resolution for each nucleosome occupancy peak: several existing call sets contain intervals of varying widths and take the midpoint of the window as the "position" of the nucleosome, although many of the windows are several times larger than canonical TF nucleosome footprints. Outputs of the nucleosome calls are shown in FIG. 51.

By combining the high coverage sample (>700× depth) with the highly sensitive Nucd nucleosome detector, evidence of alternatively phased nucleosome arrays was identified. Nucleosome displacement and variable positioning is widely associated with gene expression and chromatin element activity, and the majority of counterphase nucleosome arrays that were detected are within 2000 bp of DNase peaks in the multi-tissue index, suggesting association with variable chromatin element activity. This results in a high density of detected nucleosome positions, some of which are mutually incompatible due to steric hindrance and electronegative repulsion. Notably, the internucleosomal distance distribution of the nucleosome calls is bimodal: a subset of calls in counter phased arrays have median internucleosomal distance of 91 bp, whereas the mode at 183 bp represents mononucleosomes. The 2:1 ratio of the modes is further evidence of counterphasing: the smaller mode exists at exactly the half wavelength of the primary mononucleosome spaced signal. An example of this phasing is shown in FIG. 51.

Despite the calls being higher resolution, a strong concordance was seen with previously reported nucleosome call sets, which are also recorded from cell-free DNA and are closest in depth among available in vivo data. The highest coverage sample previously used yielded 12.8M nucleosome calls, so the 15.7M described herein represents a 22.6% relative increase in total nucleosomes called. However, the deepest comparable nucleosome calls have >50 bp resolution of the occupancy summits, whereas ours are resolved to single base pair coordinates.

The nucleotide sequence frequency distribution proximal to the nucleosome peak calls mirrors the previously reported GC-rich core region thought to interact through favorable electronegativity with histone residues, and the AT-rich flanking regions, thought to be involved in maintaining nucleosome position and reducing helical strain in linker DNA adjacent to nucleosomes. However, the extent of the sequence bias more closely mirrors that seen in previous studies of cell-free DNA and nucleosome preference from ATAC-seq than it does from studies of nucleosome position from MNase. These results further support previous findings that MNase confers strong sequence bias that confounds detected nucleosome positioning preferences.

The genome-wide Nucd nucleosome positioning scores were used to investigate TF footprinting. A set of 17 diverse TFs were selected for which CIS-BP contains at least one high-confidence motif, and for which high-quality ChIP-seq signal exists in GM12878. The same blood-derived cell line was used for all TFs because it is the most extensively profiled cell line in ENCODE, and to minimize differences in signal profiles across TFs. IDR optimal peak summits were taken for each TF and intersected them with FIMO CIS-BP scores. For peak summits with more than one motif intersection, the occurrence with the lowest adjusted p-value was selected (ties were broken arbitrarily). The Nucd traces were aggregated in 10 Kb intervals centered on these motif-peak summit intersection sets across all TFs, mirroring the Nucd signal with respect to the strand of the TF motif (i.e., sites with the motif on the negative strand were reversed, centered on the TF motif). Signals were Z-normalized using the flanking 2 Kb regions on both edges of the regions to calculate the mean and variance, and then averaged across all sites. Outputs of this analysis are shown in FIG. 49.

The aggregate Nucd traces illustrate highly distinct nucleosome positioning and occupancy profiles for across TFs. CTCF has the most consistent nucleosome positioning (largest variance-normalized dynamic range), and is overall highly symmetric. This is consistent with the extensive literature on CTCF binding, which indicates that CTCF sites have strongly positioned flanking nucleosome arrays. Another master chromatin regulator, Polycomb Group Protein YY1 is known for asymmetric binding profiles, because of extensive heterodimerization. The aggregate Nucd trace for YY1 is asymmetric, clearly showing higher nucleosome occupancy 3' of the binding site. ChIP-seq evidence shows that YY1 cofactors often bind 5' of the protein, which correlates with the reduced nucleosome occupancy on that side of the motif, likely driven by variability in cofactor binding patterns. Outputs of this analysis are shown in FIG. 50.

Having identified extensive differences in nucleosome contexts between TFs, it was next sought to better profile the diversity of binding contexts within the sites bound by each TF. An existing method (CAGT) for clustering epigenomic signals was leveraged. Briefly, the method first performs k-medians clustering using Pearson correlation on the normalize signals to identify a large number (k=30 in the current analysis) of compact (low intracluster variance) but redundant clusters. The second step of the pipeline performs agglomerative hierarchical clustering again using Pearson correlation distance, but at each step considering both the set of clusters, and the mirrored signal of each cluster (to account for orientation uncertainty in the input signals). The output of this clustering was taken, and clusters were allowed to merge when the Pearson distance was <0.25 (Pearson correlation >0.75). Clusters that accounted for fewer than 5% of total peaks for each TF were also filtered. This yielded 1-5 distinct clusters for each TF, each with distinct nucleosome footprint patterns. In many cases (e.g. for CTCF), the revealed intrinsic diversity in nucleosome footprinting appears to correlate with TF occupancy. A more positioned nucleosome signature at the TF motif midpoint is consistent with reduced TF binding, whereas a reduction in nucleosome occupancy (and a corresponding increase in shorter TF-derived fragments) at the motif center indicates stronger TF occupancy (a more active TF binding context). In other cases, the revealed diversity is suggestive of heterogeneity in binding patterns, such as TF dimerization. The clustering also reveals extensive diversity in the spacing of adjacent nucleosomes, which is likely correlated with the different levels of activity of different TFs. Such nucleosome frequency diversity is clearly visible in FIG. 48, which demonstrates that for different levels of chromatin element activity, the nucleosome spacing varies considerably.

Inference of Regulatory Element Activity from Cell-Free DNA Fragmentation Profiles It was observed that in the high-coverage pooled cfDNA sample that chromatin elements active in blood cell types have highly distinct nucleosome density profiles than chromatin elements inactive in blood cell types. This finding aligns with several other reports demonstrating that element-proximal nucleosome arrangement directly captures local chromatin state. This is illustrated in the stratification shown in FIG. 43.

Nucleosome positioning at active elements exhibits stronger dynamic range and nucleosome frequency band energy, appears more tightly controlled in active elements, likely deriving from coherent, in-phase positioning across bulk cells. In contrast, inactive elements exhibit lower dynamic range, and a lower proportion of nucleosome wavelength energy, suggesting more destructive interference arising from counterphase aggregation across cells in bulk samples, which is shown in FIG. 43.

While previous findings have reported a linear relationship between promoter-proximal cfDNA read depth and promoter activity (i.e. gene expression), herein no such relationship was observe for enhancers. First, it was tested whether any depth bias exists within highly active or inactive blood-specific elements relative to dinucleotide frequency matched regions selected randomly from the genome, and found no significant effect. It was then tested whether any linear trend existed between fragment depth and chromatin element activity, and found no significant correlation. Such hypotheses for other more specific sets of elements were also tested, e.g. CTCF sites only, and still found no strong depth signal of chromatin element activity in cfDNA. These findings imply that chromatin state is reflected in cfDNA purely through fragmentation pattern (joint spatial distribution), and not through depth (marginal spatial distribution).

The relationship between element activity and fragmentation pattern was further evaluated by aggregating Nucd traces over sets of elements partitioned by their mean signal in blood celltypes. Six sets of 5,000 elements were randomly selected, each corresponding to 20 percentile increments of the blood tissue signal intensity scale, and Nucd traces were aggregated across each set. The resulting ordering demonstrates that area above the Nucd curve scales linearly with element activity across multiple scales of element width (e.g. both when considering only the central 200 bp, or the central 2000 bp). Additionally, the spectrograms of these profiles demonstrate that proportion of energy within the nucleosome frequency band correlates directly with element set activity. Together, these results establish a clear relationship between cfDNA fragmentation pattern and chromatin element accessibility signal from DNase-seq in celltypes contributing to cfDNA. These results are shown in FIG. 43.

Having established a relationship between cfDNA fragmentation pattern and chromatin element accessibility, it was sought to test whether imputed accessibility of tissue discriminative elements correlates with expected tissue contribution to cfDNA in clinical samples. To this end, samples from patients with metastatic breast cancer (n=5), metastatic skin cancer (n=2), metastatic colorectal cancer that metastasized to the ovary (Krukenberg tumor, n=1), and a healthy control sample were examined, shown in FIG. 44.

In all cases of metastatic cancer, the site of primary disease is detected as a top-3 tissue of origin, even though none of these tissues (breast, skin, GI) are detected as a top-10 tissue in healthy controls, and the estimated abundance of the tissue correlates with the tumor fraction estimated by CNA analysis (FIG. 43). In the healthy control sample, imputed tissues of origin correlate with previously established results, including hematopoietic, lymphoid and myeloid contributions (FIG. 44).

To test the analytical sensitivity and internal consistency of our method as a function differential sequencing depths and tumor fractions, a series of genome-wide in silico subsampling and titration experiments were performed. First, an experiment (detailed in Methods section below) was performed to support that the local subsampling procedure used to generate the remainder of the subsampled results is equivalent to a less efficient global subsampling. The cfDNA data shows no detectable depth bias on this scale (200 Kb). Importantly, the local subsampling procedure is robust to copy number aberrations (i.e., it mirrors the copy number bias of the original data, equivalent to global subsampling).

As a first experiment, the depth dependence of the tissue of origin classification was tested. For each sample evaluated, the tissue of origin estimates were derived as previously stated, using aggregate Nucd traces overlapping sets of tissue discriminative elements for each tissue assayed across 10 Kb regions. Resulting traces are Z-normalized, using the flanking 2 Kb windows to derive estimates of the mean and standard deviation parameters that are robust to element activity levels. Tissues are ranked according to their normalized spectrogram intensity within the 150-300 bp band. The procedure is repeated for 5 replicates across each sample, and performed for 20 subsampling depths, ranging from 1E-3× to 1× original depth. The results demonstrate that for all samples, strong concordance with the full depth is achieved by 10-20× genome-wide depth, and, that for clinically significant detection (e.g. of the primary and metastatic sites of disease being non-zero in patients MBC1 and MBC2), that the signals are present at 5× genome-wide depth. These results demonstrate that the performance of our method is robust at lower sequencing depths, which is important for clinical applications where cost and data processing times are key considerations. Results of these experiments are shown in FIG. 44.

It was then sought to evaluate the ability to resolve tumor fraction at low levels of disease burden. To this end, we performed a series of titration experiments, where reads from a cancer cfDNA sample are stochastically mixed into reads from a healthy control sample, and tissues of origin are estimated as before. This procedure was performed with 5 replicates for two samples: MBC2 (metastatic breast cancer), and MGC1 (metastatic colorectal cancer), both titrated into HC1 (healthy control). Samples were first subsampled to equal original depth, so that mixture proportion does not affect effective sequencing depth. We then evaluated the mixture sensitivity at different tumor sample proportions, ranging from 1e-3 to 1.0. After obtaining tissue of origin estimates for each cancer sample fraction in each replicate, we fit a linear model between effective tumor fraction (tumor sample fraction*CNA estimated tumor fraction) and the estimated primary tissue of origin (breast for MBC2, colon for MGC1), using leave-one-out cross validation for each fraction, reporting only the validation point. Using a joint featurization of Nucd AUC and Nucd spectrogram intensity, we observe almost perfect correlation between true and predicted tumor fraction across all 5 replicates (rA2=0.997, p<1e-9). Considering only lower effective tumor fractions (<10% effective tumor fraction), the correlation achieved is (rA2=0.993, p=1.5e-5), demonstrating the correlation is not just driven by high tumor fraction data points. Together, these results demonstrate the method is highly accurate at measuring functional signatures of tumor presence from DNA fragmentation patterns in an otherwise normal sample, even at low tumor fractions that are clinically meaningful in the context of early cancer detection. Results of this analysis are shown in FIG. 45.

It was also sought to identify transcription factors driving tissue-specific regulatory element accessibility. YAMDA (see D. Quang, Y. Guan, and S. C. Parker, Bioinformatics 34, 3578-3580 (2018), the disclosure of which is incorporated herein by reference) was run on the 1,000 top breast-specific and lymphoid/erythroid ("blood") specific DNase elements, using the 10,000 top system-specific elements from all other systems as a background input. YAMDA was used to search for up to 5 motifs in both cases, and then MEME was used to label the motifs. For breast, the top hit was PITX1 (matching n=5/5 motifs), and for blood GATA1 (matching n=4/5 learned motifs). cfDNA Nucd signals were then aggregated across the top 100 elements containing FIMO hits of these PWMs, yielding n=8 PITX1 elements and n=19 GATA1 containing elements. cfDNA Nucd traces were aggregated over these elements, as well as DNase logFC signal tracks from selected RoadCODE samples (FIG. 50). The 150-300 bp relative spectral energies of the Nucd signal aggregated were also calculated across these sites for 3 different cfDNA samples. The results demonstrate that these TFs bind tissue-specific elements in DNase, and that the differential element activity can be reconstructed in cfDNA samples containing the associated tissue of origin (e.g. MBC1 time point 1 shows strongly differential PITX1 element activity; all samples show significant GATA1 activity). Thus, although the reference dataset only requires chromatin accessibility input for each tissue (rather than separately performing TF ChIP-seq experiments for many TFs in each tissue of origin), the method was able to both detect and leverage tissue-specific TF binding patterns to further distill the tissue of origin signals detected.

Correlation with Clinical Presentation in Case Studies

Figure 52:
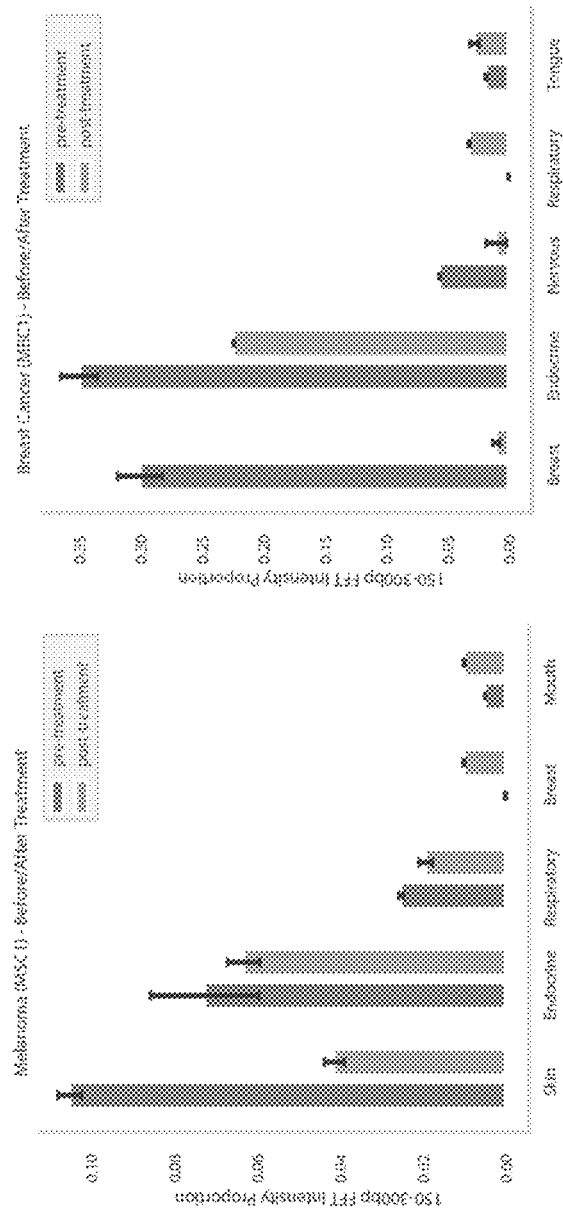
FIGS. 52 & 53 provides data graphs comparing detection of various tissues pre- and post-treatment, generated in accordance with various embodiments of the invention.
Figure 53:
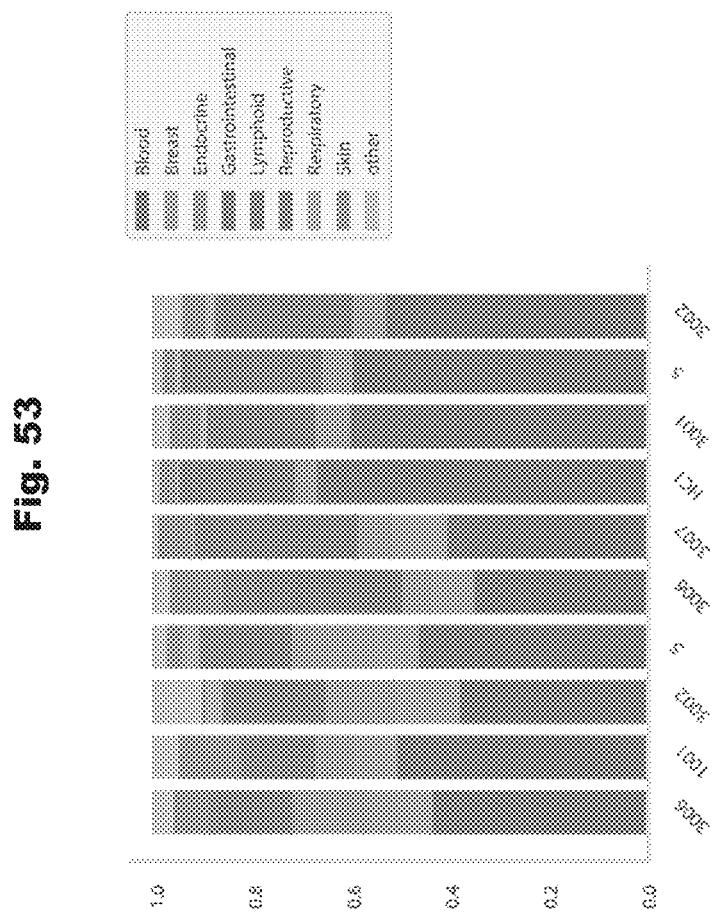

To further illustrate the clinical relevance of the method, cfDNA samples obtained from patients with metastatic and early-stage disease were utilized as case studies to evaluate how well predictions aligned with clinical presentation and treatment response. The patient cohort included ten high-coverage samples from seven individuals: three patients with metastatic breast cancer (MBC1, MBC2, MBC3), for which MBC1 and MBC2 had both pre and post treatment time points, two patients with early-stage breast cancer (EBC1, EBC2), one patient with metastatic colon cancer (MGC1), and one patient with metastatic melanoma (MM1), who also had pre and post treatment time points. These results are shown in FIGS. 44 and 52.

All three metastatic breast cancer patients presented with high tumor burden at the time of initial sampling (23-32% by consensus CNA estimate). Of the two patients (MBC1, MBC2) with post-treatment time points, one patient (MBC1) responded well to treatment, and had no detectable breast tissue of origin, or detectable tumor fraction based on clonal CNAs. Patient MBC2 did not respond to treatment, and both her estimated breast tissue fraction and tumor CNA fraction increased significantly. Results shown in FIGS. 44, 52, and 53.

The longitudinal dynamics of treatment response was compared in two initially treatment naïve patients with metastatic disease who were treated with targeted therapies for whom we had serial cfDNA blood draws before and after treatment, as well as accompanying clinical information. The top five tissues by the absolute change in tissue signal are shown at both pre-treatment and post-treatment time points. The signals shown are normalized by the "blood" tissue signal in each sample, which empirically improves correlation across samples by acting as an internal control. Patient MM1 had a pre-treatment cfDNA blood draw, and then was treated for metastatic melanoma, first with surgery and radiotherapy, and then with vemurafenib (a BRAF inhibitor), which was discontinued after one cycle, and then ipilimumab (a CLTA-4 targeted immunotherapy), which was discontinued after four cycles due to progression. The dynamics of the tissue of origin spectrum match the clinical presentation: skin achieves an almost 50% reduction, while endocrine signal is significantly increased, likely related to the adverse treatment response. At right, patient MBC1 with de novo stage IV, untreated HER2+ breast cancer had a pre-treatment cfDNA sample, and was then treated with trastuzumab and chemotherapy for one cycle, after which she achieved a durable partial response. The very large reduction in breast signal correlates with the strong clinical treatment response, while other tissues had much smaller absolute differences. These results are shown in FIG. 52.

Patient MGC1 had a colorectal cancer primary tumor that metastasized to the ovary (Krukenberg tumor), a rare and aggressive diagnosis. Gastrointestinal tissue is the top predicted non-blood tissue of origin and reproductive tissue is predicted as a high tissue of origin. At the organ level, the large and small intestine are significantly elevated, and ovary is also a top-10 tissue of origin, which is not observed in any other patient (FIG. 52).

Patient MM1 had metastatic melanoma at the time of initial sampling. He was subsequently treated with the BRAF inhibitor vemurafenib and then CTLA4 targeted therapies. Vemurafenib was discontinued due to acute kidney failure, and ipilimumab was subsequently discontinued due to disease progression. Despite this fact, treatment did substantially decrease tumor burden, which is also supported by a reduction in mutational frequency measured by targeted ctDNA sequencing. The computed tissue of origin distribution identifies significant skin tissue in both samples, but with a 4× reduction between the initial and follow up time point, which is directly comparable to the observed reduction in tumor VAFs. Intriguingly, between the two time points, endocrine is substantially elevated (2×), which is consistent with reports of endocrine-related adverse events following anti-CTLA4 treatment for metastatic melanoma. Shown in FIG. 52.

Methods

Cell-free DNA Sequencing: cfDNA samples were collected in Streck cell-free DNA BCT tubes (cat no. 218962), and processed according to the manufacturer directions. DNA was extracted within 12 hours using the Qiagen Circulating Nucleic Acid Kit (cat no. 55114), following manufacturer directions. Libraries were prepared with unique paired-end UMIs using the Rubicon/Takara Bio ThruPLEX Tag-seq 96D Kit (cat no. R400586), according to manufacturer directions. Libraries were sequenced either on a NextSeq 500 150 cycle (76 bp PE), or NovaSeq 5000 S2 300 cycle (150 bp PE) run, using dual index sequencing adapters. Demultiplexing was performed using bcl2fastq v2.19.0, allowing up to one barcode mismatch per read.

Cell-free DNA Bioinformatics Pipeline: A novel end-to-end bioinformatics pipeline was developed for analysis of fragmentation patterns in whole-genome cell-free DNA sequencing datasets. The pipeline is based on the Toil framework, which can run locally, on HPC clusters with various scheduler systems, and on all major cloud platforms. The pipeline scales to thousands of samples with billions of reads per sample, and uses a highly fault-tolerant distributed architecture. In addition to using many existing programs (bwa mem, samtools, sambamba, Picard, bedtools, MultiQC), the pipeline also includes several custom algorithms implemented in Python, C++, Nim, and D languages for paired-end UMI extraction, adapter sequence annotation, high performance paired-end UMI deduplication, and fragment-level library GC bias resampling to a median reference GC distribution. All code and documentation will be made publicly available at https://github.com/kundajelab/cfdna-pipeline, the disclosure of which is incorporated herein by reference.

RoadCODE Uniform Data Processing: Raw Fastq files were obtained from the ENCODE project consortium website (https://www.encodeproject.org/). Fastqs were trimmed to 36 bp, and then aligned to the ENCODE hg19/GRCh37 male genome assembly (ENCSR425FOI) with BWA aln (v0.7.10), with all datasets treated as single-end. Dynamic read trimming was set to 5, the seed length was 32, and 2 mismatches were allowed. After mapping, reads were filtered to remove unmapped reads and mates, non-primary alignments, reads failing platform/vendor quality checks, and PCR/optical duplicates (-F 1804). Low quality alignments (MAPQ<30) were also removed. Duplicates were then removed with Picard MarkDuplicates (v1.127). The filtered BAM files were converted to tagAlign format (BED 3+3) using bedtools bamtobed. Cross-correlation scores were obtained for each file using phantompeakqualtools (v1.1), and files with cross-correlation quality tag below 0 were discarded. tagAlign files were filtered to remove mitochondrial reads, filtered for 36 bp unique mappability, and pooled across technical replicates, and then subsampled to 50 million reads per sample. Signal tracks and peaks were called with a loose threshold (p<0.01) with MACS2 (v2.1.0) to generate bigwig files (fold enrichment and p-value) and Narrow Peak files, respectively. Peaks were merged across all samples using bedtools (v2.25) merge, requiring >0.5 proportion overlap between merged peaks. The peak/tag intersection matrix was calculated using bedtools (v2.1.0) intersect between the merged master peak file and the filtered, down sampled tagAligns. The peak/sample count matrix was normalized using limma, an RNA quantification tool that corrects for overdispersion and other count artifacts. Finally, using the labels described above derived through query of the ENCODE API with manual curation, we performed differential accessibility analysis of each element for each category of system, organ, and cell type using both Voom linear model and weighted mutual information against a category membership binary indicator matrix.

Cell-free DNA data analysis: A Python package was developed for all analysis as described in this example. One of the core components of the package is the preprocessing module, which includes code for preprocessing DNase-seq reference datasets, learning optimized nucleosome detection filters, GPU-accelerated cross-correlation of genome-wide cell-free DNA V-plots, and several other preprocessing steps. The package also includes an analysis module, which contains algorithms for all tissue-of-origin signal analysis presented in the paper. Additionally, the package provides several useful features for optimized storage of genome-wide signal tracks as hdf5 files with high performance compression filters, and a Cythonized module for efficiently querying hundreds of genome interval datasets containing millions of peaks. The package will be made publicly available at https://github.com/kundajelab/cfdna-analysis.

Inference of the Nucd filter: The Nucd filter is learned from the high-coverage aggregate V-plot containing pooled reads from all samples presented in the study. The filter is initialized using aggregate nucleosome positions proximal to IDR CTCF peaks that intersect DNase peaks in high-quality RoadCODE lymphoid samples. V-plots were extracted in 10,000 bp windows around 10,000 high lymphoid signal chromatin elements. The 100 maximum cross correlation indexes formed with the existing filter (with a 100 bp size exclusion window on previously called maxima) are aggregated as the "foreground", and the 100 cross-correlation minima (defined with the same 100 bp size exclusion window) are aggregated as "background". The foreground and background of each peak are row mean background subtracted, and the resulting composite images for all peaks are averaged. The final mean background is elementwise subtracted from the mean foreground image, giving a differential positioned nucleosome signature. The procedure is repeated until the filter achieves convergence, defined by asymptotically decreasing mean elementwise difference from the previous filter, which was 10-12 iterations.

Equivalency of Local Subsampling Procedure: First, it was sought to demonstrate that fragment-level subsampling over large (200 Kb) regions is equivalent to subsampling unaligned reads. The genome-wide alignment of the aggregate pooled sample to 50% of its original depth (14 billion fragments) was downsampled and the resulting V-plot was cross-correlated with the Nucd filter. Then, a local subsampling procedure was performed, which was more efficient but a heuristic of global subsampling, on windows of size 200 Kb. The Nucd signal of this subsampling across 5 replicates was calculated. It was then tested whether the residual of the globally subsampled signal from the mean of the locally subsampled replicates was significant, compared to the residual (i.e., standard deviation) of the locally subsampled signals. The globally subsampled signal had a residual of 1.3e-3, whereas the mean residual of the locally subsam pled replicates was 1.8e-3.

Genome-wide Nucleosome Calling: Nucleosome positions are called from Nucd filter cross-correlation with a given sample V-plot. The genome-wide Nucd/V-plot cross-correlation was performed on an NVIDIA GPU. For each chromosome, the signal was first smoothed with a 21 bp Savitzky-Golay filter (2nd order), and then the signal range was adaptively attenuated by scaling the signal by the 98th percentile value, and then the inverse sine transform (arcsinh) calculated, providing exponential decay of high-signal (likely artifact) regions. The signal was then Z-scaled by subtracting the mean and dividing by standard deviation. A band-pass filter was then applied, retaining only 1/50 bp-1/600 bp components of the real-valued fourier transform, removing both high frequency and low frequency noise from the nucleosome signal (~1/180 bp). The normalized signal was applied to a 30 bp sliding maximum filter, followed by a 20 bp non-maximal suppression filter between adjacent called maxima. Candidate peak positions were then filtered based on the prominence of the peak. Within a 41 bp window centered on the peak, each peak must have a 1 bp analytical gradient (smoothed using the same filter parameters as the input signal) below the 20th percentile and one above the 80th percentile of genome-wide gradients. Empirically, the gradient-based filtering greatly reduces the number of false positives without significantly hurting sensitivity for apparent nucleosome signal.

DOCTRINE OF EQUIVALENTS

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

What is claimed is:

1. A clinical method for screening an individual's cell-free nucleic acid sample using sequencing data to detect nucleic acids of abnormal tissue origin or cell type in the cell-free nucleic acid sample in order to perform a clinical action, comprising:
    obtaining, using a computing system, a sequencing result comprising sequence read fragments of a cell-free nucleic acid sample extracted from the individual; and
    generating, using the computing system and the sequencing read fragments, a frequency signal map of the cell-free nucleic acid sample, the frequency signal map comprising a plurality of chromatin-related nucleic acid signals, each chromatin-related nucleic acid signal annotated a genomic position,
        wherein the amplitude of each chromatin-related nucleic acid signal corresponds to the frequency of the sequence read fragments at a particular genomic locus;
    constructing, using the computing system, a two-dimensional V-plot for each signal of the frequency signal map, wherein each V-plot is a measure of the frequency of sequence read fragments and the length of each sequence read fragment;
    predicting, using the computing system, a trained computational model, and the constructed V-plots, that a tissue origin or a cell type is associated with the cell-free nucleic acid sample, wherein the tissue origin or the cell type is solid tissue; and
    based on the tissue origin or the cell type being solid tissue, administering a diagnostic test to assess whether the individual has a medical disorder in tissue of the tissue origin or the cell type.

2. The method of claim 1, wherein the extracted nucleic acids are extracellular nucleic acids.

3. The method of claim 1, wherein the extracted nucleic acids are one of: cell-free DNA or cell-free RNA.

4. The method of claim 1, wherein the extracted nucleic acids are RNA, and wherein the RNA is used to derive the chromatin-related nucleic acid signals.

5. The method of claim 1, wherein the extracted nucleic acids are extracted from at least one of: blood, plasma, serum, lymphatic fluid, cerebral spinal fluid, urine, feces tissue biopsy, or isolated single cells.

6. The method of claim 1, wherein the at least one chromatin-related factor includes at least one of: a chromatin marker, a histone, a histone variant protein, a DNA-methyl-binding protein, a transcription factor, an enhancer, and a repressor.

7. The method of claim 1, wherein the chromatin-related nucleic acid signals are assigned a genomic position based on a reference sequence.

8. The method of claim 7, wherein the chromatin-related nucleic acid signals are clustered based on their genomic position to yield a frequency sequence signal map.

9. The method of claim 1, wherein determining or having determined whether a biological attribute is associated with the individual's chromatin-related nucleic acid signals further comprises:
constructing V-plots for the chromatin-related nucleic acid signals of the individual, wherein the V-plots are each a 2-D pattern of a number sequence read fragments, and wherein the fragment length is plotted against fragment position in genome;
associating the V-plots with the biological attribute;
aggregating and aligning V-plots based on genomic position; and
entering the V-plots into the trained computational model to determine whether the biological attribute is associated with the individual's chromatin-related nucleic acid signals.

10. The method of claim 9, further comprising at least one of:
compressing the V-plots by binning or pooling sequence read fragments;
reweighing the V-plots based on the sequence composition or sequence frequency; or
filtering the V-plots to further differentiate the corresponding signals of each V-plot.

11. The method of claim 1, wherein the trained computational model is one of: a generative adversarial network, a convolutional neural network, a random forest, a support vector machine, or a boosted decision trees.

12. The method of claim 1 further comprising:
predicting, using the computing system, the trained computational model, and the constructed V-plots, that a pathological status is also associated with the cell-free nucleic acid sample, wherein the trained computational model has been trained utilizing chromatin-related nucleic acid signals associated with the pathological status, wherein the pathological status is one of: presence of a solid tissue neoplasia, presence of a placental disorder, presence of tissue inflammation, or presence of neurodegeneration.

13. The method of claim 12, wherein the pathological status is presence of a solid tissue neoplasia.

14. The method of claim 13, further comprising administering an additional diagnostic test, wherein the additional diagnostic test is one of: a physical exam, medical imaging, mammography, endoscopy, stool sampling, a pap test, an alpha-fetoprotein blood test, a CA-125 test, a prostate-specific antigen (PSA) test, a biopsy extraction, a bone marrow aspiration, and a tumor marker detection test.

15. The method of claim 13 further comprising administering a treatment for the neoplasia, wherein administering a treatment comprises administering at least one of: surgery, chemotherapy, radiation therapy, immunotherapy, targeted therapy, hormone therapy, stem cell transplant, or blood transfusion.

16. The method of claim 13, wherein the presence of neoplasia is determined during a course of a treatment regimen such that the effects of the treatment regimen on neoplastic growth is monitored.

17. The method of claim 13, wherein the presence of neoplasia provides detection of residual neoplastic growth or recurrence of neoplastic growth.

18. The method of claim 12, wherein the pathological status is presence of tissue inflammation, and wherein the tissue inflammation is one of: appendicitis, colitis, Crohn's disease, cystitis, endocarditis, gastritis, hepatitis including cirrhosis, inflammatory bowel disease, myocarditis, neuritis, pancreatitis, pericarditis, or pneumonitis.

19. The method of claim 18 further comprising administering an additional diagnostic test, wherein the additional diagnostic test is one of: a physical exam, medical imaging, a biopsy extraction, endoscopy, an echocardiogram, an electrocardiogram, a pulmonary function test, or a blood test.

20. The method of claim 18 further comprising administering a treatment for tissue inflammation, wherein the treatment is one of: surgery, administration of an anti-inflammatory, administration of an antibiotic, administration of an antiviral, intravenous fluids, and administration of a pain reliever.

21. The method of claim 18, wherein the presence of tissue inflammation is determined after a course of a treatment regimen such that residual tissue inflammation or recurrence of tissue inflammation is monitored.

22. The method of claim 12, wherein the pathological status is presence of neurodegeneration, and wherein the neurodegeneration is one of: Alzheimer's disease, amyotrophic lateral sclerosis (ALS), dementia, Huntington's disease, or Parkinson's disease.

23. The method of claim 22 further comprising administering an additional diagnostic test wherein the additional diagnostic test is one of: a physical exam, medical imaging, a biopsy extraction, a neurological test, an electrodiagnostic test, a memory test, a genetic test, and a blood test.

24. The method of claim 22 further comprising administering a treatment for neurodegeneration, wherein the treatment comprises administration of: cholinesterase inhibitors, memantine, riluzole, edaravone, tetrabenazine, antipsychotic drugs, carbidopa-levodopa, dopamine agonists, or MAO B inhibitors.

25. The method of claim 22, wherein the presence of neurodegeneration is determined during a course of a treatment regimen such that the neurodegeneration process is monitored.

26. The method of claim 12, wherein the pathological status is presence of a placental disorder, and wherein the placental disorder is one of: placental abruption, placenta accrete, placenta increta, placenta percreta, chorioamnionitis, intervillositis, TORCH infections, cytomegalovirus infection, chronic deciduitis, circumvallate placenta, placenta previa, vasa previa, chorangioma, placental infarction, choriocarcinoma, or hydatidiform mole.

27. The method of claim 26 further comprising administering an additional diagnostic test, wherein the additional diagnostic test is one of: physical exam, medical imaging, and blood tests.

28. The method of claim 26 further comprising administering a treatment for the placental disorder, wherein the treatment is one of: surgery, Cesarean section, anti-inflammatories, antibiotics, antivirals, intravenous fluids, and pain reliever.

29. The method of claim 26, wherein the indication of the placental disorder is determined during a course of a pregnancy such that the pathology of the placental disorder is monitored.

30. The method of claim 1, wherein administering the diagnostic test comprises administering a physical exam on tissue of the tissue of origin or the cell type, medical imaging on tissue of the tissue of origin or the cell type, a biopsy extraction on tissue of the tissue of origin or the cell type, or a tumor marker detection test on tissue of the tissue of origin or the cell type.

* * * * *